(12) United States Patent
Parsons

(10) Patent No.: US 9,017,981 B2
(45) Date of Patent: Apr. 28, 2015

(54) IDENTIFICATION OF EXTRACELLULAR FORM OF PTEN THAT CAN BE USED TO TREAT TUMORS

(75) Inventor: Ramon Parsons, Manhasset, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 13/201,969

(22) PCT Filed: Feb. 17, 2010

(86) PCT No.: PCT/US2010/000469
§ 371 (c)(1),
(2), (4) Date: Oct. 31, 2011

(87) PCT Pub. No.: WO2010/096173
PCT Pub. Date: Aug. 26, 2010

(65) Prior Publication Data
US 2012/0039861 A1   Feb. 16, 2012

Related U.S. Application Data

(60) Provisional application No. 61/207,974, filed on Feb. 17, 2009.

(51) Int. Cl.
*C12N 9/14* (2006.01)
*C12N 9/16* (2006.01)
*A61K 38/00* (2006.01)

(52) U.S. Cl.
CPC .. *C12N 9/16* (2013.01); *A61K 38/00* (2013.01)

(58) Field of Classification Search
None
See application file for complete search history.

(56) References Cited

U.S. PATENT DOCUMENTS

| 7,470,721 | B2 | 12/2008 | Durden |
| 7,732,576 | B2 | 6/2010 | Steck et al. |
| 2003/0139324 | A1 | 7/2003 | Steck et al. |
| 2004/0266713 | A1 | 12/2004 | Lu et al. |
| 2006/0204512 | A1 | 9/2006 | Krasnoperov et al. |
| 2007/0054333 | A1* | 3/2007 | Steck et al. ................ 435/7.23 |
| 2013/0171235 | A1 | 7/2013 | Parsons |

FOREIGN PATENT DOCUMENTS

JP   2008-514618   1/2006

OTHER PUBLICATIONS

Fine, "Analysis of PTEN function and regulation", Columbia University, Dissertation, Sep. 2008, AAT 3305221.*
International Search Report mailed by the International Searching Authority (ISA/US) on Aug. 30, 2010 in connection with PCT International Application No. PCT/US2010/000469, filed Feb. 17, 2010.

(Continued)

*Primary Examiner* — Patricia A Leith
*Assistant Examiner* — Erin M Bowers
(74) *Attorney, Agent, or Firm* — John P. White; Cooper & Dunham LLP

(57) ABSTRACT

An isolated human phosphatase and tensin homolog long polypeptide (PTEN-long) comprising SEQ ID NO:1, fragments and analogs thereof, nucleic acids encoding such and compositions comprising such are provided. Methods to inhibit angiogenesis in a solid tumor, treat a solid tumor, and inhibit growth of a solid tumor using PTEN-long, fragments and analogs thereof, are provided.

1 Claim, 26 Drawing Sheets

(56) References Cited

OTHER PUBLICATIONS

Written Opinion of the International Searching Authority mailed by the International Searching Authority (ISA/US) on Aug. 30, 2010 in connection with PCT International Application No. PCT/US2010/000469, filed Feb. 17, 2010.
Shechter, Y. et al. (2007). Proceedings of the 4th International Peptide Symposium in conjunction with the 7th Australian Peptide Conference and the 2nd Asia-Pacific International Peptide Symposium: New technologies to prolong life-time of peptide, protein and low-molecular-weight drugs in vivo. Wilce, J. (Ed.).
Supplementary European Search Report issued on Feb. 12, 2013 in connection with European Patent No. 10 744 058.8.
Apr. 11, 2013, Translation of First Office Action issued by the Chinese Patent Office in connection with Chinese application No. 201080016333.3.
Sep. 30, 2013 Communication pursuant to Article 94 (3) EPC issued by the European Patent Office in connection with European application No. 10 744 058.8.
Aug. 22, 2013 Response to Supplementary European Search Report issued on Feb. 12, 2013 in connection with European Patent No. 10 744 058.8.
Fine, Barry Michael "Analysis of PTEN function and regulation" Columbia University, Dissertation, Sep. 2008, AAT 3305221.
Fine, Barry Michael "Analysis of PTEN function and regulation" Columbia University, Dissertation, July 17, 2008, AAT 3305221.
Georgescu et al. Proc. Natl. Acad. Sci. U.S.A. (199) vol. 96, No. 18, p. 10182-10187.
Wu. et al. "Interaction of the tumor suppressor PTEN/MMAC with a PDZ domain of MAG13, a novel membrane-associated guanylate kinase." The Journal of Biological Chemistry Jul 14, 2000, vol. 275, No. 28, pp. 21477-21485, ISSN: 0021-9258.
Oct. 25, 2013 Response to Apr. 11, 2013 Office Action issued in connection with Chinese Patent Application No. 2010800163333 (including English translation of coverpage).
Nov. 26, 2013 Office Action issued in connection with Chinese Patent Application No. 2010800163333 (including English Language translation).
Apr. 11, 2014 Response to Nov. 26, 2013 Office Action issued in connection with Chinese Patent Application No. 2010800163333 (including English translation of coverpage).
Jun. 3, 2014 Office Action issued in connection with Chinese Patent Application No. 2010800163333 (including English translation of coverpage).
Apr. 10, 2014 Response to Sep. 30, 2013 Office Action issued in connection with European Patent Application No. 10744058.8.
May 22, 2014 Office Action issued in connection with European Patent Application No. 10744058.8.
Jun. 24, 2014 Office Action issued in connection with Japanese Patent Application No. 2011-551062 (including English Language translation).
Notification of Transmittal of the International Search Report and the Written Opinion of the International Searching Authority, or the Declaration, including an International Search Report and Written Opinion of the International Searching Authority, mailed. Jun. 15, 2011 in connection with PCT International Application No. PCT/US2011/025312, filed Feb. 17, 2011.
Feb. 19, 2014 Office Action issued in connection with U.S. Appl. No. 13/579,025.
Jul. 16, 2014 Response to Feb. 19, 2014 Office Action issued in connection with U.S. Appl. No. 13/579,025.
Jul. 25, 2014 Final Office Action issued in connection with U.S. Appl. No. 13/579,025.
Jul. 2, 2013 Office Action in connection with Chinese Application No. 201180018210.8 (with English Language translation).
Jan. 17, 2014 Response to the Jul. 2, 2013 Office Action in connection with Chinese Application No. 201180018210.8 (including English translation of coverpage).
Apr. 11, 2014 Second Office Action in connection with Chinese Application No. 201180018210.8 (with English Language translation).
Jun. 26, 2014 Response to the Apr. 11, 2014 Second Office Action in connection with Chinese Application No. 201180018210.8 (including English translation of coverpage).
Jul. 28, 2014 Third Office Action in connection with Chinese Application No. 201180018210.8 (with English Language translation).

* cited by examiner

Fig. 3

SEQUENCE LISTING

```
<160> NUMBER OF SEQ ID NOS: 7

<210> SEQ ID NO 1
<211> LENGTH: 576
<212> TYPE: PRT
<213> ORGANISM: Homo sapiens
<220> FEATURE:
<221> NAME/KEY: MISC_FEATURE
<222> LOCATION: (1)..(173)
<223> OTHER INFORMATION: PTEN-long specific protein sequence encoded by
      5' ATR starting at CUG start codon
<220> FEATURE:
<221> NAME/KEY: MISC_FEATURE
```

```
<222> LOCATION: (174)..(174)
<223> OTHER INFORMATION: Initiator Met of PTEN

<400> SEQUENCE: 1
```

| | | | | | | | | | | | | | | |
|---|---|---|---|---|---|---|---|---|---|---|---|---|---|---|
| Leu | Glu | Arg | Gly | Gly | Glu | Ala | Ala | Ala | Ala | Ala | Ala | Ala | Ala | Ala |
| 1 | | | | 5 | | | | | 10 | | | | | 15 |
| Ala | Pro | Gly | Arg | Gly | Ser | Glu | Ser | Pro | Val | Thr | Ile | Ser | Arg | Ala | Gly |
| | | | 20 | | | | | 25 | | | | | 30 | | |
| Asn | Ala | Gly | Glu | Leu | Val | Ser | Pro | Leu | Leu | Leu | Pro | Pro | Thr | Arg | Arg |
| | | 35 | | | | | 40 | | | | | 45 | | | |
| Arg | Arg | Arg | Arg | His | Ile | Gln | Gly | Pro | Gly | Pro | Val | Leu | Asn | Leu | Pro |
| | 50 | | | | | 55 | | | | | 60 | | | | |
| Ser | Ala | Ala | Ala | Pro | Pro | Val | Ala | Arg | Ala | Pro | Glu | Ala | Ala | Gly |
| 65 | | | | | 70 | | | | | 75 | | | | | 80 |
| Gly | Gly | Ser | Arg | Ser | Glu | Asp | Tyr | Ser | Ser | Pro | His | Ser | Ala | Ala |
| | | | | 85 | | | | | 90 | | | | | 95 |
| Ala | Ala | Ala | Arg | Pro | Leu | Ala | Ala | Glu | Glu | Lys | Gln | Ala | Gln | Ser | Leu |
| | | | 100 | | | | | 105 | | | | | 110 | | |
| Gln | Pro | Ser | Ser | Ser | Arg | Arg | Ser | Ser | His | Tyr | Pro | Ala | Ala | Val | Gln |
| | | 115 | | | | | 120 | | | | | 125 | | | |
| Ser | Gln | Ala | Ala | Ala | Glu | Arg | Gly | Ala | Ser | Ala | Thr | Ala | Lys | Ser | Arg |
| | 130 | | | | | 135 | | | | | 140 | | | | |
| Ala | Ile | Ser | Ile | Leu | Gln | Lys | Lys | Pro | Arg | His | Gln | Gln | Leu | Leu | Pro |
| 145 | | | | | 150 | | | | | 155 | | | | | 160 |
| Ser | Leu | Ser | Ser | Phe | Phe | Phe | Ser | His | Arg | Leu | Pro | Asp | Met | Thr | Ala |
| | | | | 165 | | | | | 170 | | | | | 175 | |
| Ile | Ile | Lys | Glu | Ile | Val | Ser | Arg | Asn | Lys | Arg | Arg | Tyr | Gln | Glu | Asp |
| | | | 180 | | | | | 185 | | | | | 190 | | |
| Gly | Phe | Asp | Leu | Asp | Leu | Thr | Tyr | Ile | Tyr | Pro | Asn | Ile | Ile | Ala | Met |
| | | 195 | | | | | 200 | | | | | 205 | | | |
| Gly | Phe | Pro | Ala | Glu | Arg | Leu | Glu | Gly | Val | Tyr | Arg | Asn | Asn | Ile | Asp |
| | 210 | | | | | 215 | | | | | 220 | | | | |
| Asp | Val | Val | Arg | Phe | Leu | Asp | Ser | Lys | His | Lys | Asn | His | Tyr | Lys | Ile |
| 225 | | | | | 230 | | | | | 235 | | | | | 240 |
| Tyr | Asn | Leu | Cys | Ala | Glu | Arg | His | Tyr | Asp | Thr | Ala | Lys | Phe | Asn | Cys |
| | | | | 245 | | | | | 250 | | | | | 255 | |
| Arg | Val | Ala | Gln | Tyr | Pro | Phe | Glu | Asp | His | Asn | Pro | Pro | Gln | Leu | Glu |
| | | | 260 | | | | | 265 | | | | | 270 | | |
| Leu | Ile | Lys | Pro | Phe | Cys | Glu | Asp | Leu | Asp | Gln | Trp | Leu | Ser | Glu | Asp |
| | | 275 | | | | | 280 | | | | | 285 | | | |
| Asp | Asn | His | Val | Ala | Ala | Ile | His | Cys | Lys | Ala | Gly | Lys | Gly | Arg | Thr |
| | 290 | | | | | 295 | | | | | 300 | | | | |
| Gly | Val | Met | Ile | Cys | Ala | Tyr | Leu | Leu | His | Arg | Gly | Lys | Phe | Leu | Lys |
| 305 | | | | | 310 | | | | | 315 | | | | | 320 |
| Ala | Gln | Glu | Ala | Leu | Asp | Phe | Tyr | Gly | Glu | Val | Arg | Thr | Arg | Asp | Lys |
| | | | | 325 | | | | | 330 | | | | | 335 | |
| Lys | Gly | Val | Thr | Ile | Pro | Ser | Gln | Arg | Arg | Tyr | Val | Tyr | Tyr | Tyr | Ser |
| | | | 340 | | | | | 345 | | | | | 350 | | |
| Tyr | Leu | Leu | Lys | Asn | His | Leu | Asp | Tyr | Arg | Pro | Val | Ala | Leu | Leu | Phe |
| | | 355 | | | | | 360 | | | | | 365 | | | |
| His | Lys | Met | Met | Phe | Glu | Thr | Ile | Pro | Met | Phe | Ser | Gly | Gly | Thr | Cys |
| | 370 | | | | | 375 | | | | | 380 | | | | |
| Asn | Pro | Gln | Phe | Val | Val | Cys | Gln | Leu | Lys | Val | Lys | Ile | Tyr | Ser | Ser |
| 385 | | | | | 390 | | | | | 395 | | | | | 400 |

```
Asn Ser Gly Pro Thr Arg Arg Glu Asp Lys Phe Met Tyr Phe Glu Phe
                405                 410                 415

Pro Gln Pro Leu Pro Val Cys Gly Asp Ile Lys Val Glu Phe Phe His
            420                 425                 430

Lys Gln Asn Lys Met Leu Lys Lys Asp Lys Met Phe His Phe Trp Val
        435                 440                 445

Asn Thr Phe Phe Ile Pro Gly Pro Glu Glu Thr Ser Glu Lys Val Glu
    450                 455                 460

Asn Gly Ser Leu Cys Asp Gln Glu Ile Asp Ser Ile Cys Ser Ile Glu
465                 470                 475                 480

Arg Ala Asp Asn Asp Lys Glu Tyr Leu Val Leu Thr Leu Thr Lys Asn
                485                 490                 495

Asp Leu Asp Lys Ala Asn Lys Asp Lys Ala Asn Arg Tyr Phe Ser Pro
            500                 505                 510

Asn Phe Lys Val Lys Leu Tyr Phe Thr Lys Thr Val Glu Glu Pro Ser
        515                 520                 525

Asn Pro Glu Ala Ser Ser Ser Thr Ser Val Thr Pro Asp Val Ser Asp
    530                 535                 540

Asn Glu Pro Asp His Tyr Arg Tyr Ser Asp Thr Thr Asp Ser Asp Pro
545                 550                 555                 560

Glu Asn Glu Pro Phe Asp Glu Asp Gln His Thr Gln Ile Thr Lys Val
                565                 570                 575

<210> SEQ ID NO 2
<211> LENGTH: 5572
<212> TYPE: RNA
<213> ORGANISM: Homo sapiens
<220> FEATURE:
<221> NAME/KEY: misc_feature
<222> LOCATION: (513)..(515)
<223> OTHER INFORMATION: CUG initiation codon of PTEN-long
<220> FEATURE:
<221> NAME/KEY: misc_feature
<222> LOCATION: (513)..(1031)
<223> OTHER INFORMATION: 5' ATR of PTEN-long
<220> FEATURE:
<221> NAME/KEY: misc_feature
<222> LOCATION: (1032)..(1034)
<223> OTHER INFORMATION: Canonical AUG initiation codon of PTEN

<400> SEQUENCE: 2 ccucccucg   cccggcgcgg   ucccguccgc   cucucgcucg   ccucccgccu   ccccucgguc      60
uuccgaggcg   cccgggcucc   cggcgcggcg   gcggaggggg   cggcaggcc   ggcgggcggu     120 gaugugcgg   gacucuuuau   gcgcugcggc   aggauacgcg   cucggcgcug   ggacgcgacu     180
gcgcucaguu   cucccucuc   ggaagcugca   gccaugaugg   aaguuugaga   guugagccgc     240
ugugaggcga   ggccgggcuc   aggcgaggga   gaugagagac   ggcggcggcc   gcggcccgga     300
gccccucuca   gcgccuguga   gcagccgcgg   gggcagcgcc   cucggggagc   cggccggccu     360
gcggcggcgg   cagcggcggc   guuucucgcc   uccucuucgu   cuuuucuaac   cgugcagccu     420 cuccucggc   uucuccugaa   agggaaggug   gaagccgugg   gcucgggcgg   gagccggcug     480
aggcgcggcg   gcgcggcgg   caccucccgc   uccuggagcg   gggggagaa   gcggcggcg     540 cggcggccgc   ggcggcugca   gcccaggga   ggggucuga   gucgccuguc   accauuucca     600
gggcugggaa   cgccggagag   uuggucucuc   cccuucuacu   gccuccaaca   cggcggcggc     660
ggcggcggca   cauccaggga   cccgggccgg   uuuuaaaccu   cccguccgcc   gccgccgcac     720 ccccgugcc   ccgggcuccg   gaggccgccg   gcggaggcag   ccguucggag   gauuauucgu     780
```

```
cuucucccca uuccgcugcc gccgcugcca ggccucuggc ugcugaggag aagcaggccc      840
agucgcugca accauccagc agccgccgca gcagccauua cccggcugcg guccagagcc      900
aagcggcggc agagcgaggg gcaucagcua ccgccaaguc cagagccauu uccauccugc      960
agaagaagcc ccgccaccag cagcuucugc caucucucuc cuccuuuuuc uucagccaca     1020
ggcucccaga caugacagcc aucaucaaag agaucguuag cagaaacaaa aggagauauc     1080
aagaggaugg auucgacuua gacuugaccu auauuuaucc aaacauuauu gcuaugggau     1140
uuccugcaga aagacuugaa ggcguauaca ggaacaauau ugaugaugua guaagguuuu     1200
uggauucaaa gcauaaaaac cauuacaaga uauacaaucu uugugcugaa agacauuaug     1260
acaccgccaa auuuaauugc agaguugcac aauauccuuu ugaagaccau aacccaccac     1320
agcuagaacu uaucaaaccc uuuugugaag aucuugacca auggcuaagu gaagaugaca     1380
aucauguugc agcaauucac uguaaagcug gaaagggacg aacuggugua augauaugug     1440
cauauuuauu acaucgggc aaauuuuuaa aggcacaaga ggcccuagau uucuaugggg      1500
aaguaaggac cagagacaaa aagggaguaa cuauucccag ucagaggcgc uauguguauu     1560
auuauagcua ccuguuaaag aaucaucugg auuauagacc aguggcacug uuguuucaca     1620
agaugauguu ugaaacuauu ccaauguuca guggcggaac uugcaauccu caguuugugg     1680
ucugccagcu aaaggugaag auauauuccu ccaauucagg acccacacga cgggaagaca     1740
aguucaugua cuuugaguuc cccagccgu uaccugugug uggugauauc aaaguagagu      1800
ucuuccacaa acagaacaag augcuaaaaa aggacaaaau guuucacuuu uggguaaaua     1860
cauucuucau accaggacca gaggaaaccu cagaaaaagu agaaaaugga agucuaugug     1920
aucaagaaau cgauagcauu ugcaguauag agcgugcaga uaugacaag gaauaucuag      1980 uacuuacuuu aacaaaaaau gaucuugaca agcaaauaa agacaaagcc aaccgauacu      2040
uuucuccaaa uuuuaaggug aagcuguacu ucacaaaaac aguagaggag ccgucaaauc     2100
cagaggcuag caguucaacu ucuguaacac cagauguuag ugacaaugaa ccugaucauu     2160
auagauauuc ugacaccacu gacucugauc cagagaauga accuuuugau gaagaucagc     2220
auacacaaau uacaaaaguc ugaauuuuuu uuuaucaaga gggauaaaac accaugaaaa     2280
uaaacuugaa uaaacugaaa auggaccuuu uuuuuuuaa uggcaauagg acauugcuc      2340 agauuaccag uuauaggaac aauucucuuu uccugaccaa ucuuguuuua cccuauacau     2400 ccacagggu uugacacuug uuguccaguu gaaaaaaggu uguguagcug ugucauguau      2460
auaccuuuuu gugucaaaag gacauuuaaa auucaauuag gauuaauaaa gauggcacuu     2520
ucccguuuua uuccaguuuu auaaaagug gagacagacu gaugucuaua cguaggaauu      2580
uuuuccuuuu guguucuguc accaacugaa gugggcuaaag agcuuguga uauacugguu     2640 cacauccuac cccuuugcac uugugcaac agauaaguuu gcaguuggcu aagagagguu      2700
uccgaagggu uuugcuacau ucuaaugcau guauucgggu uaggggaaug gagggaaugc     2760
ucagaaagga aauaauuuua ugcuggacuc uggaccauau accaucucca gcuauuuaca     2820
cacaccuuuc uuuagcaugc uacaguuauu aaucuggaca uucgaggaau uggccgcugu     2880
cacugcuugu uguugcgca uuuuuuuua agcauauug gugcuagaaa aggcagcuaa       2940
aggaagugaa ucuguauugg gguacaggaa ugaaccuucu gcaacaucuu aagauccaca     3000
aaugaaggga uauaaaaaua augucauagg uaagaaacac agcaacaaug acuuaaccau     3060
auaaaugugg aggcuaucaa caaagaaugg gcuugaaaca uuauaaaaau ugacaaugau     3120
```

-continued

```
uuauuaaaua uguuuucuca auuguaacga cuucuccauc uccuguguaa ucaaggccag    3180
ugcuaaaauu cagaugcugu uaguaccuac aucagucaac aacuuacacu uauuuuacua    3240
guuuucaauc auaauaccug cuguggaugc uucaugugcu gccugcaagc uucuuuuuuc    3300
ucauuaaaua uaaauauuu uguaaugcug cacagaaauu uucaauuuga gauucuacag     3360
uaagcguuuu uuucuuuga agauuuauga ugcacuuauu caauagcugu cagccguucc    3420
acccuuuuga ccuacacau ucuauuacaa ugaauuuugc aguuuugcac auuuuuaaa     3480
ugcauuaac uguuagggaa uuuuacuuga auacugaaua cauauaaugu uuauauuaaa     3540
aaggacauuu guguuaaaaa ggaaauuaga guugcaguaa acuuucaaug cugcacacaa    3600
aaaaaagaca uuugauuuuu caguagaaau ugccuacau gugcuuuauu gauuugcuau     3660
ugaaagaaua ggguuuuuuu uuuuuuuuuu uuuuuuuuuu uuaaaugugc aguguugaau    3720
cauucuuca uagugcuccc ccgaguuggg acuagggcuu caauuucacu ucuuaaaaaa    3780
aaucaucaua uauuugauau gcccagacug cauacgauuu uaagcggagu acaacuacua    3840
uuguaaagcu aaugugaaga uauuauuaaa aagguuuuu uuccagaaa uugggugucu      3900
ucaaauuaua ccuucacccuu gacauuugaa uauccagcca uuuuguuucu uaaugguaua    3960
aaauuccauu uucaauaacu uauuggugcu gaaauuguuc acuagcugug gucugaccua    4020
guuaauuuac aaauacagau ugaauaggac cuacuagagc agcauuuaua gaguuugaug    4080
gcaaauagau uaggcagaac uucaucuaaa auauucuuag uaaauaaugu ugacacguuu    4140
uccauaccuu gucaguuuca uucaacaauu uuuaaauuu uaacaaagcu cuuaggauuu     4200
acacauuuau auuuaaacau ugauauauag aguauugauu gauugcucau aaguuaaauu    4260
gguaaaguua gagacaacua uucuaacacc ucaccauuga aauuuauaug ccaccuuguc    4320
uuucauaaaa gcugaaaauu guuaccaaaa augaaaauca acuucauguu uugaagauag    4380
uuauaaauau uguucuuugu acaauuucg ggcaccgcau auuaaaacgu aacuuuauug     4440
uuccaauaug uaacauggag ggccagguca uaaauaauga cauuauaaug ggcuuuugca    4500
cuguuauuau uuuuccuuug gaaugugaag gucugaauga ggguuuugau uuugaaugu     4560
ucaauguuuu ugagaagccu ugcuuacauu uauggugua ucauggaa augaaaaau        4620
ggcauuauau auauuauaua uauaaauaua uauuauacau acucuccuua cuuuauuuca    4680
guuaccaucc ccauagaauu ugacaagaau ugcuaugacu gaaaggguuuu cgaguccuaa   4740
uuaaaacuuu auuuauggca guauucauaa uuagccugaa augcauucug uagguaaucu    4800
cugaguuucu ggaauauuu cuuagacuuu uggaugugc agcagcuuac augucugaag     4860
uuacuugaag gcaucacuuu uaagaaagcu uacaguuggg cccuguacca ucccaagucc    4920
uuugagcuc cucuugaaca uguuugccau acuuuuaaaa ggguaguuga auaaauagca    4980
ucaccauucu uugcugugc acagguuaua aacuuaagug gaguuuaccg gcagcaucaa     5040
auguuucagc uuuaaaaaau aaaaguaggg uacaaguuua auguuuuagu cuagaaauuu    5100
ugugcaauau guucauaacg auggcugugg uugccacaaa gugccucguu uaccuuuaaa    5160
uacuguuaau gugucaugca ugcagaugga aggguggaa cugugcacua aaguggggc      5220
uuuaacugua guauuggca gaguugccuu cuaccagcca guucaaaagu ucaaccuguu     5280
uucauauaga auauauauac uaaaaaauuu cagcucguua aacagccuua cucugauuca    5340
gcccucuucag auacucuugu gcugugcagc aguggcucug uguaaaug cuaugcacug     5400
aggauacaca aaaauaccaa uaugaugugu acaggauaau gccucauccc aaucagaugu    5460
ccauuuguua uugugulluugu uaacaacccu uuaucucuua guguuauaaa cuccacuuaa    5520
```

| | |
|---|---|
| aacugauuaa agucucauuc uugucaaaaa aaaaaaaaaa aaaaaaaaaa aa | 5572 |

<210> SEQ ID NO 3
<211> LENGTH: 5572
<212> TYPE: DNA
<213> ORGANISM: Homo sapiens
<220> FEATURE:
<221> NAME/KEY: misc_feature
<222> LOCATION: (513)..(515)
<223> OTHER INFORMATION: CTG initiation codon of PTEN-long
<220> FEATURE:
<221> NAME/KEY: misc_feature
<222> LOCATION: (513)..(1031)
<223> OTHER INFORMATION: 5' ATR of PTEN-long
<220> FEATURE:
<221> NAME/KEY: misc_feature
<222> LOCATION: (1032)..(1034)
<223> OTHER INFORMATION: Canonical ATG initiation codon of PTEN

<400> SEQUENCE: 3

| | |
|---|---|
| cctcccctcg cccggcgcgg tcccgtccgc ctctcgctcg cctcccgcct ccctcggtc | 60 |
| ttccgaggcg cccgggctcc cggcgcggcg gcggagggg cgggcaggcc ggcgggcggt | 120 |
| gatgtggcgg gactctttat gcgctgcggc aggatacgcg ctcggcgctg ggacgcgact | 180 |
| gcgctcagtt ctctcctctc ggaagctgca gccatgatgg aagtttgaga gttgagccgc | 240 |
| tgtgaggcga ggccgggctc aggcgaggga gatgagagac ggcggcggcc gcggcccgga | 300 |
| gccctctca gcgcctgtga gcagccgcgg gggcagcgcc ctcggggagc cggccggcct | 360 |
| gcggcggcgg cagcggcggc gtttctcgcc tcctcttcgt cttttctaac cgtgcagcct | 420 |
| cttcctcggc ttctcctgaa agggaaggtg gaagccgtgg gctcgggcgg gagccggctg | 480 |
| aggcgcggcg gcggcggcgg cacctcccgc tcctggagcg gggggagaa gcggcggcgg | 540 |
| cggcggccgc ggcggctgca gctccaggga gggggtctga gtcgcctgtc accatttcca | 600 |
| gggctgggaa cgccggagag ttggtctctc cccttctact gcctccaaca cggcggcggc | 660 |
| ggcggcggca catccaggga cccgggccgg ttttaaacct cccgtccgcc gccgccgcac | 720 |
| ccccgtggc ccgggctccg gaggccgccg gcggaggcag ccgttcggag gattattcgt | 780 |
| cttctcccca ttccgctgcc gccgctgcca ggcctctggc tgctgaggag aagcaggcc | 840 |
| agtcgctgca accatccagc agccgccgca gcagccatta cccggctgcg gtccagagcc | 900 |
| aagcggcggc agagcgaggg gcatcagcta ccgccaagtc cagagccatt tccatcctgc | 960 |
| agaagaagcc ccgccaccag cagcttctgc catctctctc ctccttttc ttcagccaca | 1020 |
| ggctcccaga catgacagcc atcatcaaag agatcgttag cagaaacaaa aggagatatc | 1080 |
| aagaggatgg attcgactta gacttgacct atatttatcc aaacattatt gctatgggat | 1140 |
| ttcctgcaga aagacttgaa ggcgtataca ggaacaatat tgatgatgta gtaaggtttt | 1200 |
| tggattcaaa gcataaaaac cattacaaga tatacaatct tgtgctgaa agacattatg | 1260 |
| acaccgccaa atttaattgc agagttgcac aatatccttt tgaagaccat aacccaccac | 1320 |
| agctagaact tatcaaaccc ttttgtgaag atcttgacca atggctaagt gaagatgaca | 1380 |
| atcatgttgc agcaattcac tgtaaagctg gaaagggacg aactggtgta atgatatgtg | 1440 |
| catatttatt acatcggggc aaattttta aggcacaaga ggccctagat ttctatgggg | 1500 |
| aagtaaggac cagagacaaa aagggagtaa ctattcccag tcagaggcgc tatgtgtatt | 1560 |
| attatagcta cctgttaaag aatcatctgg attatagacc agtggcactg ttgtttcaca | 1620 |
| agatgatgtt tgaaactatt ccaatgttca gtggcggaac ttgcaatcct cagtttgtgg | 1680 |

```
tctgccagct aaaggtgaag atatattcct ccaattcagg acccacacga cgggaagaca    1740
agttcatgta ctttgagttc cctcagccgt tacctgtgtg tggtgatatc aaagtagagt    1800
tcttccacaa acagaacaag atgctaaaaa aggacaaaat gtttcacttt tgggtaaata    1860
cattcttcat accaggacca gaggaaacct cagaaaaagt agaaaatgga agtctatgtg    1920
atcaagaaat cgatagcatt tgcagtatag agcgtgcaga taatgacaag gaatatctag    1980
tacttacttt aacaaaaaat gatcttgaca aagcaaataa agacaaagcc aaccgatact    2040
tttctccaaa ttttaaggtg aagctgtact tcacaaaaac agtagaggag ccgtcaaatc    2100
cagaggctag cagttcaact tctgtaacac cagatgttag tgacaatgaa cctgatcatt    2160
atagatattc tgacaccact gactctgatc cagagaatga acctttttgat gaagatcagc    2220 atacacaaat tacaaaagtc tgaattttt tttatcaaga gggataaaac accatgaaaa    2280
taaacttgaa taaactgaaa atggaccttt ttttttttaa tggcaatagg acattgtgtc    2340
agattaccag ttataggaac aattctcttt tcctgaccaa tcttgtttta ccctatacat    2400
ccacagggtt ttgacacttg ttgtccagtt gaaaaaggt tgtgtagctg tgtcatgtat    2460 atacctttt gtgtcaaaag gacatttaaa attcaattag gattaataaa gatggcactt    2520
tcccgtttta ttccagtttt ataaaagtg gagacagact gatgtgtata cgtaggaatt    2580 ttttccttt gtgttctgtc accaactgaa gtggctaaag gctttgtga tatactggtt    2640 cacatcctac cccttttgcac ttgtggcaac agataagttt gcagttggct aagagaggtt    2700
tccgaagggt tttgctacat tctaatgcat gtattcgggt tagggaatg gagggaatgc    2760 tcagaaagga aataattttta tgctggactc tggaccatat accatctcca gctatttaca    2820
cacacctttc tttagcatgc tacagttatt aatctggaca ttcgaggaat tggccgctgt    2880
cactgcttgt tgtttgcgca tttttttta aagcatattg gtgctagaaa aggcagctaa    2940
aggaagtgaa tctgtattgg ggtacaggaa tgaaccttct gcaacatctt aagatccaca    3000
aatgaaggga tataaaaata atgtcatagg taagaaacac agcaacaatg acttaaccat    3060
ataaatgtgg aggctatcaa caaagaatgg gcttgaaaca ttataaaaat tgacaatgat    3120
ttattaaata tgttttctca attgtaacga cttctccatc tcctgtgtaa tcaaggccag    3180
tgctaaaatt cagatgctgt tagtacctac atcagtcaac aacttacact tatttacta    3240 gttttcaatc ataatacctg ctgtggatgc ttcatgtgct gcctgcaagc ttcttttttc    3300
tcattaaata taaaatattt tgtaatgctg cacagaaatt ttcaatttga gattctacag    3360
taagcgtttt ttttctttga agatttatga tgcacttatt caatagctgt cagccgttcc    3420
acccttttga ccttacacat tctattacaa tgaattttgc agttttgcac atttttttaaa   3480 tgtcattaac tgttagggaa ttttacttga atactgaata catataatgt ttatattaaa    3540
aaggacattt gtgttaaaaa ggaaattaga gttgcagtaa actttcaatg ctgcacacaa    3600 aaaaagaca tttgattttt cagtagaaat tgtcctacat gtgctttatt gatttgctat    3660
tgaaagaata gggtttttt tttttttttt ttttttttt ttaaatgtgc agtgttgaat    3720
catttcttca tagtgctccc ccgagttggg actagggctt caatttcact tcttaaaaaa    3780
aatcatcata tatttgatat gcccagactg catacgattt taagcggagt acaactacta    3840
ttgtaaagct aatgtgaaga tattattaaa aaggtttttt tttccagaaa tttggtgtct    3900
tcaaattata ccttcacctt gacatttgaa tatccagcca ttttgttct taatggtata    3960 aaattccatt ttcaataact tattggtgct gaaattgttc actagctgtg gtctgaccta    4020
gttaatttac aaatacagat tgaataggac ctactagagc agcatttata gagtttgatg    4080
```

```
gcaaatagat taggcagaac ttcatctaaa atattcttag taaataatgt tgacacgttt    4140
tccatacctt gtcagtttca ttcaacaatt tttaaatttt taacaaagct cttaggattt    4200
acacatttat atttaaacat tgatatatag agtattgatt gattgctcat aagttaaatt    4260
ggtaaagtta gagacaacta ttctaacacc tcaccattga aatttatatg ccaccttgtc    4320
tttcataaaa gctgaaaatt gttacctaaa atgaaaatca acttcatgtt ttgaagatag    4380
ttataaatat tgttctttgt tacaatttcg ggcaccgcat attaaaacgt aactttattg    4440
ttccaatatg taacatggag ggccaggtca taaataatga cattataatg ggcttttgca    4500
ctgttattat ttttcctttg gaatgtgaag gtctgaatga gggttttgat tttgaatgtt    4560
tcaatgtttt tgagaagcct tgcttacatt ttatggtgta gtcattggaa atggaaaaat    4620
ggcattatat atattatata tataaatata tattatacat actctcctta ctttatttca    4680
gttaccatcc ccatagaatt tgacaagaat tgctatgact gaaaggtttt cgagtcctaa    4740
ttaaaacttt atttatggca gtattcataa ttagcctgaa atgcattctg taggtaatct    4800
ctgagtttct ggaatatttt cttagacttt ttggatgtgc agcagcttac atgtctgaag    4860
ttacttgaag gcatcacttt taagaaagct tacagttggg ccctgtacca tcccaagtcc    4920
tttgtagctc ctcttgaaca tgtttgccat acttttaaaa gggtagttga ataaatagca    4980
tcaccattct ttgctgtggc acaggttata aacttaagtg gagttaccg gcagcatcaa     5040 atgtttcagc tttaaaaaat aaaagtaggg tacaagttta atgtttagtt ctagaaattt    5100
tgtgcaatat gttcataacg atggctgtgg ttgccacaaa gtgcctcgtt tacctttaaa    5160
tactgttaat gtgtcatgca tgcagatgga aggggtggaa ctgtgcacta aagtgggggc    5220
tttaactgta gtatttggca gagttgcctt ctacctgcca gttcaaaagt tcaacctgtt    5280
ttcatataga atatatatac taaaaaattt cagtctgtta aacagcctta ctctgattca    5340
gcctcttcag atactcttgt gctgtgcagc agtggctctg tgtgtaaatg ctatgcactg    5400
aggatacaca aaaataccaa tatgatgtgt acaggataat gcctcatccc aatcagatgt    5460
ccatttgtta ttgtgtttgt taacaaccct ttatctctta gtgttataaa ctccacttaa    5520
aactgattaa agtctcattc ttgtcaaaaa aaaaaaaaa aaaaaaaaaa aa              5572
```

<210> SEQ ID NO 4
<211> LENGTH: 21
<212> TYPE: PRT
<213> ORGANISM: Homo sapiens

<400> SEQUENCE: 4

Pro Arg His Gln Gln Leu Leu Pro Ser Leu Ser Ser Phe Phe Phe Ser
1               5                   10                  15

His Arg Leu Pro Asp
            20

<210> SEQ ID NO 5
<211> LENGTH: 576
<212> TYPE: PRT
<213> ORGANISM: Homo sapiens
<220> FEATURE:
<221> NAME/KEY: MISC_FEATURE
<222> LOCATION: (1)..(173)
<223> OTHER INFORMATION: PTEN-long analogue protein sequence encoded
      by 5' ATR starting at engineered AUG start codon

<400> SEQUENCE: 5

Met Glu Arg Gly Gly Glu Ala Ala Ala Ala Ala Ala Ala Ala Ala Ala

-continued

```
1               5                   10                  15
Ala Pro Gly Arg Gly Ser Glu Ser Pro Val Thr Ile Ser Arg Ala Gly
                20                  25                  30

Asn Ala Gly Glu Leu Val Ser Pro Leu Leu Pro Pro Thr Arg Arg
                35                  40                  45

Arg Arg Arg His Ile Gln Gly Pro Gly Pro Val Leu Asn Leu Pro
    50                  55                  60

Ser Ala Ala Ala Pro Pro Val Ala Arg Ala Pro Glu Ala Ala Gly
65                  70                  75                  80

Gly Gly Ser Arg Ser Glu Asp Tyr Ser Ser Pro His Ser Ala Ala
                85                  90                  95

Ala Ala Ala Arg Pro Leu Ala Ala Glu Glu Lys Gln Ala Gln Ser Leu
                100                 105                 110

Gln Pro Ser Ser Ser Arg Arg Ser Ser His Tyr Pro Ala Ala Val Gln
                115                 120                 125

Ser Gln Ala Ala Ala Glu Arg Gly Ala Ser Ala Thr Ala Lys Ser Arg
130                 135                 140

Ala Ile Ser Ile Leu Gln Lys Lys Pro Arg His Gln Gln Leu Leu Pro
145                 150                 155                 160

Ser Leu Ser Ser Phe Phe Ser His Arg Leu Pro Asp Met Thr Ala
                165                 170                 175

Ile Ile Lys Glu Ile Val Ser Arg Asn Lys Arg Arg Tyr Gln Glu Asp
                180                 185                 190

Gly Phe Asp Leu Asp Leu Thr Tyr Ile Tyr Pro Asn Ile Ile Ala Met
                195                 200                 205

Gly Phe Pro Ala Glu Arg Leu Glu Gly Val Tyr Arg Asn Asn Ile Asp
    210                 215                 220

Asp Val Val Arg Phe Leu Asp Ser Lys His Lys Asn His Tyr Lys Ile
225                 230                 235                 240

Tyr Asn Leu Cys Ala Glu Arg His Tyr Asp Thr Ala Lys Phe Asn Cys
                245                 250                 255

Arg Val Ala Gln Tyr Pro Phe Glu Asp His Asn Pro Pro Gln Leu Glu
                260                 265                 270

Leu Ile Lys Pro Phe Cys Glu Asp Leu Asp Gln Trp Leu Ser Glu Asp
                275                 280                 285

Asp Asn His Val Ala Ala Ile His Cys Lys Ala Gly Lys Gly Arg Thr
                290                 295                 300

Gly Val Met Ile Cys Ala Tyr Leu Leu His Arg Gly Lys Phe Leu Lys
305                 310                 315                 320

Ala Gln Glu Ala Leu Asp Phe Tyr Gly Glu Val Arg Thr Arg Asp Lys
                325                 330                 335

Lys Gly Val Thr Ile Pro Ser Gln Arg Arg Tyr Val Tyr Tyr Ser
                340                 345                 350

Tyr Leu Leu Lys Asn His Leu Asp Tyr Arg Pro Val Ala Leu Leu Phe
                355                 360                 365

His Lys Met Met Phe Glu Thr Ile Pro Met Phe Ser Gly Gly Thr Cys
                370                 375                 380

Asn Pro Gln Phe Val Val Cys Gln Leu Lys Val Lys Ile Tyr Ser Ser
385                 390                 395                 400

Asn Ser Gly Pro Thr Arg Arg Glu Asp Lys Phe Met Tyr Phe Glu Phe
                405                 410                 415

Pro Gln Pro Leu Pro Val Cys Gly Asp Ile Lys Val Glu Phe Phe His
                420                 425                 430
```

```
            Lys Gln Asn Lys Met Leu Lys Lys Asp Lys Met Phe His Phe Trp Val
                        435                 440                 445

Asn Thr Phe Phe Ile Pro Gly Pro Glu Glu Thr Ser Glu Lys Val Glu
                    450                 455                 460

Asn Gly Ser Leu Cys Asp Gln Glu Ile Asp Ser Ile Cys Ser Ile Glu
            465                 470                 475                 480

Arg Ala Asp Asn Asp Lys Glu Tyr Leu Val Leu Thr Leu Thr Lys Asn
                            485                 490                 495

Asp Leu Asp Lys Ala Asn Lys Asp Lys Ala Asn Arg Tyr Phe Ser Pro
                        500                 505                 510

Asn Phe Lys Val Lys Leu Tyr Phe Thr Lys Thr Val Glu Glu Pro Ser
                    515                 520                 525

Asn Pro Glu Ala Ser Ser Ser Thr Ser Val Pro Asp Val Ser Asp
                530                 535                 540

Asn Glu Pro Asp His Tyr Arg Tyr Ser Asp Thr Asp Ser Asp Pro
            545                 550                 555                 560

Glu Asn Glu Pro Phe Asp Glu Asp Gln His Thr Gln Ile Thr Lys Val
                            565                 570                 575

<210> SEQ ID NO 6
<211> LENGTH: 5572
<212> TYPE: RNA
<213> ORGANISM: Homo sapiens
<220> FEATURE:
<221> NAME/KEY: misc_feature
<222> LOCATION: (513)..(515)
<223> OTHER INFORMATION: Engineered AUG initiation codon of PTEN-long
      analogue

<400> SEQUENCE: 6 ccucccucg    cccggcgcgg    ucccguccgc    cucucgcucg    ccucccgccu    ccccucgguc         60
uuccgaggcg   cccgggcucc    cggcgcggcg    gcggaggggg    cggcaggcc     ggcgggcggu        120 gauguggcgg   gacucuuuau    gcgcugcggc    aggauacgcg    cucggcgcug    ggacgcgacu        180
gcgcucaguu   cucccucuc     ggaagcugca    gccaugaugg    aaguuugaga    guugagccgc        240
ugugaggcga   ggccgggcuc    aggcgaggga    gaugagagac    ggcggcggcc    gcggcccgga        300
gccccucuca   gcgccugcga    gcagccgcgg    gggcagcgcc    ucggggagc     cggccggccu        360 gcggcggcgg   cagcggcggc    guuucucgcc    uccucuucgu    cuuuucuaac    cgugcagccu        420
cuuccucggc   uucuccugaa    agggaaggug    gaagccgugg    gcucgggcgg    gagccggcug        480
aggcgcggcg   gcggcggcgg    caccucccgc    ucauggagcg    gggggggagaa   gcggcggcgg        540 cggcggccgc   ggcggcugca    gcuccaggga    ggggucuga    ucgccuguc     accauuucca        600 gggcugggaa   cgccggagag    uuggucucuc    cccuucuacu    gccucaaca     cggcggcggc        660 ggcggcggca   cauccaggga    cccgggccgg    uuuuaaaccu    cccguccgcc    gccgccgcac        720 ccccgugcc    ccgggcuccg    gaggccgccg    gcggaggcag    ccguucggag    gauuauucgu        780 cuucuccca    uuccgcugcc    gccgcugcca    ggccucuggc    ugcugaggag    aagcaggccc        840
agucgcugca   accauccagc    agccgccgca    gcagccauua    cccggcugcg    guccagagcc        900
aagcggcggc   agagcgaggg    gcaucagcua    ccgccaaguc    cagagccauu    uccauccugc        960
agaagaagcc   ccgccaccag    cagcuucugc    caucucucuc    cuccuuuuuc    uucagccaca       1020
ggcucccaga   caugacagcc    aucaucaaag    agaucguuag    cagaaacaaa    aggagauauc       1080
aagaggaugg   auucgacuua    gacuugaccu    auauuuaucc    aaacauuauu    gcuaugggau       1140
```

```
uuccugcaga aagacuugaa ggcguauaca ggaacaauau ugaugaugua guaagguuuu    1200
uggauucaaa gcauaaaaac cauuacaaga uauacaaucu uugugcugaa agacauuaug    1260
acaccgccaa auuuaauugc agaguugcac aauauccuuu ugaagaccau aacccaccac    1320
agcuagaacu uaucaaaccc uuuugugaag aucuugacca auggcuaagu gaagaugaca    1380
aucauguugc agcaauucac uguaaagcug gaaagggacg aacuggugua augauaugug    1440
cauauuuauu acaucgggc aaauuuuuaa aggcacaaga ggcccuagau uucuaugggg    1500
aaguaaggac cagagacaaa aagggaguaa cuauucccag ucagaggcgc uauguguauu    1560
auuauagcua ccuguuaaag aaucaucugg auuauagacc aguggcacug uuguuucaca    1620
agaugauguu ugaaacuauu ccaauguuca guggcggaac uugcaauccu caguuugugg    1680
ucugccagcu aaaggugaag auauauuccu ccaauucagg acccacacga cgggaagaca    1740
aguucaugua cuuugaguuc ccucagccgu uaccugugug uggugauauc aaaguagagu    1800
ucuuccacaa acagaacaag augcuaaaaa aggacaaaau guuucacuuu uggguaaaua    1860
cauucuucau accaggacca gaggaaaccu cagaaaaagu agaaaaugga agucuaugug    1920
aucaagaaau cgauagcauu ugcaguauag agcgugcaga uaaugacaag gaauaucuag    1980
uacuuacuuu aacaaaaaau gaucuugaca agcaaauaa agacaaagcc aaccgauacu    2040
uuucuccaaa uuuuaaggug aagcuguacu ucacaaaaac aguagaggag ccgucaaauc    2100
cagaggcuag caguucaacu ucuguaacac cagauguuua ugcaaugaa ccugaucauu    2160 auagauauuc ugacaccacu gacucugauc cagagaauga accuuuugau gaagaucagc    2220
auacacaaau uacaaaaguc ugaauuuuuu uuaucaaga gggauaaaac accaugaaaa    2280
uaaacuugaa uaaacugaaa auggaccuuu uuuuuuuaa uggcaauagg acauugguc    2340 agauuaccag uuuauaggaac aauucucuuu uccugaccaa ucuuguuua cccuauacau    2400 ccacaggguu uugacacuug uuguccaguu gaaaaaaggu uguguagcug ugucauguau    2460
auaccuuuuu gugucaaaag gacauuuaaa auucaauuag gauuaauaaa gauggcacuu    2520
ucccguuuua uuccaguuuu auaaaaagug gagacagacu gauguguaua cguaggaauu    2580
uuuuccuuuu uguucugucc accaacugaa guggcuaaag agcuuuguga uauacugguu    2640
cacauccuac cccuuugcac uuguggcaac agauaaguuu gcaguuggcu aagagagguu    2700
uccgaagggu uuugcuacau ucuaaugcau guauucgggu uaggggaaug gagggaaugc    2760
ucagaaagga aauaauuuua ugcuggacuc uggaccauau accaucucca gcuauuuaca    2820
cacaccuuuc uuuagcaugc uacaguuauu aaucuggaca uucgaggaau uggccgcugu    2880
cacugcuugu uguugcgca uuuuuuuua aagcauauug gugcuagaaa aggcagcuaa    2940
aggaagugaa ucuguauugg gguacaggaa ugaaccuucu gcaacaucuu aagauccaca    3000
aaugaaggga uauaaaaaua augucauagg uaagaaacac agcaacaaug acuuaaccau    3060
auaaaugugg aggcuaucaa caaagaaugg gcuugaaaca uuauaaaaau ugacaaugau    3120
uuauuaaaua uguuuucuca auuguaacga cuucuccauc uccuguguaa ucaaggccag    3180
ugcuaaaauu cagaugcugu uaguaccuac aucagucaac aacuuacacu uauuuuacua    3240
guuuucaauc auaauaccug cuguggaugc uucaugugcu gccugcaagc uucuuuuuuc    3300
ucauuaaaua uaaaauauuu uguaaugcug cacagaaauu uucaauuuga gauucuacag    3360
uaagcguuuu uuuucuuuga agauuuauga ugcacuauu caauagcugu cagccguucc    3420
acccuuuuga ccuuacacau ucuauuacaa ugaauuuugc aguuugcac auuuuuuaaa    3480 ugucauuaac uguuagggaa uuuuacuuga auacugaaua cauauaaugu uuauauuaaa    3540
```

```
aaggacauuu guguuaaaaa ggaaauuaga guugcaguaa acuuucaaug cugcacacaa    3600
aaaaaagaca uuugauuuuu caguagaaau uguccuacau gugcuuuauu gauuugcuau    3660
ugaaagaaua ggguuuuuuu uuuuuuuuuu uuuuuuuuuu uuaaaugugc aguguugaau    3720
cauuucuuca uagugcuccc ccgaguuggg acuagggcuu caauuucacu cuuaaaaaa     3780 aaucaucaua uauuugauau gcccagacug caucgauuu uaagcggagu acaacuacua     3840
uuguaaagcu aaugugaaga uauuauaaa aagguuuuu uuccagaaa uuggugucu        3900 ucaaauuaua ccuucaccuu gacauuugaa uaccagcca uuuguuucu uaaugguaua      3960 aaauuccauu uucaauaacu uauuggcu gaaauguuc acuagcugug gucugaccua       4020
guuaauuuac aaauacagau ugaauaggac cuacuagagc agcauuuaua gaguuugaug    4080
gcaaauagau uaggcagaac uucaucuaaa auauucuuag uaaauaaugu ugacacguuu    4140
uccauaccuu gucaguuuca uucaacaauu uuuaaauuuu uaacaaagcu cuuaggauuu    4200
acacauuuau auuuaaacau ugauauauag aguauugauu gauugcucau aaguuaaauu    4260
gguaaaguua gagacaacua uucuaacacc ucaccauuga aauuuauaug ccaccuuguc    4320
uuucauaaaa gcugaaaauu guuaccaaaa augaaaauca acuucauguu uugaagauag    4380
uuauaaauau uguucuuugu uacaauuucg ggcaccgcau auuaaaacgu aacuuuauug    4440
uuccaauaug uaacauggag ggccagguca uaaauaauga cauuauaaug ggcuuuugca    4500
cuguuauuau uuuuccuuug gaaugugaag gucugaauga ggguuuugau uuugaauguu    4560
ucaauguuuu ugagaagccu ugcuuacauu uauggugua gucauuggaa augggaaaaau   4620 ggcauuauau auauuauaua uauaaauaua uauuauacau acucuccuua cuuuauuuca    4680
guuaccaucc ccauagaauu ugacaagaau ugcuagacu gaaagguuuu cgaguccuaa     4740
uuaaaacuuu auuuauggca guauucauaa uuagccugaa augcauucug uagguaaucu    4800
cugaguuucu ggaauauuuu cuuagacuuu ugggaugugc agcagcuuac augucugaag    4860
uuacuugaag gcaucacuuu uaagaaagcu uacaguuggg cccuguacca ucccaagucc    4920
uuuguagcuc cucuugaaca uguuugccau acuuuuaaaa ggguaguuga auaaauagca    4980
ucaccauucu uugcugugc acagguuaua aacuuaagug gaguuuaccg gcagcaucaa     5040
auguuucagc uuuaaaaaau aaaaguaggg uacaaguuua auguuuaguu cuagaaauuu    5100
ugugcaauau guucauaacg auggcugugg uugccacaaa gugccucguu uaccuuuaaa    5160
uacuguuaau gugucaugca ugcagaugga aggguggaa cugugcacua aaguggggc      5220 uuuaacugua guauuggca gaguugccuu cuaccagcca guucaaaagu caaccuguu      5280 uucauauaga auauauauac uaaaaaauuu cagucuguua aacagccuua cucugauuca    5340
gccucuucag auacucuugu gcugugcagc aguggcucug uguuaaaaug cuaugcacug    5400
aggauacaca aaaauaccaa uaugaugugu acaggauaau gccucauccc aaucagaugu    5460
ccauuuguua uuguguuugu uaacaacccu uuaucucuua guguuauaaa cuccacuuaa    5520
aacugauuaa agucucauuc uugucaaaaa aaaaaaaaa aaaaaaaaaa aa             5572
```

<210> SEQ ID NO 7
<211> LENGTH: 5572
<212> TYPE: DNA
<213> ORGANISM: Homo sapiens
<220> FEATURE:
<221> NAME/KEY: misc_feature
<222> LOCATION: (513)..(515)
<223> OTHER INFORMATION: Engineered AUG initiation codon of PTEN-long
    analogue

<400> SEQUENCE: 7

```
cctcccctcg cccggcgcgg tcccgtccgc ctctcgctcg cctcccgcct ccctcggtc       60
ttccgaggcg cccgggctcc cggcgcggcg gcggaggggg cggcaggcc ggcgggcggt      120
gatgtggcgg gactctttat gcgctgcggc aggatacgcg ctcggcgctg ggacgcgact    180
gcgctcagtt ctctcctctc ggaagctgca gccatgatgg aagtttgaga gttgagccgc    240
tgtgaggcga ggccgggctc aggcgaggga gatgagagac ggcggcggcc gcggcccgga    300
gcccctctca gcgcctgtga gcagccgcgg gggcagcgcc ctcggggagc cggccggcct    360
gcggcggcgc cagcggcggc gtttctcgcc tcctcttcgt cttttctaac cgtgcagcct    420
cttcctcggc ttctcctgaa agggaaggtg gaagccgtgg gctcgggcgg gagccggctg    480
aggcgcggcg gcgcggcgg cacctcccgc tcatggagcg gggggagaa gcggcggcgg    540
cggcggccgc ggcggctgca gctccaggga gggggtctga gtcgcctgtc accatttcca    600
gggctgggaa cgccggagag ttggtctctc cccttctact gcctccaaca cggcggcggc    660
ggcggcggca catccaggga cccgggccgg ttttaaacct cccgtccgcc gccgccgcac    720
cccccgtggc ccgggctccg gaggccgccg gcggaggcag ccgttcggag gattattcgt    780
cttctcccca ttccgctgcc gccgctgcca ggcctctggc tgctgaggag aagcaggccc    840
agtcgctgca accatccagc agccgccgca gcagccatta cccggctgcg gtccagagcc    900
aagcggcggc agagcgaggg gcatcagcta ccgccaagtc cagagccatt tccatcctgc    960
agaagaagcc ccgccaccag cagcttctgc catctctctc ctcctttttc ttcagccaca   1020
ggctcccaga catgacagcc atcatcaaag agatcgttag cagaaacaaa aggagatatc   1080
aagaggatgg attcgactta gacttgacct atatttatcc aaacattatt gctatgggat   1140
ttcctgcaga aagacttgaa ggcgtataca ggaacaatat tgatgatgta gtaaggtttt   1200
tggattcaaa gcataaaaac cattacaaga tatacaatct ttgtgctgaa agacattatg   1260
acaccgccaa atttaattgc agagttgcac aatatccttt tgaagaccat aacccaccac   1320
agctagaact tatcaaaccc ttttgtgaag atcttgacca atggctaagt gaagatgaca   1380
atcatgttgc agcaattcac tgtaaagctg gaaagggacg aactggtgta atgatatgtg   1440
catatttatt acatcggggc aaattttttaa aggcacaaga ggccctagat ttctatgggg   1500
aagtaaggac cagagacaaa aagggagtaa ctattcccag tcagaggcgc tatgtgtatt   1560
attatagcta cctgttaaag aatcatctgg attatagacc agtggcactg ttgtttcaca   1620
agatgatgtt tgaaactatt ccaatgttca gtggcggaac ttgcaatcct cagtttgtgg   1680
tctgccagct aaaggtgaag atatattcct ccaattcagg acccacacga cgggaagaca   1740
agttcatgta ctttgagttc cctcagccgt tacctgtgtg tggtgatatc aaagtagagt   1800
tcttccacaa acagaacaag atgctaaaaa aggacaaaat gtttcacttt tgggtaaata   1860
cattcttcat accaggacca gaggaaacct cagaaaagt agaaaatgga agtctatgtg   1920
atcaagaaat cgatagcatt tgcagtatag agcgtgcaga taatgacaag gaatatctag   1980
tacttacttt aacaaaaaat gatcttgaca aagcaaataa agacaaagcc aaccgatact   2040
tttctccaaa ttttaaggtg aagctgtact tcacaaaaac agtagaggag ccgtcaaatc   2100
cagaggctag cagttcaact tctgtaacac cagatgttag tgacaatgaa cctgatcatt   2160
atagatattc tgacaccact gactctgatc cagagaatga accttttgat gaagatcagc   2220
atacacaaat tacaaaagtc tgaatttttt tttatcaaga gggataaaac accatgaaaa   2280
```

```
taaacttgaa taaactgaaa atggaccttt ttttttttaa tggcaatagg acattgtgtc    2340
agattaccag ttataggaac aattctcttt tcctgaccaa tcttgtttta ccctatacat    2400
ccacagggtt ttgacacttg ttgtccagtt gaaaaaaggt tgtgtagctg tgtcatgtat    2460
ataccttttt gtgtcaaaag gacatttaaa attcaattag gattaataaa gatggcactt    2520
tcccgtttta ttccagtttt ataaaaagtg gagacagact gatgtgtata cgtaggaatt    2580
ttttcctttt gtgttctgtc accaactgaa gtggctaaag agctttgtga tatactggtt    2640
cacatcctac ccctttgcac ttgtggcaac agataagttt gcagttggct aagagaggtt    2700
tccgaagggt tttgctacat tctaatgcat gtattcgggt taggggaatg gagggaatgc    2760
tcagaaagga ataaattta tgctggactc tggaccatat accatctcca gctatttaca     2820
cacacctttc tttagcatgc tacagttatt aatctggaca ttcgaggaat tggccgctgt    2880
cactgcttgt tgtttgcgca tttttttta aagcatattg gtgctagaaa aggcagctaa     2940
aggaagtgaa tctgtattgg ggtacaggaa tgaaccttct gcaacatctt aagatccaca    3000
aatgaaggga tataaaaata atgtcatagg taagaaacac agcaacaatg acttaaccat    3060
ataaatgtgg aggctatcaa caaagaatgg gcttgaaaca ttataaaaat tgacaatgat    3120
ttattaaata tgttttctca attgtaacga cttctccatc tcctgtgtaa tcaaggccag    3180
tgctaaaatt cagatgctgt tagtacctac atcagtcaac aacttacact tattttacta    3240
gttttcaatc ataatcctg ctgtggatgc ttcatgtgct gcctgcaagc ttctttttc      3300 tcattaaata taaatatttt tgtaatgctg cacagaaatt ttcaatttga gattctacag    3360
taagcgtttt ttttctttga agatttatga tgcacttatt caatagctgt cagccgttcc    3420
acccttttga ccttacacat tctattacaa tgaattttgc agttttgcac atttttaaa     3480 tgtcattaac tgttagggaa ttttacttga atactgaata catataatgt ttatattaaa    3540
aaggacattt gtgttaaaaa ggaaattaga gttgcagtaa actttcaatg ctgcacacaa    3600
aaaaaagaca tttgattttt cagtagaaat tgtcctacat gtgctttatt gatttgctat    3660
tgaaagaata gggttttttt tttttttttt tttttttttt ttaaatgtgc agtgttgaat    3720
catttcttca tagtgctccc ccgagttggg actagggctt caatttcact tcttaaaaaa    3780
aatcatcata tatttgatat gcccagactg catacgattt taagcggagt acaactacta    3840
ttgtaaagct aatgtgaaga tattattaaa aaggtttttt tttccagaaa tttggtgtct    3900
tcaaattata ccttcacctt gacatttgaa tatccagcca ttttgtttct taatggtata    3960
aaattccatt tcaataact tattggtgct gaaattgttc actagctgtg gtctgaccta     4020
gttaatttac aaatacagat tgaataggac ctactagagc agcatttata gagtttgatg    4080
gcaaatagat taggcagaac ttcatctaaa atattcttag taaataatgt tgacacgttt    4140 tccataccctt gtcagtttca ttcaacaatt tttaaatttt taacaaagct cttaggattt    4200
acacatttat atttaaacat tgatatatag agtattgatt gattgctcat aagttaaatt    4260
ggtaaagtta gagacaacta ttctaacacc tcaccattga aatttatatg ccaccttgtc    4320
tttcataaaa gctgaaaatt gttacctaaa atgaaaatca acttcatgtt ttgaagatag    4380
ttataaatat tgttctttgt tacaatttcg ggcaccgcat attaaaacgt aactttattg    4440
ttccaatatg taacatggag ggccaggtca taaataatga cattataatg ggcttttgca    4500
ctgttattat ttttccttg gaatgtgaag gtctgaatga gggttttgat tttgaatgtt     4560
tcaatgtttt tgagaagcct tgcttacatt ttatggtgta gtcattggaa atggaaaaat    4620
ggcattatat atattatata tataaatata tattatacat actctcctta ctttatttca    4680
```

```
gttaccatcc ccatagaatt tgacaagaat tgctatgact gaaaggtttt cgagtcctaa    4740
ttaaaacttt atttatggca gtattcataa ttagcctgaa atgcattctg taggtaatct    4800
ctgagtttct ggaatatttt cttagacttt ttggatgtgc agcagcttac atgtctgaag    4860
ttacttgaag gcatcacttt taagaaagct tacagttggg ccctgtacca tcccaagtcc    4920
tttgtagctc ctcttgaaca tgtttgccat acttttaaaa gggtagttga ataaatagca    4980
tcaccattct ttgctgtggc acaggttata aacttaagtg gagtttaccg gcagcatcaa    5040
atgtttcagc tttaaaaaat aaaagtaggg tacaagttta atgtttagtt ctagaaattt    5100
tgtgcaatat gttcataacg atggctgtgg ttgccacaaa gtgcctcgtt tacctttaaa    5160
tactgttaat gtgtcatgca tgcagatgga aggggtggaa ctgtgcacta aagtgggggc    5220
tttaactgta gtatttggca gagttgcctt ctacctgcca gttcaaaagt tcaacctgtt    5280
ttcatataga atatatatac taaaaaattt cagtctgtta aacagcctta ctctgattca    5340
gcctcttcag atactcttgt gctgtgcagc agtggctctg tgtgtaaatg ctatgcactg    5400
aggatacaca aaaataccaa tatgatgtgt acaggataat gcctcatccc aatcagatgt    5460
ccatttgtta ttgtgtttgt taacaaccct ttatctctta gtgttataaa ctccacttaa    5520
aactgattaa agtctcattc ttgtcaaaaa aaaaaaaaaa aaaaaaaaa aa             5572
```

IDENTIFICATION OF EXTRACELLULAR FORM OF PTEN THAT CAN BE USED TO TREAT TUMORS

This application is a §371 national stage of PCT International Application No. PCT/US2010/000469, filed Feb. 17, 2010, claiming the benefit of U.S. Provisional Application No. 61/207,974, filed Feb. 17, 2009, the contents of which are hereby incorporated by reference.

This application incorporates-by-reference nucleotide and/or amino acid sequences which are present in the file named "110817_0575_79943A_PCT_US_Substitute_Sequence_Listing_WS.txt", which is 40.0 kilobytes in size, and which was created Aug. 16, 2011 in the IBM-PC machine format, having an operating system compatibility with MS-Windows, which is contained in the text file filed Aug. 17, 2011 as part of this application.

This invention was made with government support under grant no. CA082783 awarded by the National Cancer Institute. The government has certain rights in the invention.

Throughout this application, various publications are referenced in parentheses by first author and year. Full citations for these references may be found at the end of the specification immediately preceding the claims. The disclosures of these publications in their entireties are hereby incorporated by reference into this application to more fully describe the state of the art to which this invention pertains.

BACKGROUND

The PTEN tumor suppressor (see WO98/34624 which is hereby incorporated by reference in its entirety) is a cytoplasmic phosphatase which dephosphorylates the important second messenger phosphatidylinositol 3,4,5-triphosphate (Maehama and Dixon 1998). This activity downregulates the many oncogenic signals initiated by PIP3 activation of Akt including anti-apoptotic pathways, cell cycle progression and increasing cell metabolism (Sulis and Parsons 2003). The role of PTEN in cancer is evident from its frequent loss, either genetically or functionally, in many different tumor types (Bonneau and Longy 2000). Originally discovered as deleted in glial cancers, it has since been implicated in tumorigenesis of the prostate, breast, endometrium, melanocytes, kidneys and lungs. Germline mutations in PTEN were also linked to inherited cancer predisposition syndromes such as Cowden's Syndrome (Eng 2003). Mouse models of PTEN loss have recapitulated its role as an tumor suppressor both in the heterozygous mouse and tissue specific knockouts in many different tissue types (Di Cristofano, Pesce et al. 1998; Kwabi-Addo, Giri et al. 2001; Petrocelli and Slingerland 2001; You, Castrillon et al. 2002; Fraser, Zhu et al. 2004).

The PTEN protein contains an N-terminal dual specificity phosphatase domain, and a C-terminal C2 phospholipid binding domain, followed by an unstructured tail of regulatory importance because of the phosphorylation sites found within (Lee, Yang et al. 1999; Vazquez, Ramaswamy et al. 2000; Torres and Pulido 2001; Vazquez, Grossman et al. 2001). PTEN protein is mostly cytoplasmic however there is increasing evidence for a PTEN presence in the nucleus, a localization which is regulated by the monoubiquitination of the protein by NEDD4-1 (Baker 2007; Wang, Trotman et al. 2007).

Ribosome scanning of the 5'UTR precedes translation initiation which occurs at the start codon, AUG. Though the actual means by which the ribosome decides the proper start codon remains incompletely understood, there are certain properties of both the mRNA itself and the sequence which will dictate where the pre-initiation complex will slow its scanning and start to translate. The classic "Kozak sequence" CCACCATGG, where the underlined ATG is the initiation codon, has been shown to be the most favorable sequence context for initiation (Kozak 1991). mRNA secondary structure also promotes initiation probably by an actual slowing of the scanning of the pre-initiation complex which requires a helicase to melt secondary structures prior to reading (Kozak 1990).

In certain transcripts, translation initiation can occur from non-AUG codons. This usually comprises only a minor percentage of the total protein translated from a transcript and the result is a mixed species of proteins varying at their N-termini. Kozak delineated the efficiencies of translation initiation from non-AUG codons and found that GUG and CUG were both capable of initiating translation in vitro however far less efficiently (Kozak 1989). Further research has shown that the availability of methionine can alter the promiscuity of translation initiation through a mechanism that remains unclear, but probably involves the phosphorylation of eIF2, a component of the 43S pre-initiation complex, by a nutrient sensitive kinase (Hershey 1991; Hann 1994).

A number of proteins have been shown to be translated from alternate initiation codons. The transcription factor, c-myc, has an alternate upstream CUG initiation codon which when translated, adds 14 amino acids to the N-terminus of the protein (Hann and Eisenman 1984). This alternate isoform has been shown to be selectively disrupted in Burkitt's lymphoma (Hann, King et al. 1988). In tissue culture the longer form of myc is predominantly transcribed at high cell densities when methionine is at a low concentration (Hann, Sloan-Brown et al. 1992). Further studies have revealed that the longer form of c-myc is growth inhibitory and has a different set of transcriptional targets than the classic c-myc protein (Hann, Dixit et al. 1994). (Florkiewicz and Sommer 1989) (Prats, Kaghad et al. 1989).

Additionally, it is known that the actual subcellular localization of a protein can be dictated by alternate initiation codons. In the case of the mouse proto-oncogene int-2 alternate initiation from an upstream CUG codon encodes a nuclear localization while the AUG codon encodes a signal peptide for localization to the secretory pathway (Acland, Dixon et al. 1990). A similar phenomenon was described in the human FGF3, in which the protein translated from AUG is destined for the secretory pathway while the protein translated from an upstream CUG is localized to the nucleus (Kiefer, Acland et al. 1994). Furthermore, in some eukaryotic proteins, such as TEF-1 and PRPS-3, the protein is completely initiated from a CUG codon (Taira, Iizasa et al. 1990; Xiao, Davidson et al. 1991).

Proteins that are destined for secretion are targeted to the endoplasmic reticulum by a stretch of hydrophobic amino acids called a signal peptide (Blobel, Walter et al. 1979). Usually found at the N-termini of proteins, the signal peptide binds the signal recognition particle (SRP) upon translation and causes the ribosome to halt and translocate to the rough endoplasmic reticulum where it binds the SRP receptor. Once the ribosome docks, the SRP-SRP receptor complex is released and translation resumes through the lumen of the ER through the Sec61 translocon. The signal peptide is then cleaved off in the case of soluble proteins releasing the protein from the Sec translocon. In the case of proteins spanning a membrane, the transmembrane helix serves as a signal peptide for ER translocation. These proteins are modified extensively by glycosylation in the golgi and are shuttled to the plasma membrane in secretory vesicles (Alberts 2002).

There are a number of secreted proteins that have been shown to be important in cancer. The Wnt signaling pathway for example has been shown to be altered in lung cancer. Wnt is a secreted ligand for the family of Frizzled receptors. Wnt activation of frizzled causes disheveled to dissociate the β-catenin degradation complex, which includes APC, allowing for levels of β-catenin to rise and translocate to the nucleus where it can interact and transactivate the TCF transcription factor. Inactivating mutations in APC and activating mutations in β-catenin have been detailed in both inherited and sporadic colon cancer. Additionally, a number of extracellular ligand antagonists such as SFRP and Wnt-5a compete for the same Frizzled receptors as Wnt. Both have been shown to be tumor suppressors; the SFRP knockout mouse develops lymphoid tumors and epigenetic silencing of Wnt-5a has been detected in melanomas.

All published reports of PTEN have indicated that the protein is located in either the cytoplasm or nucleus. A number of extracellular proteins (glypicans and syndecans) were found to bind PTEN, as did a number of proteins involved in the secretory pathway (reticulocalbin and calumenin). It was assumed that PTEN entered the secretory pathway to allow for such interactions. In fact, as disclosed herein, a novel differentially translated protein exists, named PTEN-long, which contains an N-terminal signal peptide and which is secreted extracellularly.

SUMMARY OF THE INVENTION

An isolated human phosphatase and tensin homolog long polypeptide (PTEN-long) comprising consecutive amino acid residues having the sequence set forth in SEQ ID NO:1 or an analogue thereof comprising consecutive amino acid residues having the sequence set forth in SEQ ID NO:5, or a variant of each thereof.

A polypeptide comprising (i) residues 1 through 173 of SEQ ID NO:1, or (ii) an analogue thereof comprising residues 1 through 173 of SEQ ID NO:5, or (iii) residues 22 through 516 of SEQ ID NO:1.

A pharmaceutical composition comprising phosphatase and tensin homolog long polypeptide (PTEN-long) comprising consecutive amino acid residues having the sequence set forth in SEQ ID NO:1, or a fragment thereof comprising residues 22 through 516 of SEQ ID NO:1, or an analogue thereof comprising consecutive amino acid residues having the sequence set forth in SEQ ID NO:5.

A method for treating a solid tumor in a subject comprising administering to the subject an amount of a human phosphatase and tensin homolog long polypeptide (PTEN-long) comprising consecutive amino acid residues having the sequence set forth in SEQ ID NO:1, or a fragment thereof comprising residues 22 through 516 of SEQ ID NO:1, or an analogue thereof comprising consecutive amino acid residues having the sequence set forth in SEQ ID NO:5, effective to treat the solid tumor in the subject.

A method for inhibiting growth of a solid tumor in a subject comprising administering to the subject an amount of a human phosphatase and tensin homolog long polypeptide (PTEN-long) comprising consecutive amino acid residues having the sequence set forth in SEQ ID NO:1, or a fragment thereof comprising residues 22 through 516 of SEQ ID NO:1, or an analogue thereof comprising consecutive amino acid residues having the sequence set forth in SEQ ID NO:5, effective to inhibit growth of the solid tumor in the subject.

A method for inhibiting angiogenesis in a solid tumor in a subject comprising administering to the subject an amount of a human phosphatase and tensin homolog long polypeptide (PTEN-long) comprising consecutive amino acid residues having the sequence set forth in SEQ ID NO:1, or a fragment thereof comprising residues 22 through 516 of SEQ ID NO:1, or an analogue thereof comprising consecutive amino acid residues having the sequence set forth in SEQ ID NO:5, effective to inhibit angiogenesis in the solid tumor in the subject.

A method for inducing apoptosis of a vascular epithelial cell of a blood vessel in a solid tumor in a subject comprising administering to the subject an amount of a human phosphatase and tensin homolog long polypeptide (PTEN-long) comprising consecutive amino acid residues having the sequence set forth in SEQ ID NO:1, or a fragment thereof comprising residues 22 through 516 of SEQ ID NO:1, or an analogue thereof comprising consecutive amino acid residues having the sequence set forth in SEQ ID NO:5, effective to induce apoptosis of the vascular epithelial cell in the blood vessel in the solid tumor in the subject.

A method for treating a solid tumor in a subject comprising administering to the subject an amount of an expression vector which encodes human phosphatase and tensin homolog long polypeptide (PTEN-long) comprising SEQ ID NO:1, or a fragment thereof comprising residues 22 through 516 of SEQ ID NO:1, or an analogue thereof comprising SEQ NO:5, so as to express PTEN-long, PTEN-long fragment, or the analogue thereof, in cells of the solid tumor in an amount effective to treat the solid tumor in the subject.

A human phosphatase and tensin homolog long polypeptide (PTEN-long) comprising SEQ ID NO:1 or a fragment thereof comprising residues 22 through 516 of SEQ ID NO:1, or an analogue thereof comprising SEQ ID NO:5 for use in treating a solid tumor in a subject, for inhibiting growth of a solid tumor in a subject, for inducing apoptosis of a vascular epithelial cell in a solid tumor in a subject, or for inhibiting angiogenesis in a solid tumor in a subject.

A composition comprising human phosphatase and tensin homolog long polypeptide (PTEN-long) comprising SEQ ID NO:1, or a fragment thereof comprising residues 22 through 516 of SEQ ID NO:1, or an analogue thereof comprising SEQ ID NO:5, bonded to a non-peptide agent which increases the plasma half-life of the PTEN-long, PTEN-long fragment, or the analogue thereof, respectively.

An isolated nucleic acid which encodes a human phosphatase and tensin homolog long polypeptide (PTEN-long) comprising SEQ ID NO:1, or which encodes a fragment thereof comprising residues through 516 of SEQ ID NO:1, or which encodes an analogue thereof comprising SEQ ID NO:5.

An expression vector comprising a nucleic acid encoding human phosphatase and tensin homolog long polypeptide (PTEN-long) comprising SEQ ID NO:1, or a fragment thereof comprising residues 22 through 516 of SEQ ID NO:1, or an analogue thereof comprising SEQ ID NO:5.

A transformed cell capable of expressing human phosphatase and tensin homolog long polypeptide (PTEN-long) comprising SEQ ID NO:1, or a fragment thereof comprising residues 22 through 516 of SEQ ID NO:1, or an analogue thereof comprising SEQ ID NO:5, wherein the cell has integrated into its genome a recombinant DNA which encodes PTEN-long or an analogue thereof.

A host cell capable of expressing human phosphatase and tensin homolog long polypeptide (PTEN-long) comprising SEQ ID NO:1, or a fragment thereof comprising residues 22 through 516 of SEQ ID NO:1, or an analogue thereof comprising SEQ ID NO:5, wherein the host cell comprises a plasmid which encodes PTEN-long or an analogue thereof.

A process comprising admixing (1) human phosphatase and tensin homolog long polypeptide (PTEN-long) comprising SEQ ID NO:1, or a fragment thereof comprising residues 22 through 516 of SEQ ID NO:1, or an analogue thereof comprising SEQ ID NO:5, and (2) a non-peptide agent which increases the plasma half-life of PTEN-long or the analogue thereof, so as to make PTEN-long comprising SEQ ID NO:1, or the fragment thereof comprising residues 22 through 516 of SEQ ID NO:1, or the analogue thereof comprising SEQ ID NO:5, bonded to the non-peptide agent which increases the plasma half-life of the PTEN-long, PTEN-long fragment, or the analogue thereof, respectively.

An isolated nucleic acid molecule consisting of at least a 20 nucleotide fragment of the nucleic acid sequence of SEQ ID NO:2 or SEQ ID NO:6 or a complement thereof that specifically hybridizes under stringent conditions to a complement of the nucleic acid sequence of SEQ ID NO: 2 or SEQ ID NO:6, or to SEQ ID NO:2 SEQ ID NO:6.

An isolated antibody, or fragment thereof, wherein the antibody or fragment thereof binds to (1) PTEN-long polypeptide which comprises amino acid residues 1-173 of SEQ ID NO:1 or (2) an analogue thereof comprising SEQ ID NO:5 or (3) the amino acids having the sequence set forth in SEQ ID NO:3 or (4) a fragment of PTEN-long comprising residues 22 through 516 of SEQ ID NO:1.

An isolated antibody or fragment thereof, wherein the antibody or fragment thereof binds to a conformational epitope of PTEN-long, wherein the PTEN-long comprises the sequence set forth in residues 1-173 of SEQ ID NO:1, but wherein the antibody does not bind to PTEN.

An isolated antibody or fragment thereof, wherein the antibody or fragment thereof binds to an epitope of a PTEN-long, wherein the PTEN-long comprises the sequence set forth in residues 1-173 of SEQ ID NO:1, but wherein the antibody does not bind to PTEN.

A peptide fragment of SEQ ID NO:1, or SEQ ID NO:5, which fragment has anti-tumor, anti-angiogenic, or anti-apoptotic activity.

BRIEF DESCRIPTION OF THE FIGURES

FIG. 3. Alignment of N-termini of PTEN Orthologs. PTEN protein sequences from indicated species were aligned using BLOSUM62 score matrix on Vector NTI (Invitrogen). Extended N-terminal sequence for both *Homo sapiens* and *Mus musculus* (asterix) were translated from published mRNA using a CUG alternate initiation codon at −519 (*H. sapiens*) and −520 (*M. musculus*) from the canonical AUG start codon using ORFinder (NCBI). mRNA sequences from *Homo sapiens* (NM_000314) and *Mus musculus* (NM_008960). *Apis mellifera* sequence was obtained from Baylor College of Medicine Honey Bee Genome Project. Protein sequence for *Caenorhabditis elegans* PTEN (Daf-18) was downloaded from Wormbase. *Bos Taurus* (XM_613125) and *Pan troglodytes* (XP_521544) were downloaded from NCBI.

DETAILED DESCRIPTION OF THE INVENTION

Figure 1:
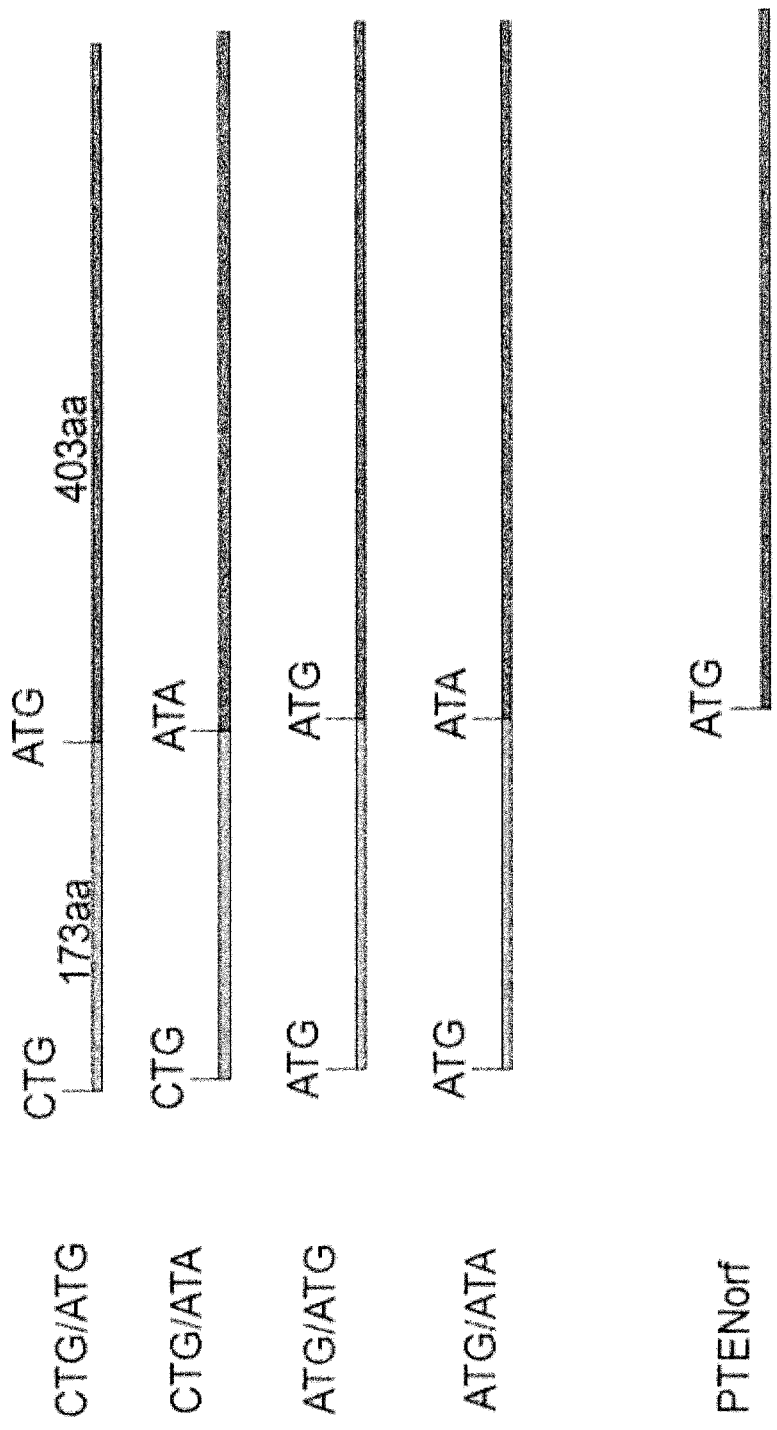
FIG. 1. Diagram of PTEN-long Constructs. Expression constructs showing the combinations created for driving expression of PTEN either from the endogenous start site or the alternate start site. Canonical PTEN is shown in black while the translated region in the UTR is shown in gray.

An isolated human phosphatase and tensin homolog long polypeptide (PTEN-long) comprising consecutive amino acid residues having the sequence set forth in SEQ ID NO:1 or an analogue thereof comprising consecutive amino acid residues having the sequence set forth in SEQ ID NO:5, or a variant of each thereof.

A polypeptide comprising (i) residues 1 through 173 of SEQ ID NO:1, or (ii) an analogue thereof comprising residues 1 through 173 of SEQ ID NO:5, or (iii) residues 22 through 516 of SEQ ID NO:1.

A pharmaceutical composition comprising phosphatase and tensin homolog long polypeptide (PTEN-long) comprising consecutive amino acid residues having the sequence set forth in SEQ ID NO:1, or a fragment thereof comprising residues 22 through 516 of SEQ ID NO:1, or an analogue thereof comprising consecutive amino acid residues having the sequence set forth in SEQ ID NO:5.

A method for treating a solid tumor in a subject comprising administering to the subject an amount of a human phosphatase and tensin homolog long polypeptide (PTEN-long) comprising consecutive amino acid residues having the sequence set forth in SEQ ID NO:1, or a fragment thereof comprising residues 22 through 516 of SEQ ID NO:1, or an analogue thereof comprising consecutive amino acid residues having the sequence set forth in SEQ ID NO:5, effective to treat the solid tumor in the subject.

A method for inhibiting growth of a solid tumor in a subject comprising administering to the subject an amount of a human phosphatase and tensin homolog long polypeptide (PTEN-long) comprising consecutive amino acid residues having the sequence set forth in SEQ ID NO:1, or a fragment thereof comprising residues 22 through 516 of SEQ ID NO:1, or an analogue thereof comprising consecutive amino acid residues having the sequence set forth in SEQ ID NO:5, effective to inhibit growth of the solid tumor in the subject.

A method for inhibiting angiogenesis in a solid tumor in a subject comprising administering to the subject an amount of a human phosphatase and tensin homolog long polypeptide (PTEN-long) comprising consecutive amino acid residues having the sequence set forth in SEQ ID NO:1, or a fragment thereof comprising residues 22 through 516 of SEQ ID NO:1, or an analogue thereof comprising consecutive amino acid residues having the sequence set forth in SEQ ID NO:5, effective to inhibit angiogenesis in the solid tumor in the subject.

A method for inducing apoptosis of a vascular epithelial cell of a blood vessel in a solid tumor in a subject comprising administering to the subject an amount of a human phosphatase and tensin homolog long polypeptide (PTEN-long) comprising consecutive amino acid residues having the sequence set forth in SEQ ID NO:1, or a fragment thereof comprising residues 22 through 516 of SEQ ID NO:1, or an analogue thereof comprising consecutive amino acid residues having the sequence set forth in SEQ ID NO:5, effective to induce apoptosis of the vascular epithelial cell in the blood vessel in the solid tumor in the subject.

In an embodiment of the methods described herein the tumor is a cancerous tumor. In an embodiment of the methods described herein the cancerous tumor is a tumor of the subject's glial cells, prostate, ovaries, uterus, endometrium, breast, melanocyte, kidney, lung, colon, head, neck, or pancreas.

In an embodiment of the methods described herein the cancerous tumor is activated by PTEN or by a PI3K pathway or is PTEN-negative.

In an embodiment of the methods described herein the PTEN-long, or the analogue thereof, or the PTEN-long fragment, is administered to the subject by direct introduction into the solid tumor. In an embodiment of the methods described herein the PTEN-long, or the analogue thereof, or the PTEN-long fragment is injected into the solid tumor. In an embodiment of the methods described herein the PTEN-long, or the analogue thereof, or the PTEN-long fragment is directly introduced into the solid tumor by a catheter. In an embodiment of the methods described herein the PTEN-long, or the analogue thereof, or the PTEN-long fragment is administered to the subject by direct introduction into a blood vessel supplying the solid tumor. In an embodiment of the methods described herein the PTEN-long, or the analogue thereof, or the PTEN-long fragment is injected into the blood vessel supplying the solid tumor. In an embodiment of the methods described herein the PTEN-long, or the analogue thereof, or the PTEN-long fragment is directly introduced by a catheter into the blood vessel supplying the solid tumor. In an embodiment of the methods described herein the PTEN-long, or the analogue thereof, or the PTEN-long fragment, is administered to the subject intravenously. In an embodiment of the methods described herein the PTEN-long, or the analogue thereof, or the PTEN-long fragment is administered to the subject subcutaneously.

A method for treating a solid tumor in a subject comprising administering to the subject an amount of an expression vector which encodes human phosphatase and tensin homolog long polypeptide (PTEN-long) comprising SEQ ID NO:1, or a fragment thereof comprising residues 22 through 516 of SEQ ID NO:1, or an analogue thereof comprising SEQ ID NO:5, so as to express PTEN-long, PTEN-long fragment, or the analogue thereof, in cells of the solid tumor in an amount effective to treat the solid tumor in the subject.

A human phosphatase and tensin homolog long polypeptide (PTEN-long) comprising SEQ ID NO:1 or a fragment thereof comprising residues 22 through 516 of SEQ ID NO:1, or an analogue thereof comprising SEQ ID NO:5 for use in treating a solid tumor in a subject, for inhibiting growth of a solid tumor in a subject, for inducing apoptosis of a vascular epithelial cell in a solid tumor in a subject, or for inhibiting angiogenesis in a solid tumor in a subject.

In an embodiment of the compound for the uses described herein the tumor is a cancerous tumor. In an embodiment of the methods described herein the cancerous tumor is a glial, prostate, breast, endometrium, melanocyte, kidney or lung cancer tumor.

In an embodiment of the compound for the uses described herein the cancerous tumor is activated by PTEN by a PI3K pathway or is PTEN-negative.

A composition comprising human phosphatase and tensin homolog long polypeptide (PTEN-long) comprising SEQ ID NO:1, or a fragment thereof comprising residues 22 through 516 of SEQ ID NO:1, or an analogue thereof comprising SEQ ID NO:5, bonded to a non-peptide agent which increases the plasma half-life of the PTEN-long, PTEN-long fragment, or the analogue thereof, respectively.

In an embodiment the compositions described herein further comprising a pharmaceutical carrier. In an embodiment of the compositions described herein the non-peptide agent which increases the plasma half-life is polyethylene glycol (PEG). In an embodiment of the compositions described the PEG is bonded to a C-terminus or to a N-terminus of the PTEN-long, PTEN-long fragment, or the analogue thereof. In an embodiment of the compositions described the non-peptide agent which increases the plasma half-life is 9-fluorenylmethyl chloroformate (Fmoc) or (7-sulfo)-9-fluorenylmethoxycarbonyl.

An isolated nucleic acid which encodes a human phosphatase and tensin homolog long polypeptide (PTEN-long) comprising SEQ ID NO:1, or which encodes a fragment thereof comprising residues 22 through 516 of SEQ ID NO:1, or which encodes an analogue thereof comprising SEQ ID NO:5.

In an embodiment the nucleic acid comprises consecutive nucleotides having the sequence set forth in SEQ ID NO:2 or SEQ ID NO:6. In an embodiment the nucleic acid comprises consecutive nucleotide residues 503 to 2243 of the sequence set forth in SEQ ID NO:2 or SEQ ID NO:6. In an embodiment the nucleic acid comprises consecutive nucleotides having the sequence set forth in SEQ ID NO:3 or SEQ ID NO:7. In an embodiment the nucleic acid comprises consecutive nucleotide residues 503 to 2243 of the sequence set forth in SEQ ID NO:3 or SEQ ID NO:7. In an embodiment the nucleic acid is a RNA. In an embodiment the nucleic acid is a DNA. In an embodiment the nucleic acid is a cDNA.

An expression vector comprising a nucleic acid encoding human phosphatase and tensin homolog long polypeptide (PTEN-long) comprising SEQ ID NO:1, or a fragment thereof comprising residues 22 through 516 of SEQ ID NO:1, or an analogue thereof comprising SEQ ID NO:5.

A transformed cell capable of expressing human phosphatase and tensin homolog long polypeptide (PTEN-long) comprising SEQ ID NO:1, or a fragment thereof comprising residues 22 through 516 of SEQ ID NO:1, or an analogue thereof comprising SEQ ID NO:5, wherein the cell has integrated into its genome a recombinant DNA which encodes PTEN-long or an analogue thereof.

A host cell capable of expressing human phosphatase and tensin homolog long polypeptide (PTEN-long) comprising SEQ ID NO:1, or a fragment thereof comprising residues 22 through 516 of SEQ ID NO:1, or an analogue thereof comprising SEQ ID NO:5, wherein the host cell comprises a plasmid which encodes PTEN-long or an analogue thereof.

In an embodiment the host cell is a bacterial cell. In an embodiment the host cell is a mammalian cell.

A process comprising admixing (1) human phosphatase and tensin homolog long polypeptide (PTEN-long) comprising SEQ ID NO:1, or a fragment thereof comprising residues 22 through 516 of SEQ ID NO:1, or an analogue thereof comprising SEQ ID NO:5, and (2) a non-peptide agent which increases the plasma half-life of PTEN-long or the analogue thereof, so as to make PTEN-long comprising SEQ ID NO:1, or the fragment thereof comprising residues 22 through 516 of SEQ ID NO:1, or the analogue thereof comprising SEQ ID NO:5, bonded to the non-peptide agent which increases the plasma half-life of the PTEN-long, PTEN-long fragment, or the analogue thereof, respectively.

An isolated nucleic acid molecule consisting of at least a 20 nucleotide fragment of the nucleic acid sequence of SEQ ID NO:2 or SEQ ID NO:6 or a complement thereof that specifically hybridizes under stringent conditions to a complement of the nucleic acid sequence of SEQ ID NO: 2 or SEQ ID NO:6, or to SEQ ID NO:2 SEQ ID NO:6.

An isolated antibody, or fragment thereof, wherein the antibody or fragment thereof binds to (1) PTEN-long polypeptide which comprises amino acid residues 1-173 of SEQ ID NO:1 or (2) an analogue thereof comprising SEQ ID NO:5 or (3) the amino acids having the sequence set forth in SEQ ID NO:3 or (4) a fragment of PTEN-long comprising residues 22 through 516 of SEQ ID NO:1.

In an embodiment the antibody is a monoclonal antibody. In an embodiment the antibody is an antibody fragment. In an embodiment the antibody fragment is a Fab, Fab', F(ab')$_2$, or Fv fragment. In an embodiment the antibody fragment is a single-chain antibody. In an embodiment the antibody is a humanized antibody.

An isolated antibody or fragment thereof, wherein the antibody or fragment thereof binds to a conformational epitope of PTEN-long, wherein the PTEN-long comprises the sequence set forth in residues 1-173 of SEQ ID NO:1, but wherein the antibody does not bind to PTEN.

In an embodiment the antibody binds to an epitope comprised of any of residues 153-173 of SEQ ID NO:1.

An isolated antibody or fragment thereof, wherein the antibody or fragment thereof binds to an epitope of a PTEN-long, wherein the PTEN-long comprises the sequence set forth in residues 1-173 of SEQ ID NO:1, but wherein the antibody does not bind to PTEN.

In an embodiment the antibody binds to residues 153-173, or a portion thereof, of SEQ ID NO:1.

A peptide fragment of SEQ ID NO:1, or SEQ ID NO:5, which fragment has anti-tumor, anti-angiogenic, or anti-apoptotic activity. In an embodiment the peptide comprises 5-10, 10-20, 20-30, or 30-40 amino acids. In an embodiment the peptide comprises amino acids 1-173 of SEQ ID NO:1 or SEQ ID NO:5. In an embodiment the peptide comprises consecutive amino acid residues 22 through 516 of SEQ ID NO:1. In an embodiment the peptide does not comprise consecutive amino acid residues 174 through 576 of SEQ ID NO:1 or SEQ ID NO:5.

As used herein, a "prophylactically effective" amount of a substance is an amount effective to prevent or to delay the onset of a given pathological condition in a subject to which the substance is administered.

As used herein, a "therapeutically effective" amount of a substance is an amount effective to treat, ameliorate or lessen a symptom or cause of a given pathological condition in a subject suffering therefrom to which subject the substance is administered.

In one embodiment, the therapeutically or prophylactically effective amount is from about 1 mg of agent/subject to about 1 g of agent/subject per dosing. In another embodiment, the therapeutically or prophylactically effective amount is from about 10 mg of agent/subject to 500 mg of agent/subject. In a further embodiment, the therapeutically or prophylactically effective amount is from about 50 mg of agent/subject to 200 mg of agent/subject. In a further embodiment, the therapeutically or prophylactically effective amount is about 100 mg of agent/subject. In still a further embodiment, the therapeutically or prophylactically effective amount is selected from 50 mg of agent/subject, 100 mg of agent/subject, 150 mg of agent/subject, 200 mg of agent/subject, 250 mg of agent/subject, 300 mg of agent/subject, 400 mg of agent/subject and 500 mg of agent/subject.

"Administering" an agent can be effected or performed using any of the various methods and delivery systems known to those skilled in the art. The administering can be, for example, intravenous, oral, nasal, intraperitoneal, via the cerebrospinal fluid, via implant, transmucosal, transdermal, intramuscular, intravascular, intra-arterial, intracoronary, intramyocardial or subcutaneous.

The term "PTEN-long analogue" encompasses polypeptides which have one or more modified amino acids, but retain at least 90% sequence similarity with SEQ ID NO:1, and that retain or improve on the activity of inhibition of tumor growth as measured by the in vivo study described hereinbelow. PTEN itself (i.e. the polypeptide defined by only residues 174-576 of SEQ ID NO:1) is expressly excluded.

The term "PTEN-long variant" encompasses polypeptides which have one or more additional amino acids, typically having less than 5 additional amino acids at either the N-terminus or the C-terminus of PTEN-long, or both, and which retains or improves on the activity of inhibition of tumor growth as measured by the in vivo study described hereinbelow is retained.

The term "PTEN-long analogue variant" encompasses polypeptides which have one or more additional amino acids, typically having less than 5 additional amino acids at either the N-terminus or the C-terminus of PTEN-long analogue (i.e. SEQ ID NO:5), or both, and which retains or improves on the activity of inhibition of tumor growth as measured by the in vivo study described hereinbelow is retained.

All embodiments herein referring to a PTEN-long analogue are applicable mutatis mutandis to a PTEN-long variant.

PTEN-long has otherwise sometimes been referred to as PTEN-beta, PTEN-β, PTEN-S.

Injectable drug delivery systems for the PTEN-long, PTEN-long analogue, PTEN-long variant, PTEN-long analogue variant, or conjugates of each thereof, include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as the non limiting examples PLGA and polycaprylactone.

Oral delivery systems for the compositions and compounds of the invention include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems for the compositions and compounds of the invention include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems for the compositions and compounds of the invention include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems for the compositions and compounds of the invention include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

As used herein, "5'ATR" is the 5' alternately translated region as described in the Experimental section hereinbelow.

As used herein, a "pharmaceutical carrier" is a pharmaceutically acceptable solvent, suspending agent or vehicle, for delivering the instant compounds or compositions to the animal or human. The carrier may be liquid, aerosol, gel or solid and is selected with the planned manner of administration in mind.

"Non-peptide agent" shall mean any chemical entity, including, without limitation, a glycomer, a polymer, a small molecule (i.e. a hydrocarbon-based molecule or organic molecule having a molecular weight of less than 1000), a lipid, a liposome. Examples of non-peptide agents include, but are not limited to, PEG, Fmoc and FMS.

"Solid Tumor" as used herein includes cancerous and non-cancerous solid tumors. Cancerous solid tumors include, without limitation, biliary tract cancer; brain cancer, including glioblastomas and medulloblastomas; breast cancer; cervical cancer; choriocarcinoma; colon cancer; endometrial cancer; esophageal cancer; gastric cancer; intraepithelial neoplasms, including Bowen's disease and Paget's disease; liver cancer; lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; colorectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma [teratomas, choriocarcinomas]), stromal tumors and germ cell tumors; thyroid cancer, including thyroid adenocarcinoma and medullar carcinoma; and renal cancer including adenocarcinoma and Wilms tumor, but excludes tumors of non-solid tissues such as leukemias and other hematological neoplasms, including acute lymphocytic and myelogenous leukemia; multiple myeloma; AIDS associated leukemias and adult T-cell leukemia lymphoma.

SEQ ID NO:1 of the sequence listing is the full length PTEN-long protein sequence. Amino acid residues 1 to 173 of SEQ ID NO:1 represent the novel residues of PTEN-long that are encoded by the 5' ATR mRNA sequence (see description of SEQ ID NO:2 below). The canonical initiator methionine of PTEN is amino acid residue 174 of SEQ ID NO:1.

SEQ ID NO:2 is the full length PTEN-long mRNA sequence. The 5' ATR sequence of PTEN-long begins at nucleotide 513 of SEQ ID NO:2, the non-canonical CUG initiation codon, and ends at nucleotide 1031 of SEQ ID NO:2. The 5' ATR is in frame with the PTEN open reading frame, beginning at the canonical AUG initiation codon at nucleotide 1032 of SEQ ID NO:2 and ending at nucleotide 2243 of SEQ ID NO:2. Thus, the PTEN-long open reading frame extends from nucleotide 513 of SEQ ID NO:2 to nucleotide 2243 of SEQ ID NO:2 and leads to the addition of 173 amino acids to the N-terminus of PTEN. The protein is referred to as PTEN-long.

SED ID NO:3 is the cDNA corresponding to the full length PTEN-long mRNA sequence.

SEQ ID NO:4 is the peptide of PTEN-long protein sequence comprising amino acid residues 153 to 173 of SEQ ID NO:1. This unique peptide represents a unique epitope derived from PTEN-long that is not found in PTEN.

SEQ ID NO:5 is a full length PTEN-long analogue protein sequence. Amino acid residue 1 of PTEN-long has been changed from Leu to Met in the analogue to increase protein yields.

SEQ ID NO:6 is the modified full length PTEN-long analogue mRNA sequence. The 5' ATR sequence of the PTEN-long analogue begins at nucleotide 513 of SEQ ID NO:6, at the engineered AUG initiation codon, and ends at nucleotide 1031 of SEQ ID NO:6.

SEQ ID NO:7 is the modified cDNA corresponding to the modified full length PTEN-long analogue mRNA sequence.

Where a range is given in the specification it is understood that the range includes all integers and 0.1 units within that range, and any sub-range thereof. For example, a range of 77 to 90% includes 77.0%, 77.1%, 77.2%, 77.3%, 77.4%, 77.5%, 77.6%, 77.7%, 77.8%, 77.9%, 80.0%, 80.1%, 80.2%, 80.3%, 80.4%, 80.5%, 80.6%, 80.7%, 80.8%, 80.9%, and 90.0%, as well as the range 80% to 81.5% etc.

All combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

The PTEN tumor suppressor is one of the most commonly altered genes in cancer. It functions as a lipid phosphatase of phosphatidylinositiol 3,4,5-triphosphate which in turn suppresses oncogenic signaling from phosphatidylinositol 3-kinase (PI3K) and Akt. Inspection of PTEN mRNA revealed that the 5' untranslated region (UTR) is in frame with the open reading frame (ORF) of PTEN for 770 bp. Within this UTR ORF, there is an alternate CUG start codon within a weak Kozak sequence at 513 base pairs upstream of the canonical AUG start codon. While expression of the canonical PTEN ORF generates a protein which migrates at approximately 55 kDa, expression of PTEN cDNA containing the 5'UTR is able to generate a second protein at 70 kDa called PTEN-long. Mutation of the start sites indicated that the 55 kDa PTEN is generated from translation at the canonical start codon while PTEN-long is initiated from the upstream alternate start site. Immunoblotting with different PTEN antibodies demonstrated the endogenous presence of PTEN-long in multiple cells lines. Knockdown and knockout studies in mouse ES cells confirmed that this larger protein was indeed PTEN. The added N-terminal protein sequence encoded a signal peptide and cleavage site, indicating that PTEN-long enters the secretory pathway. PTEN-long preferentially binds the lectin concanavalin A, demonstrating that it is glycosylated. Furthermore, PTEN-long can be purified from conditioned media by affinity purification using both an antibody to PTEN as well as heparan sulfate. PTEN-long is also sensitive to degradation in an in vivo protease protection assay while normal PTEN is not, indicating that PTEN-long is located on the outside of the cell membrane.

Reagents, Cell Lines and Antibodies—

Proteinase K and concanavalin—A were purchased from Sigma (St. Louis, Mo.). Heparin sepharose and HiTrap Heparin HP columns were purchased from Amersham (Piscataway, N.J.). Antibodies to PTEN were purchased from Cell Signaling (Danvers Mass.) and Cascade (Winchester Mass.). Akt antibody was obtained from Cell Signaling (Danvers Mass.) and E cadhein antibody from Upstate Millipore (Billerica, Mass.). A polyclonal affinity purified antibody raised against the epitope PRHQQLLPSLSSFFFSHRLPD (SEQ ID NO:3), found in the novel translation of PTEN, was performed by Zymed Laboratories (South San Francisco, Calif.). Secondary antibodies were purchased from Pierce (Rockford, Ill.). HEK293, ZR-75-1, SKBR-3, MDAMB-361, BT549, and PC3 were obtained from ATCC (Manassas, Va.) and grown according to supplied guidelines.

Figure 5:
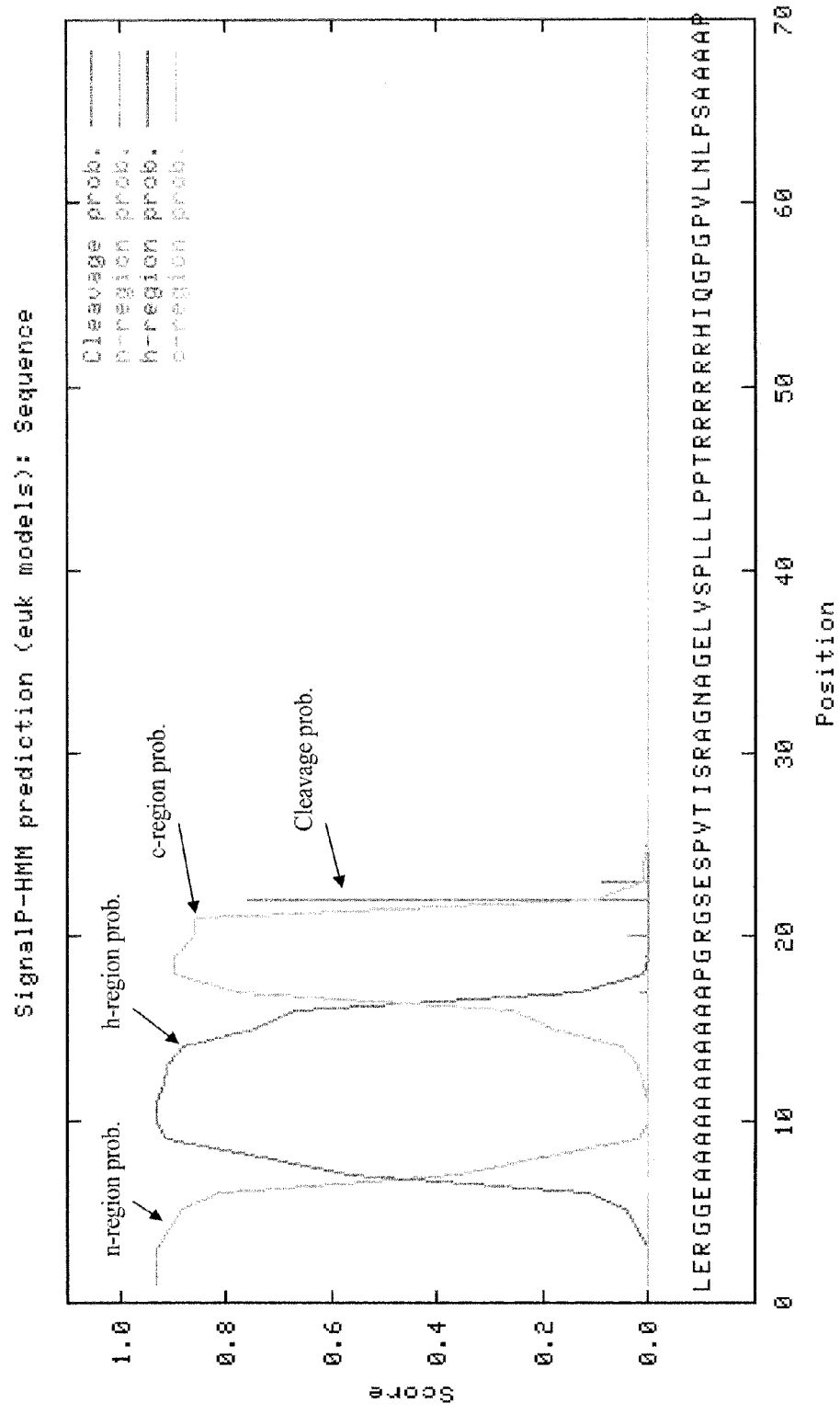
FIG. 5. Signal Peptide Prediction. PTEN 5'UTR sequence was translated and inputed into SignalIP3.0. Hidden markov model for eukaryotic signal peptides was used for prediction. The N-region denotes the positively charged N-terminal sequence of the signal peptide. The H-region is the hydrophobic core of the signal peptide. The C-region is mildly polar region marked by a proline which usually breaks the helix of the hydrophobic core. The cleavage probability is predictive of a cleavage site to release the signal peptide, allowing the protein to be released into the lumen of the ER. (Dalbey and Heijne, 2002). Cleavage is predicted to occur at position 21.

Plasmids and Contructs— pCEP4-PTEN, encoding the full open reading frame of PTEN and 5'-untranslated region was generated as previously reported by cloning PTEN cDNA (deposited in NCBI as U90351) into the NotI site of pCEP4 (Invitrogen) (Li, Simpson et al. 1998). The 5'UTR was further extended on this plasmid by ligating an adaptor encoding sequence upstream of the original NotI restriction site used for cloning. The adaptor encoded up to 10 base pairs upstream of the first possible alternate CTG start codon located at −513 of the canonical start site. An adaptor in which the putative alternate start site was mutated to ATG was also used to create a second set of expression constructs in which the long form would be efficiently expressed. Furthermore mutagenesis of the canonical start codon to ATA was also performed, yielding in total 4 different constructs (FIG. 5.1). These variations, as well as the open reading frame of the original PTEN were also subcloned into MSCV (Clontech, Mountainview, Calif.) retrovirus vector for stable expression via infection.

Protease Protection Assay—

HEK293 cells were collected in ice-cold PBS without trypsin and 5×10⁵ cell aliquots were incubated for 30 minutes with increasing concentrations of Proteinase K, from 0.5 ug/ml to 10 ug/ml. A control with Triton 0.1% was included to verify the ability of Proteinase K to degrade the indicated proteins. The reaction was stopped with 5 mM PMSF. Cells were lysed in 2× Laemmli sample buffer (125 nM Tris pH 6.8, 20% glycerol, 0.05% bromophenol blue, 4% SDS, 10% 2-mercaptoethanol) and immunoblotted for PTEN, Akt and E cadherin.

PTEN Purification from Mouse Livers—

Livers from C57BL6 mice were snap frozen in liquid nitrogen, pulverized, and resuspended in TNN buffer (50 mM Tris pH 7.4, 150 mM NaCl, 0.5% NP-40, 5 mM EDTA, 3% glycerol, 1 mM DTT, 1× Mammalian Protease Cocktail Inhibitors [Sigma]). The suspension was homogenized with a mortar and centrifuged at 40,000 RPM at 4 degrees for 1 hour. Supernatant was filtered successively with 0.45 micron and 0.22 micron filters. A sephacryl 200 size exclusion column (Amersham) was pre-equilibrated with TNN and the sample was applied at a rate of 0.3 ml/hr, followed by buffer. 2 ml fractions were collected and the low molecular weight samples were pooled and applied to a pre-equilibrated HiTrap Hepain HP column (Amersham). The column was washed with three column volumes of TNN and protein was eluted with stepwise 3× column volumes of 0.3M, 0.5M and 1M NaCl TNN solutions. Fractions were collected in 0.5 ml increments and immunoblotted for PTEN.

PTEN Heparin Purification from Media—

HEK293 cells were grown to confluency in 10% FBS DMEM in 15 cm dishes. The cells were incubated overnight with 15 ml of DMEM without FBS. The media from 20 plates was collected and filtered through a 0.45 micron filter. A 1 ml Heparin HP column was equilibrated with DMEM using AktaPrime (AmershamBioscience) using a flow of 4 ml/min at 4° C. Conditioned media was then passed through the column at 1 ml/min. The column was washed with 10 volumes of BC200 (200 mM Nacl, 50 mMT Tris pH7.4, 1 mM EDTA, 0.2% Triton X-100). Proteins were eluted with 5 ml of 1M NaCl at 1 ml/min in 1 ml fractions. The protein concentration of each fraction was determines by OD at 280 nm. Half of each fraction was precipitated with 20% with trichloroacetic acid, washed with cold acetone dried under vacuum. Protein was reconstituted in 20 ul Laemmli lysis buffer and immunoblotted using an antibody to PTEN and PTEN-long.

PTEN Purification from Serum—

Human serum from AB plasma was obtained from Sigma. 1 ml of serum was filtered through a 0.45 micron filter and precleared of antibodies using Protein A/G agarose for 1 hour incubation. Heparin-agarose was incubated with the precleared serum overnight along with a sepharose control and washed the next day with BC150 (150 mM NaCl, 25 mM Tris pH7.4, 1% NP-40, 0.25% Na Deoxycholate, 1 mM EDTA). Proteins were eluted with laemmli sample buffer and immunoblotted for PTEN or secondary only for heavy chain contamination.

Concanavalin a Pulldown—

HEK293 cells were lysed at subconfluency with BC500 (500 mM NaCl, 20 mM Tris pH 7.4, 1% Triton X-100, 1 mM $MnCl_2$, 1 mM $CaCl_2$, 1× Protease Inhibitor Cocktail). The cell lysate was centrifuged and filtered. Pulldowns were performed with 20 microliters of concanavalin A sepharose (Sigma) for 1 hour at 4° C. The resin was washed with BC500 and protein was eluted with Laemmli sample buffer.

Results

PTEA mRNA has an Upstream Alternate Initiation Start Site

Figure 2:
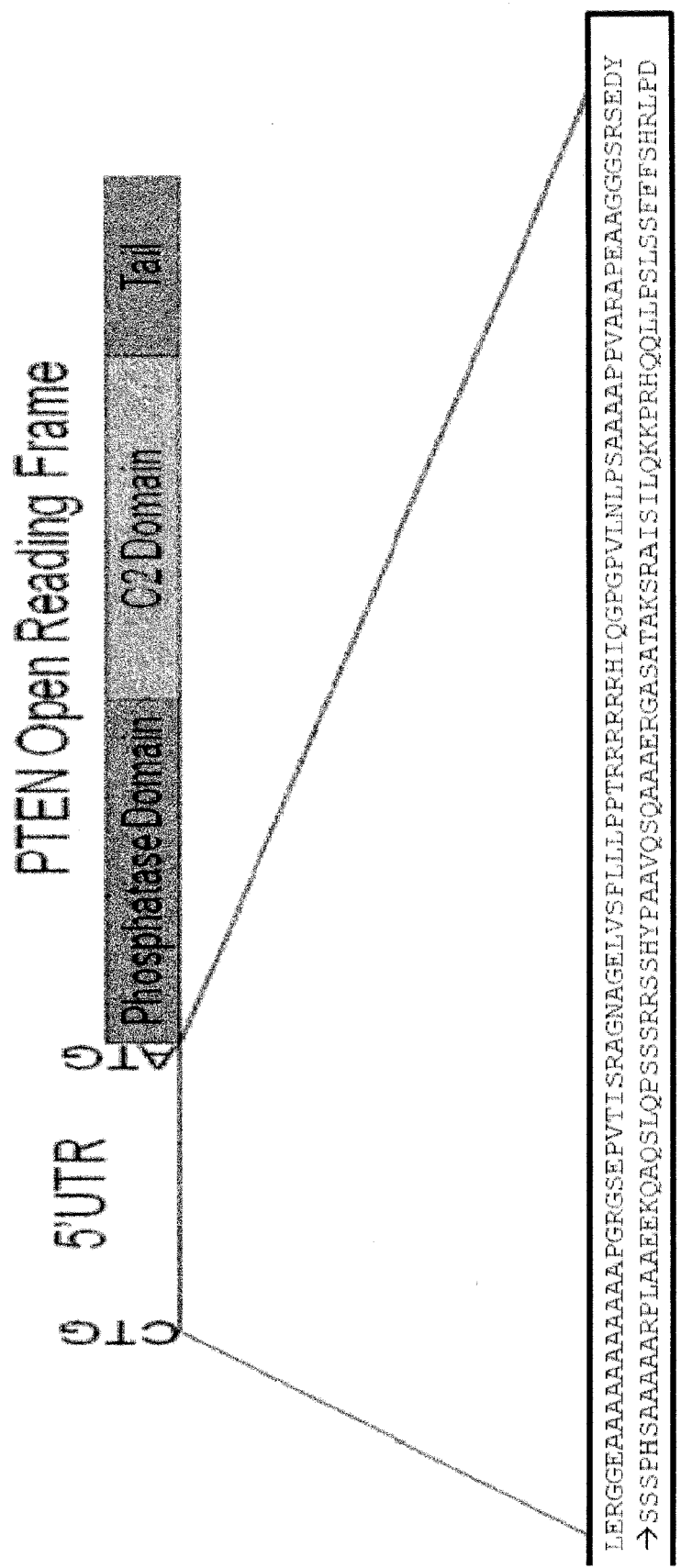
FIG. 2. Diagram of *Homo sapiens* PTEN mRNA. The PTEN mRNA encodes 173 amino acids in frame with and upstream of the canonical ATG start codon shown. Translation begins upstream from the canonical ATG at a CTG at nucleotide −519. Expanded is shown residues 1-173 of SEQ ID NO:1.

PTEN mRNA deposited into NCBI (Li and Sun 1997; Steck, Pershouse et al. 1997) contains an extensive 5'UTR. Approximately 770 bp of contiguous sequence in the 5'UTR region is in frame with the start codon. No methionines are encoded in this region; however, there are several alternate initiation CUG codons beginning at −519 from the canonical start codon. Translation of this sequence revealed no identifiable domains according to scansite (scansite.mit.edu) and prosite (www.ebi.ac.uk/ppsearch). Translation of this entire region would add 173 amino acids to PTEN increasing its molecular mass to approximately 70 kilodaltons (FIG. 2 and SEQ ID NO:1).

Figure 3:
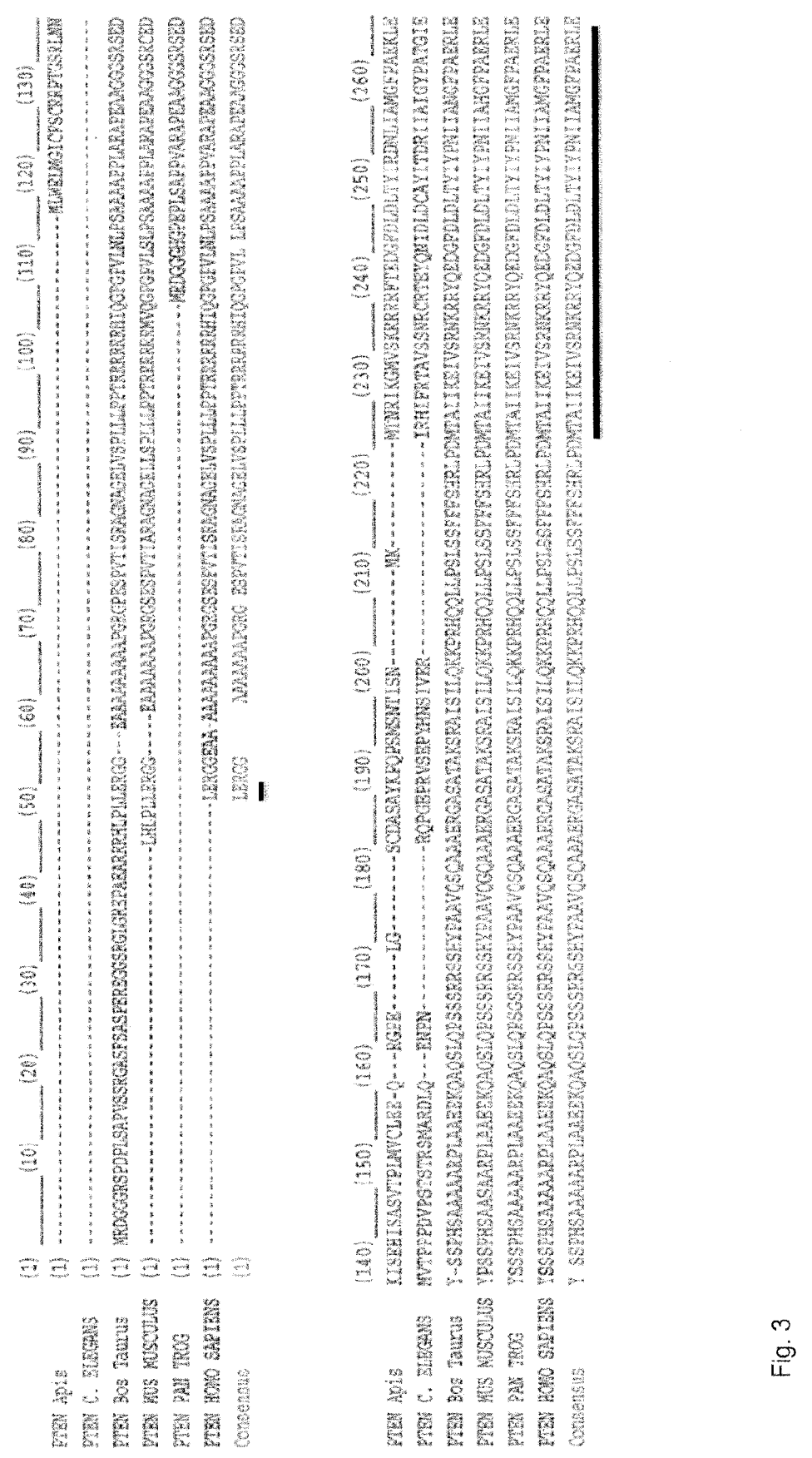

Alignment of other PTEN orthologs revealed that the translated sequence of the *Homo sapiens* UTR can be found in the open reading frames of PTEN from various species. *Pan troglodytes, Bos Taurus, Apis mellifera* and *Caenorhabditis elegans* all contain protein sequence homologous to the translated product of the *Homo sapiens* 5'UTR (FIG. 3). Furthermore, alignment of the *Homo sapiens* 5'UTR and *Mus musculus* PTEN 5'UTR showed extensive nucleotide homology (not shown). The *Mus musculus* 5'UTR was translated in frame with the canonical initiation codon for 522 base pairs and revealed a highly homologous protein sequence when compared to the translation of the *Homo sapiens* 5'UTR (FIG. 3). The homology of the 5'UTR and the actual presence of amino acid sequence derived from *Homo sapiens* 5'UTR in the translated proteins of other species is indicative of the evolutionary importance of this sequence.

PTEN mRNA can Initiate Translation from an Alternate Upstream Site.

Figure 4:
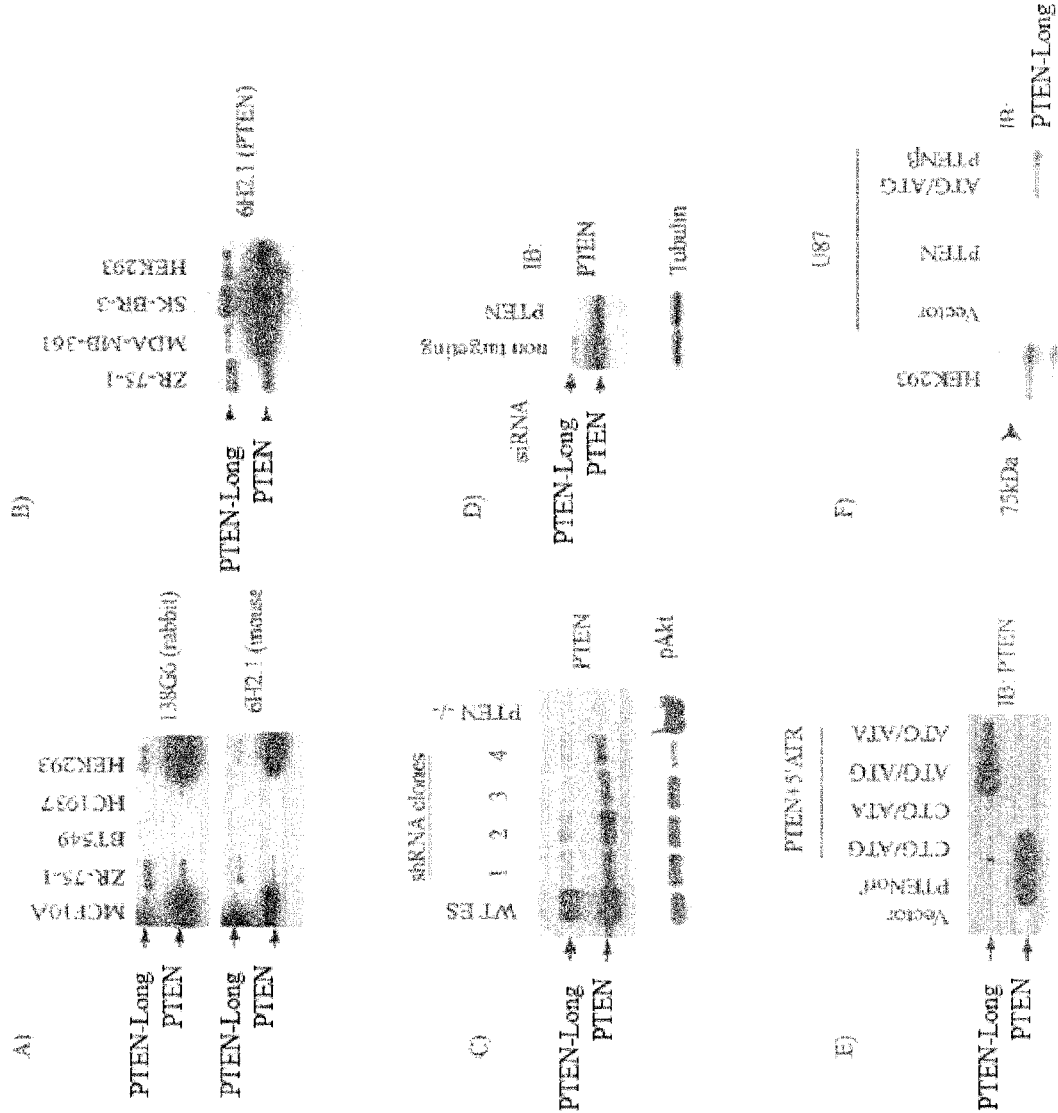
FIG. 4. Evidence for the existence of PTEN-long. A) Survey of different cell lines with two different PTEN antibodies. MCF10A and HEK293 are wildtype for PTEN. BT549 and HCC1937 are PTEN null and ZR-75-1 has a mutation in PTEN (L136); B) Further survey of different cell lines with a monoclonal antibody to PTEN which recognizes both PTEN and PTEN-long; C) Wt ES cells express large amount of PTEN-long. PTEN-long is sensitive to stable PTEN shRNA expression in these cells and is completely absent in PTEN knockout cells. pAkt levels for the most part inversely follow the level of PTEN; D) PTEN siRNA causes knockdown of both PTEN and PTEN-long in HEK293 cells. E) Exogneous expression of plasmids in the PTEN null PC3 cell line. PTEN-orf encodes solely the ORF from the start codon AUG (lane 2). Addition of the ATR (ATR=alternately translated region) is able to weakly translate PTEN-long (lane 3). Mutation of the upstream start site to ATG shifted the complement of protein to be completely PTEN-long (lane 5 and 6). Mutation of the ATG start codon to ATA abrogated the 55 kDa band (lane 4 and 6). E) An antibody raised to amino acids encoded by the 5'ATR and used on both a cell lysate from HEK293 as well as in the PTEN null U87 cell line overexpressing either the PTENorf or a plasmid encoding the 5'ATR (ATG/ATG). PTEN-long can be seen in cells only overexpressing the 5'ATR. A background band observed in U87 cells is present at the bottom of the blot.

Overexpression of the PTEN ORF generated a single protein band at 55 kDa. Inclusion of the 5'UTR resulted in a second larger protein band of approximately 70 kDa. A larger protein band in PTEN immunoblots was also present in a number of cell lines endogenously and was detectable by different monoclonal antibodies (FIG. 4). This larger protein band was also present in mouse wild type ES cells and was absent in PTEN knockout mouse ES cells and decreased in mouse ES clones stably expressing a PTEN shRNA (FIG. 4). Knockdown of human PTEN protein in HEK293 cells using siRNA also caused a knockdown of the 70 kDa protein.

Expression of a plasmid encoding the ORF of PTEN in the PTEN null PC3 cell line resulted in the generation of a 55 kDa protein. When plasmids that also encoded the 5'UTR were overexpressed, a 70 kDa protein was produced. Mutation of the upstream putative initiation codon from CTG to ATG (FIG. 1, "ATG/ATG") predominantly shifted the immunoblot pattern to the 70 kDa form (FIG. 4). The 55 kDa band was also confirmed as originating from the ATG start codon by mutagenesis (FIG. 4 "CTG/ATA").

Thus, the 5' UTR was sufficient to initiate translation of a longer form of PTEN. Accordingly, the 5' UTR was named 5'ATR for Alternately Translated Region and larger protein detected was named "PTEN-long".

An affinity purified polyclonal antibody was generated against amino acids translated from the 5'ATR and it was used to confirm the production of recombinant PTEN-long in overexpression studies as well as the endogenous form in HEK293 cells (FIG. 4). From the whole cell lysate immunoblot of HEK293 cells and overexpression studies in PC3 cells, there appeared to be multiple forms of PTEN-long, indicating either potential post-translational modifications, undocumented splice forms or even alternate initiation codons in the 5'ATR.

PTEN-Long Encodes a N-Terminal Signal Peptide

The N-terminal sequence of PTEN-long contains a long stretch of alanines which could be indicative of either a transmembrane sequence or a signal peptide. Analysis of the translated sequence using SignalIP 3.0 predicted with a high degree of probability (>95%) that the sequence contains a signal peptide (FIG. 5). A signal peptide is characteristically comprised of basic amino acids followed by a hydrophobic stretch. The putative hydphobobic transmembrane helix is broken by a proline and followed by a somewhat polar sequence. The sequence was also predicted to be cleaved, indicating that the protein should be released into the lumen of the ER.

PTEN is Glycosylated

Figure 6:
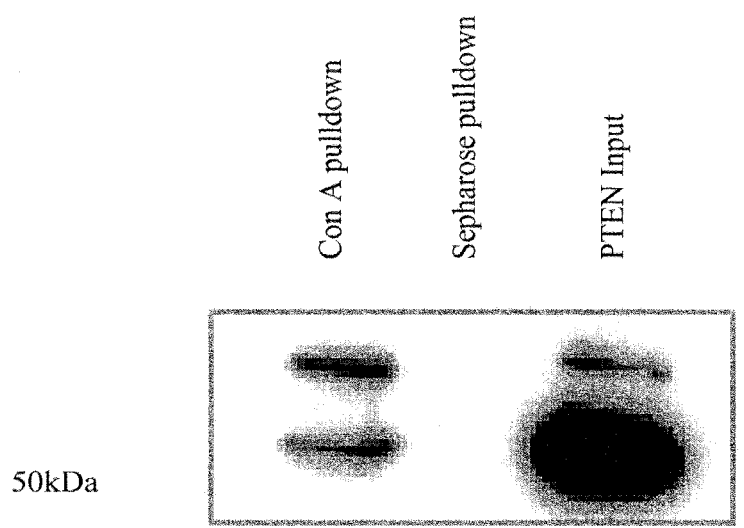
FIG. 6. Concanavalin A pulldown. HEK293 cells were lysed and concanavalin sepharose was used to pulldown glycosylated proteins. Eluates were resolved by SDS-PAGE and immunoblotted for PTEN (6H2.1). An enrichment in the PTEN-long can be observed in the pulldown versus input. Note enrichment of longer PTEN band. PTEN has multiple potential O-glycosylation sites, but only one N-glycosylation site. We used the lectin concanavalin-A, which binds sugar moieities, in a pulldown assay to determine whether a portion of the PTEN complement in HEK293 cells is glycosylated. We were able to purify a mixture of PTEN that was approximately 50% PTEN-long, a vast enrichment of PTEN-long over normal PTEN. This shows that PTEN-long is glycosylated and that either the cytoplasmic 55 kDa form of PTEN is glycosylated or that PTEN-long is cleaved extracellularly.

One of the hallmarks of secreted and extracellular proteins is the addition of complex sugar moieties in the golgi apparatus, a process known as glycosylation. Sugars can be added to asparagines at the consensus sequence N-X-S/T (X cannot be proline) via N-glycosylation (Gupta and Brunak 2002); the hydroxyl groups of serines, threonines and tyrosines can also be the target of what has been termed O-glycosylation (Julenius, Molgaard et al. 2005). PTEN has multiple O-glycosylation sites, but only one N-glycosylation site. Lectin concanavalin-A, which binds sugar moieties, was used in a pulldown assay to determine whether a portion of the PTEN complement in HEK293 cells was glycosylated. A mixture of PTEN that was approximately 50% PTEN-long (FIG. 6) was purified from these cells. This shows that PTEN-long is glycosylated and that either the cytoplasmic 55 kDa form of PTEN is glycosylated or that PTEN-long is cleaved extracellularly.

PTEN-Long Binds Heparan and is Found on the Cell Surface

Figure 7:
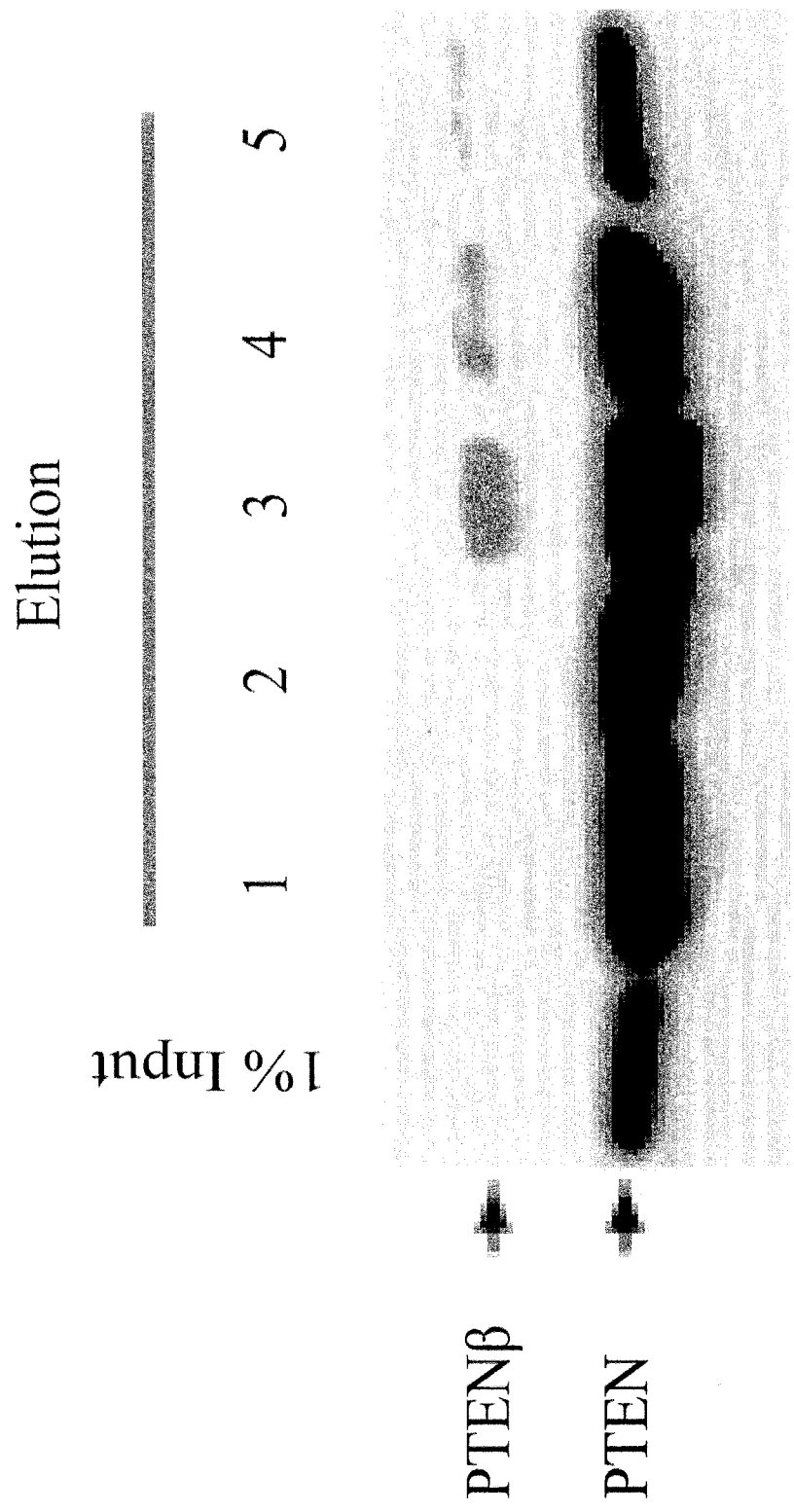
FIG. 7. PTEN and PTEN-β bind heparan. Mouse liver extract was passed through a 1 ml HiTrap Heparan sepharose (Amersham) column. The column was washed with 500 mM NaCl, and proteins were eluted with sequential column volumes of 1M NaCl. Fractions were analyzed by SDS-PAGE for PTEN using a PTEN monoclonal antibody. PTEN has previously been shown to have an affinity for highly negatively charged species, a property of PTEN which leads to its preference of the highly anionic PtdIns(3,4,5)P3 (Das, Dixon et al. 2003). As heparan is one of the most negatively charged biological molecules, we postulated that heparan was actually mediating the binding of PTEN to the extracellular matrix. Using protein extracts from mouse livers, we discovered that PTEN binds heparan with high affinity. Furthermore, continuous elution of PTEN from a heparin agarose column using 1M NaCl, also eluted PTEN-long.

PTEN bound a number of proteoglycans, such as syndecans and glypicans, which are found attached to the outer leaflet of the membrane. These proteoglycans are two of the most heparanated extracellular molecules (Blero, Zhang et al. 2005). PTEN has previously been shown to have high affinity for highly negatively charged species, a property of PTEN which leads to its preference of the highly anionic PIP3 (Das, Dixon et al. 2003). As heparan is one of the most negatively charged biological molecules, it was possible that heparan could mediate the binding of PTEN to the extracellular matrix. Using protein extracts from mouse livers, it was discovered that PTEN bound heparan with high affinity. Furthermore, continuous elution of PTEN from a heparin agarose column using 1M NaCl, also eluted PTEN-long (FIG. 7).

Figure 8:
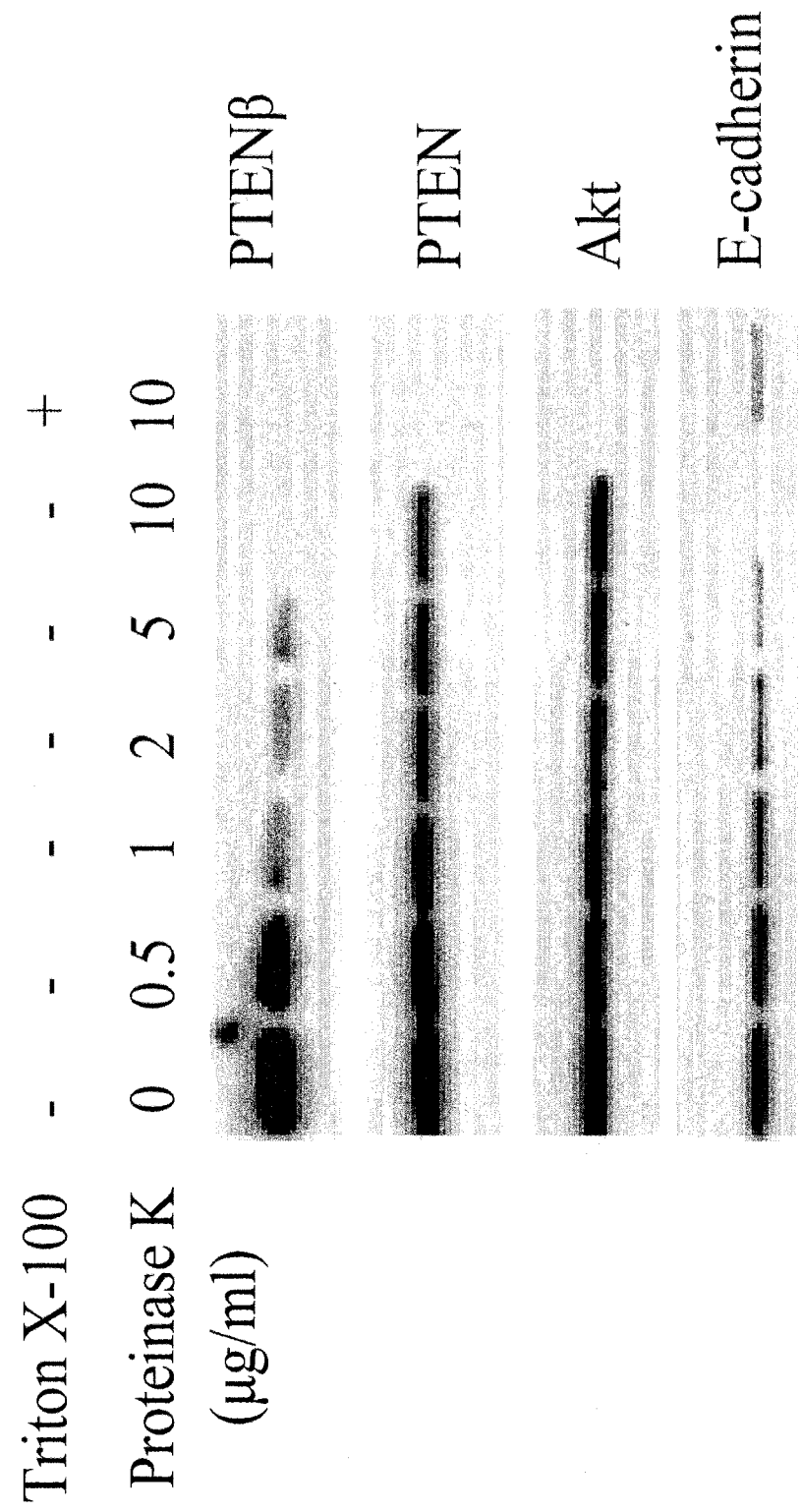
FIG. 8. Protease Protection Assay. HEK293 cells were resuspended in increasing concentrations of proteinase K. Triton at a final concentration of 0.2% was added to the reaction containing the highest concentration of Proteinase K. The reaction was stopped with PMSF and cell lysates were made in laemlli buffer. Lysates were resolved by SDS-PAGE on a 8% polyacrylamide gel and immunoblotted for PTEN (6H2.1), AKT, E-cadherin. The larger band of the PTEN immunoblot is designated PTEN-long. These data show that E-Cadherin and PTEN-long are largely on the cell surface.

PTEN-long stuck to the external surface of a cell membrane, should be sensitive to protease degradation. In the protease protection assay, live cells are incubated with a protease and only extracellular proteins are degraded as the lipid membrane is impermeable to the protease and serves to protect all intracellular proteins. HEK293 cells were removed from adherent culture by gentle agitation with PBS and suspended with increasing concentrations of Proteinase K. The reaction was stopped with PMSF and cells were lysed with laemlli buffer. PTEN-long displayed sensitivity to treatment with Proteinase K along with E-cadherin, which is a known extracellular protein (FIG. 8). PTEN on the other hand showed modest protease sensitivity, which indicates that some portion of the 55 kDa species is also extracellular (as it is glycosylated) or some cellular lysis occurred during the assay that exposed cytoplasmic PTEN to Proteinase K. A control with membrane permeabilizing triton was included to prove that PTEN could be degraded if exposed to Proteinase K. It remains to be seen whether this is PTEN proper or a cleaved form of PTEN-long which migrates at 55 kDa and retains the C-terminal epitope of the PTEN antibody. This data indicates that PTEN-long is on the cell surface.

Figure 9:
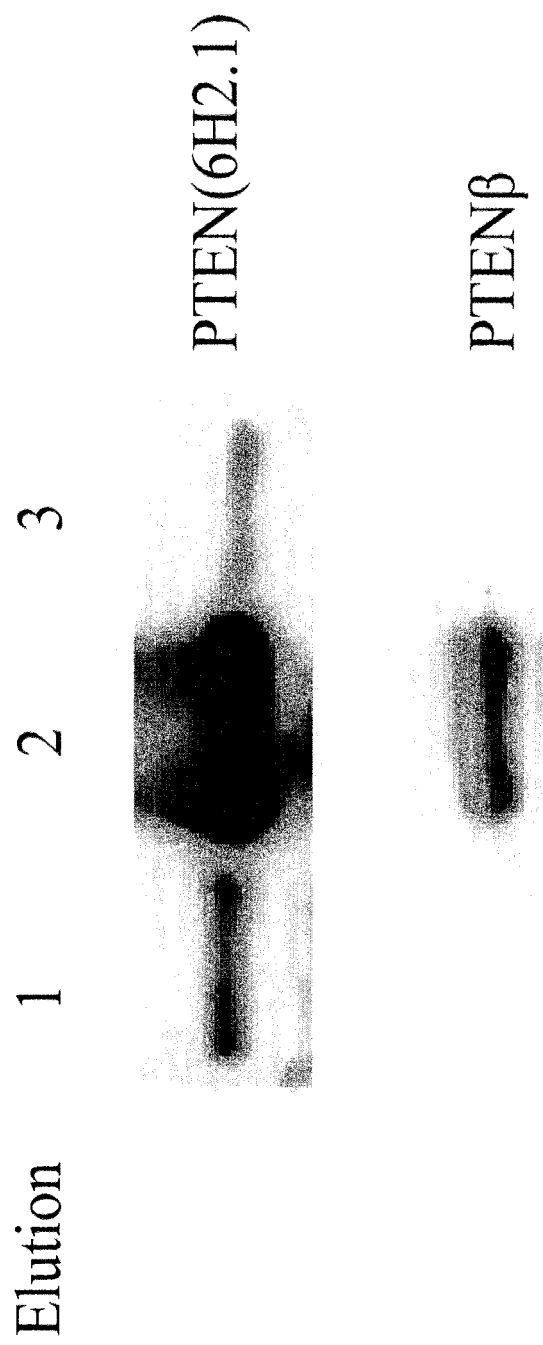
FIG. 9. High salt elution of PTEN and PTEN-long from heparin affinity purification of conditioned media. PTEN and PTEN-long can be eluted from a HiTrap Heparin (Amersham) column after affinity purification from conditioned media. Both a monoclonal antibody to the tail of PTEN (above) and an antibody specific to amino acids translated in the 5'ATR recognize a protein band of approximately 55 kDa in mass.

Soluble PTEN-Long is Secreted into Media.

the possibility that a portion of the protein is soluble and released into the cellular environment. Heparin sepharose was used to affinity purify PTEN-long from serum free media conditioned on HEK293 cells. Elution of the column revealed the presence of PTEN in the media migrating at a molecular weight of 50 kDa (FIG. 9). An immunoblot with the PTEN-long specific antibody revealed the same 50 kDa species, indicating that this protein retains sequence translated from the alternate start site and sequence from the C-terminal epitope of the PTEN monoclonal antibody. This strongly implies that the portion of PTEN observed to be 55 kDa is in fact cleaved translation product originating from the upstream start codon.

Secretion of PTEN into the media was further confirmed by overexpressing PTEN-long in HEK293 cells transfected with the ATG/ATG construct. These cells were used to produce serum free conditioned media overnight and the PTEN monoclonal antibody 6H2.1 was used to immunoprecipitate PTEN from 1 ml of media. The larger PTEN band was successfully immunoprecipitated from media along with the lower 55 kDa band. Because the protein was overexpressed, proper processing of the protein probably did not occur which resulted in the secretion of the full size 70 kDa PTEN.

PTEN is Found in Human Serum.

Figure 10:
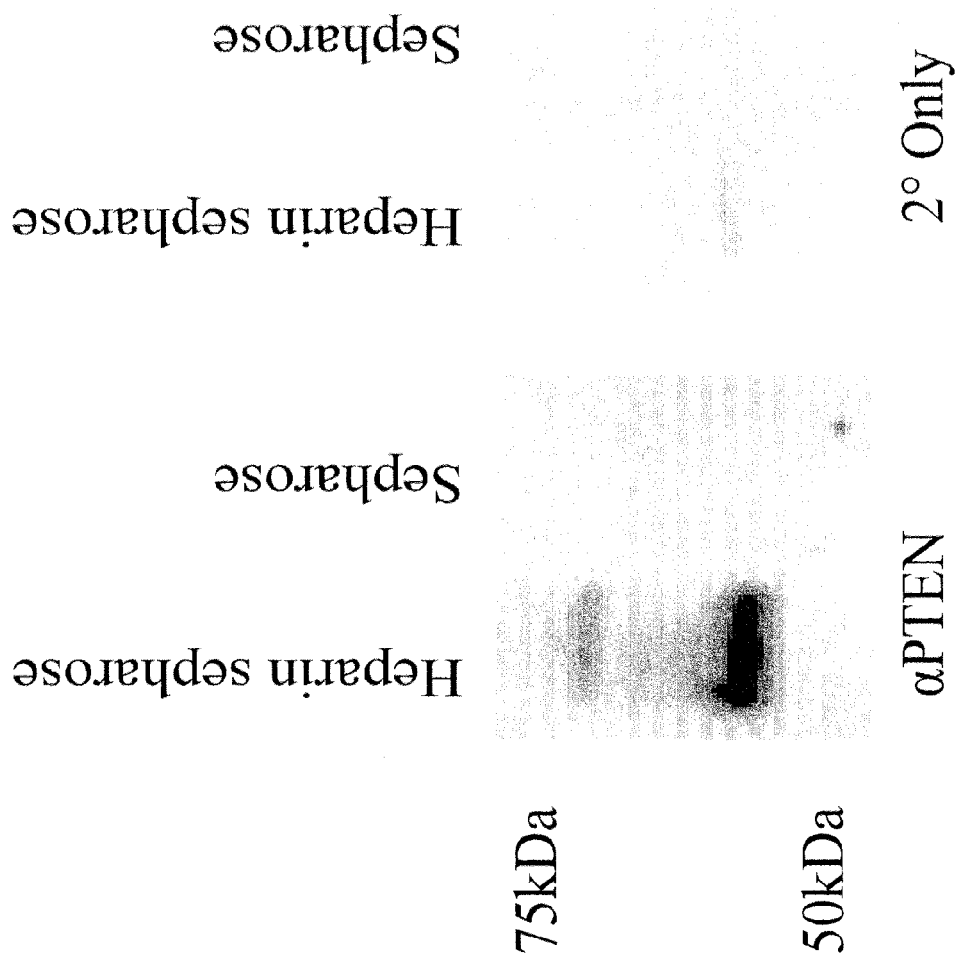
FIG. 10. Purification of PTEN from human serum. Human serum from AB blood was precleared of antibodies with protein A/G and subject to heparin sepharose. Eluates were resolved by SDS-PAGE and immunoblotted for PTEN or with secondary alone to control for heavy chain contamination.

One of the best sources of physiological secreted material is serum. Heparin sepharose was used to affinity purify PTEN from human serum. Human serum was spun down and filtered to remove particulate matter. It was then diluted 1:5 in BC150 and precleared extensively with protein A/G to remove IgG. The serum was batch incubated with a small amount of heparin sepharose. The heparin sepharose was eluted with laemmli buffer and the eluate was blotted for PTEN and for just secondary antibody alone to rule out heavy chain contamination. PTEN and PTEN-long were both found in human serum (FIG. 10).

Anti-Angiogenic Activity of PTEN-Long

Figure 11:
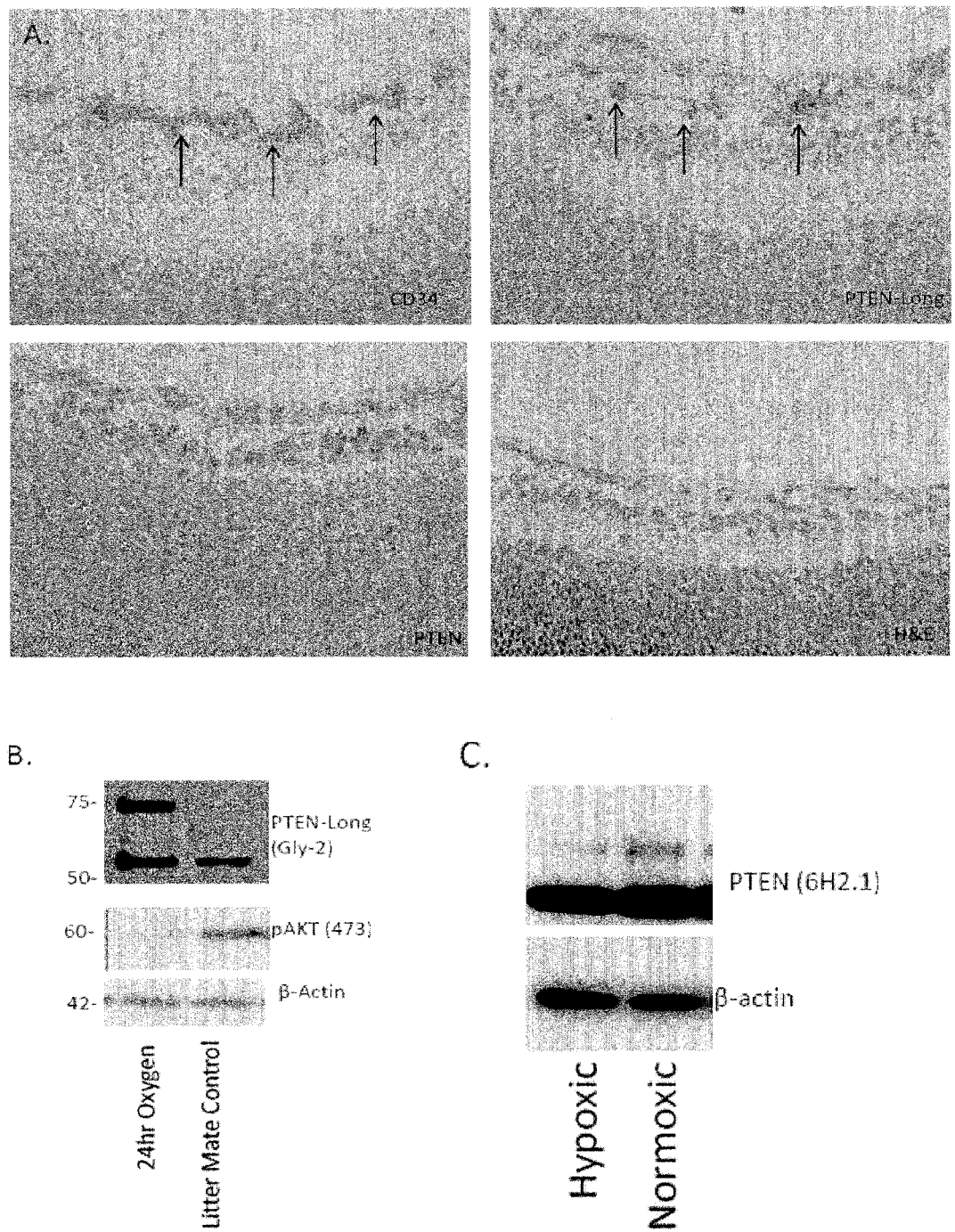
FIGS. 11A-11C. Anti-Angiogenic activity of PTEN-long. (A) PTEN-long is expressed in a subset of vessels and capillaries in the developing retina. This expression pattern is in stark contrast to that of the canonical form of PTEN and is consistent with a role for PTEN-long in induction of vascular regression that occurs in these regions. This correlation is strengthened by the marked up-regulation of PTEN-long, when this process of vascular regression has been induced by hyper-oxia as per the western blot of whole retina lysates on the top right (B), and by the loss of PTEN-long in endothelial cells under hypoxic conditions (C). These findings indicate the usefulness of PTEN-long as an anti-angiogenic therapy, for example in diabetic retinopathy, as well as hyper-proliferative vascular disorders. Arrows indicate CD34 and PTEN-long positive tissue (blood vessels).
Figure 12:
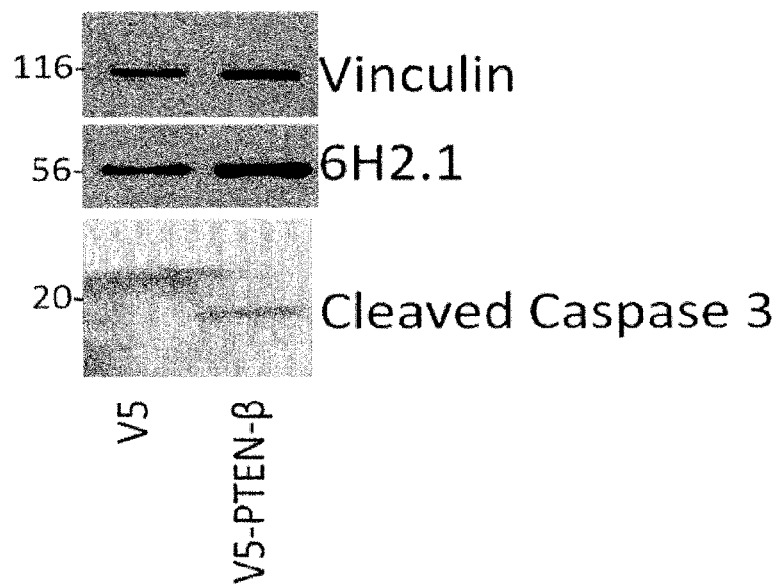
FIG. 12. Pro-apoptotic activity of PTEN-Long. Apoptosis was induced in MCF-10A mammary epithelial cells that were treated with purified PTEN-long for 24 hrs as indicated. Caspase 3 cleavage was indicative of apoptotic activity.

The anti-angiogenic role of PTEN-long is shown by the following: (1) PTEN-long is normally weakly expressed in the developing retina of the mouse but high level expression is seen in blood vessels undergoing involution/cell death during neonatal development (FIG. 11); (2) PTEN-long is found in apoptosing blood vessels in tumors. Furthermore, epithelial cells treated with PTEN-long, partially purified from transfected cells, inhibited cellular migration and induced apoptosis. (FIG. 12). Purified PTEN-long can also induce cell death associated with activation of apoptosis in U87, HUVEC endothelial cells, or 293 cells in culture, as measure by caspase-3 cleavage.

In Vivo Anti-Tumor and Anti-Angiogenic Activity of PTEN-Long

Figure 13:
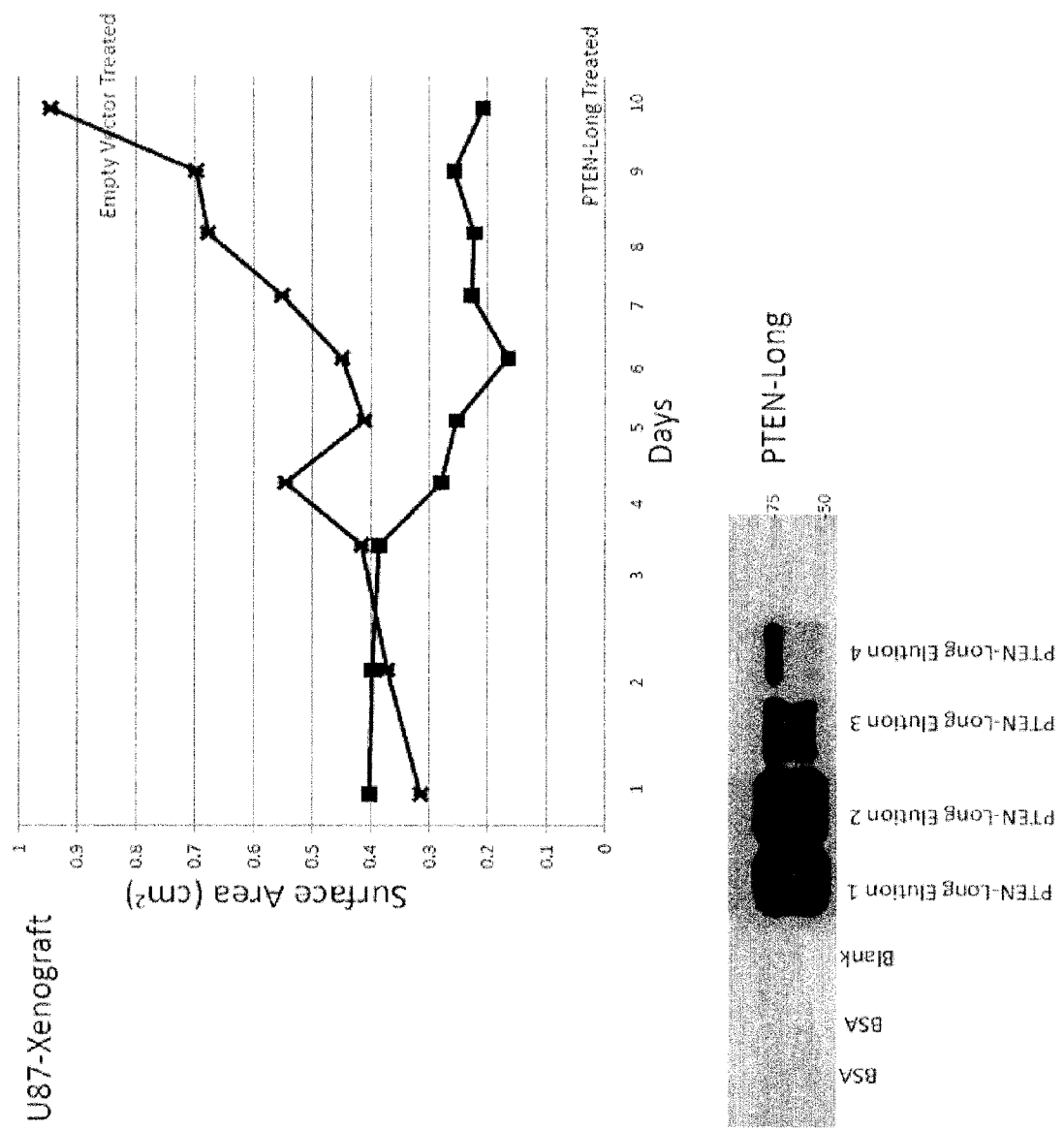
FIG. 13. Treatment of Mice with PTEN-Long. Graph of Tumor size as gauged by Caliper measurements over ten days of treatment, with either PTEN-long or an Empty Vector Control. 293 cells were transfected with ATG/ATG PTEN-long in the pcDNA3.1 His V5 vector. Cytoplasmic lysates were made 48 hr after transfection and passed over V5-antibody beads and eluted with V5 peptide. Western blot of the V5-bead purification eluates are shown below. Initial observation that PTEN-long could be used to treat Tumors. Xenografts were established using U87 glioblastoma cells (1 million) injected into the mammary fat pad of a scid mouse. Treatment was initiated approximately two weeks after transplantation.
Figure 14:
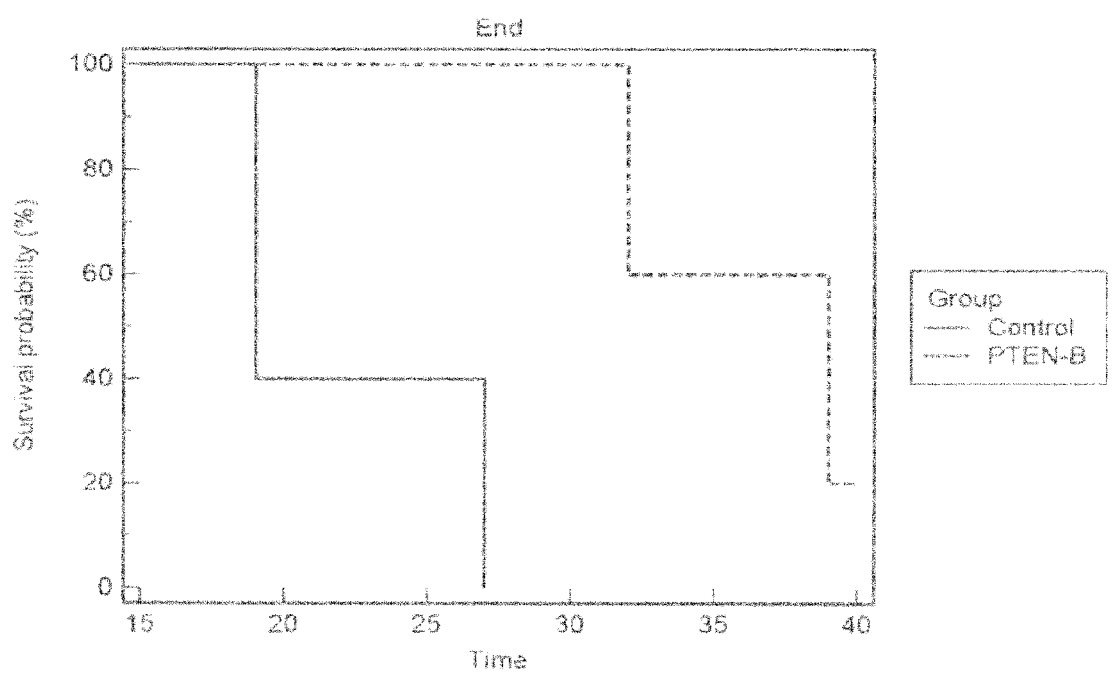
FIG. 14. Results of Treatment of Mice with PTEN-long. Graph shows the surviving fraction of mice (in days) treated with control and injections of PTEN-long for 14 days.
Figure 15:
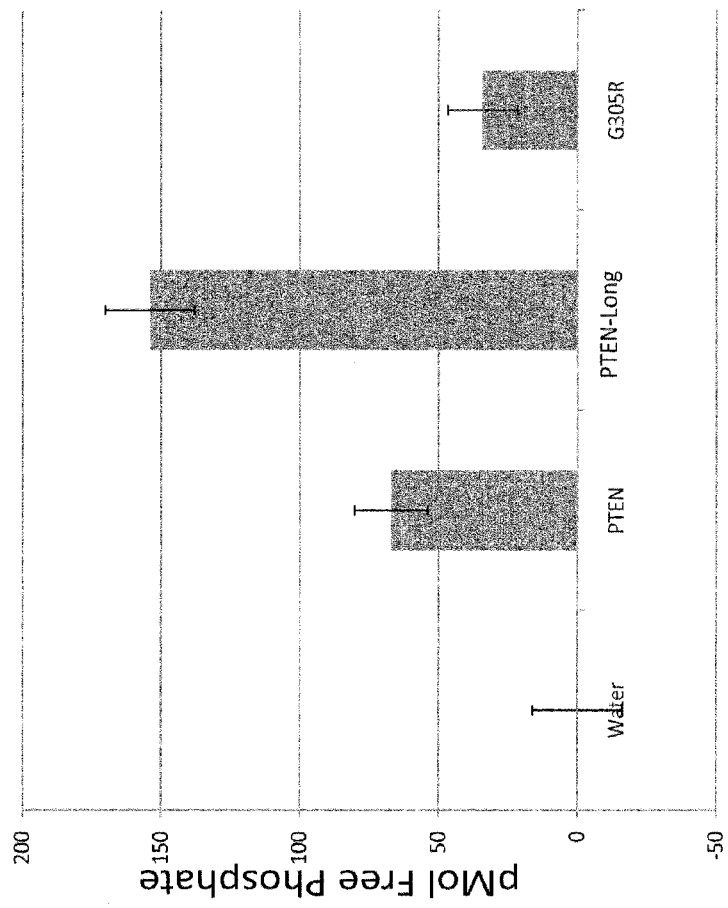
FIG. 15. Indicated constructs for PTEN (PTENorf lacking the 5'UTR), PTEN-long, and PTEN-long with a G to R mutation at amino acid 305, which is comparable to G129R mutation in PTENorf, were transfected into 293 cells. Using purified protein from these cells it was shown that PTEN-long is an active phosphatase, and that the PTEN-long G305R mutant (which is G129R in PTEN) reduces phosphatase activity.
Figure 16:
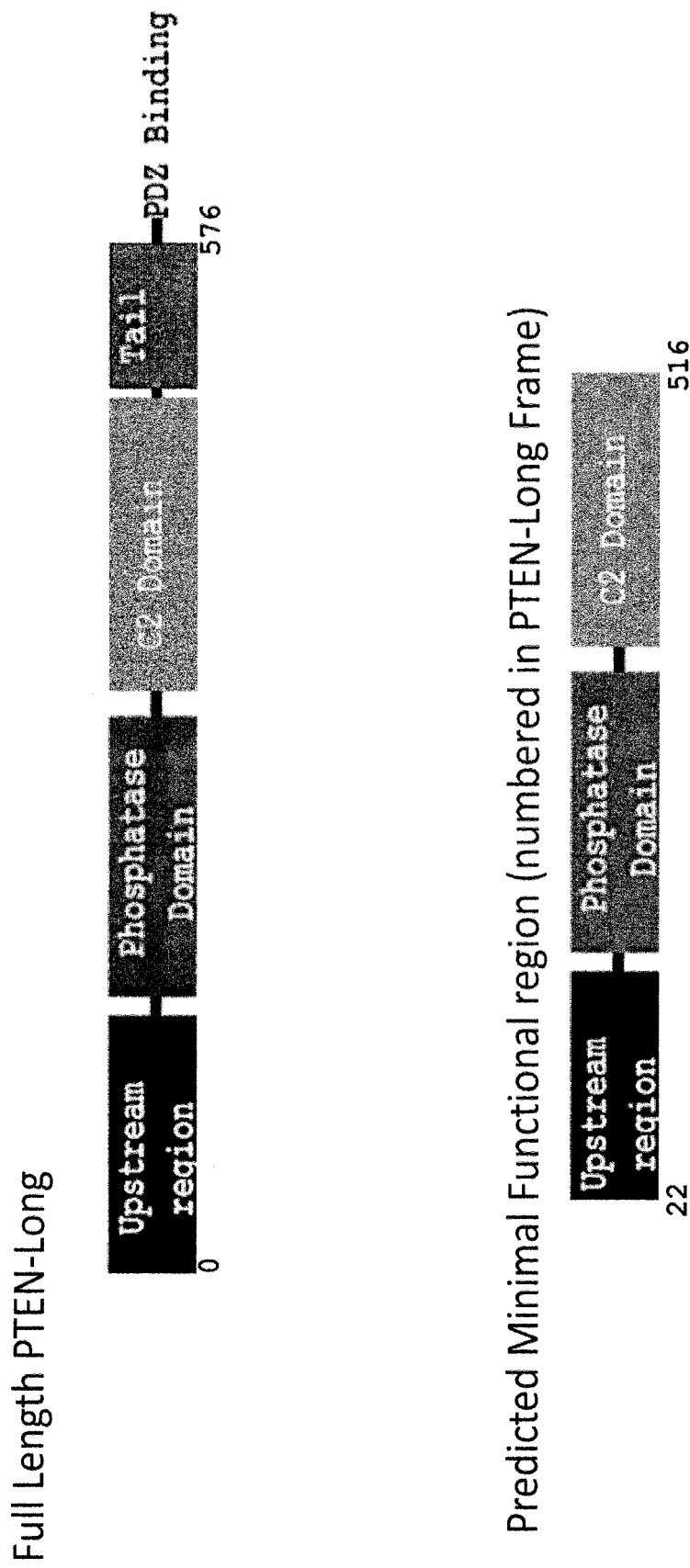
FIG. 16. Phosphatase activity is essential for PTEN-long activity is shown in the experiments with the PTEN-long (G305R) mutant. Based upon the PTEN literature it is known that truncations made inside the C2 domain destabilize the protein, and based upon the PTEN crystal structure it is believed interactions between the C2 domain and the phosphatase domains are critical for phosphatase activity. Therefore the minimal domain for PTEN-long activity at the C-terminus will require the C2 domain but not the tail. At the N-terminus the predicted cleavage site is at amino acid 21, and therefore the functional region of the protein is within this region. In regard to this it is important to note that when U87 tumors were treated in parallel with PTEN or with PTEN-long, no significant effect was observed from the PTEN treatment, only PTEN-long treatment.
Figure 17:
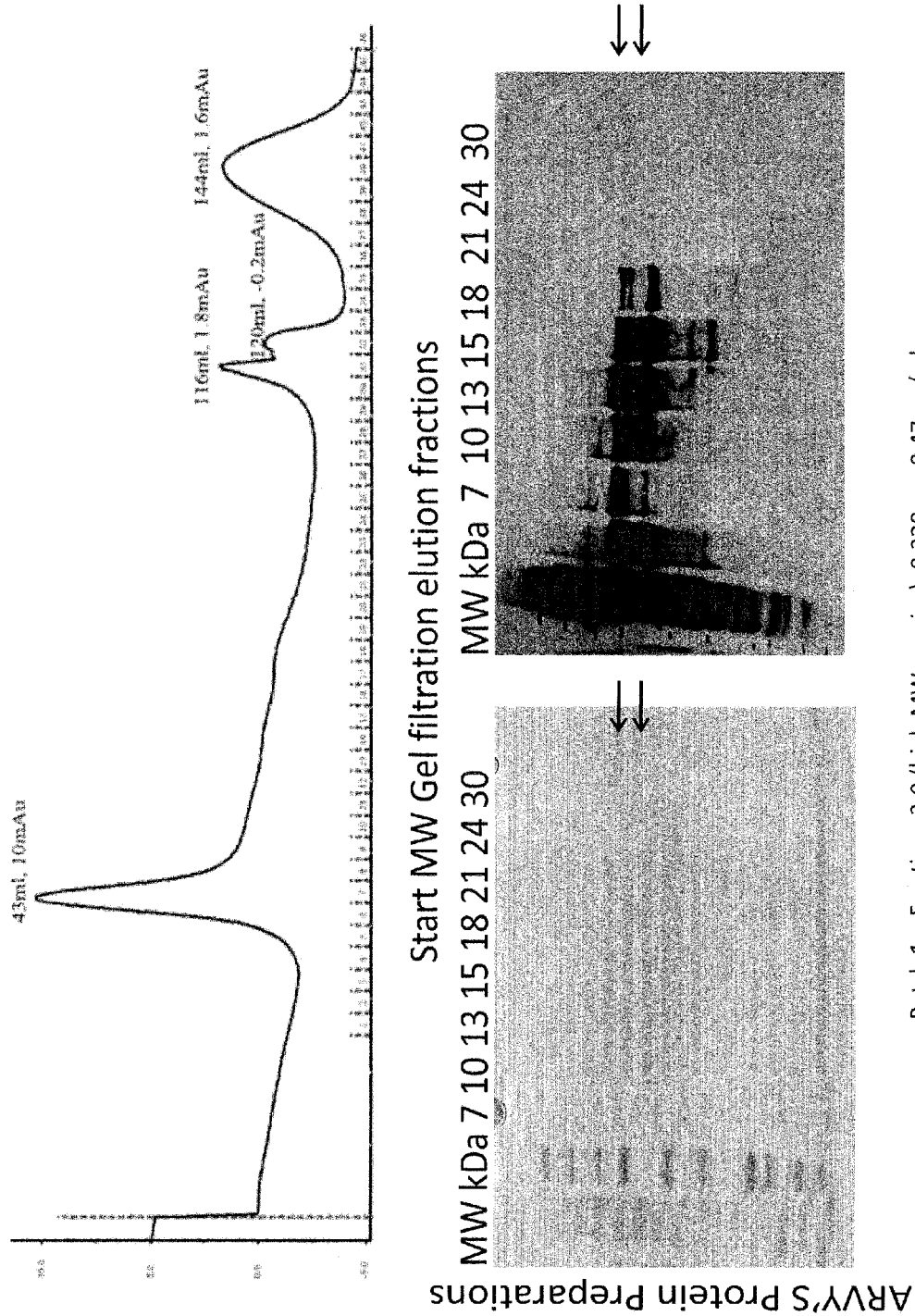
FIG. 17. Purification of PTEN-long from 293 cells transfected with ATG/ATG-PTEN long in the pcDNA3.1 expression vector with His and V5 tags. After Ni+ column elution, eluate was resolved in a gel filtration column. OD280 is shown with blue line. PTEN-long is enriched in fractions 7-18. Yield for this experiment was approximately 1 mg. Arrows indicate PTEN-long and altered migrating PTEN-long products.
Figure 18:
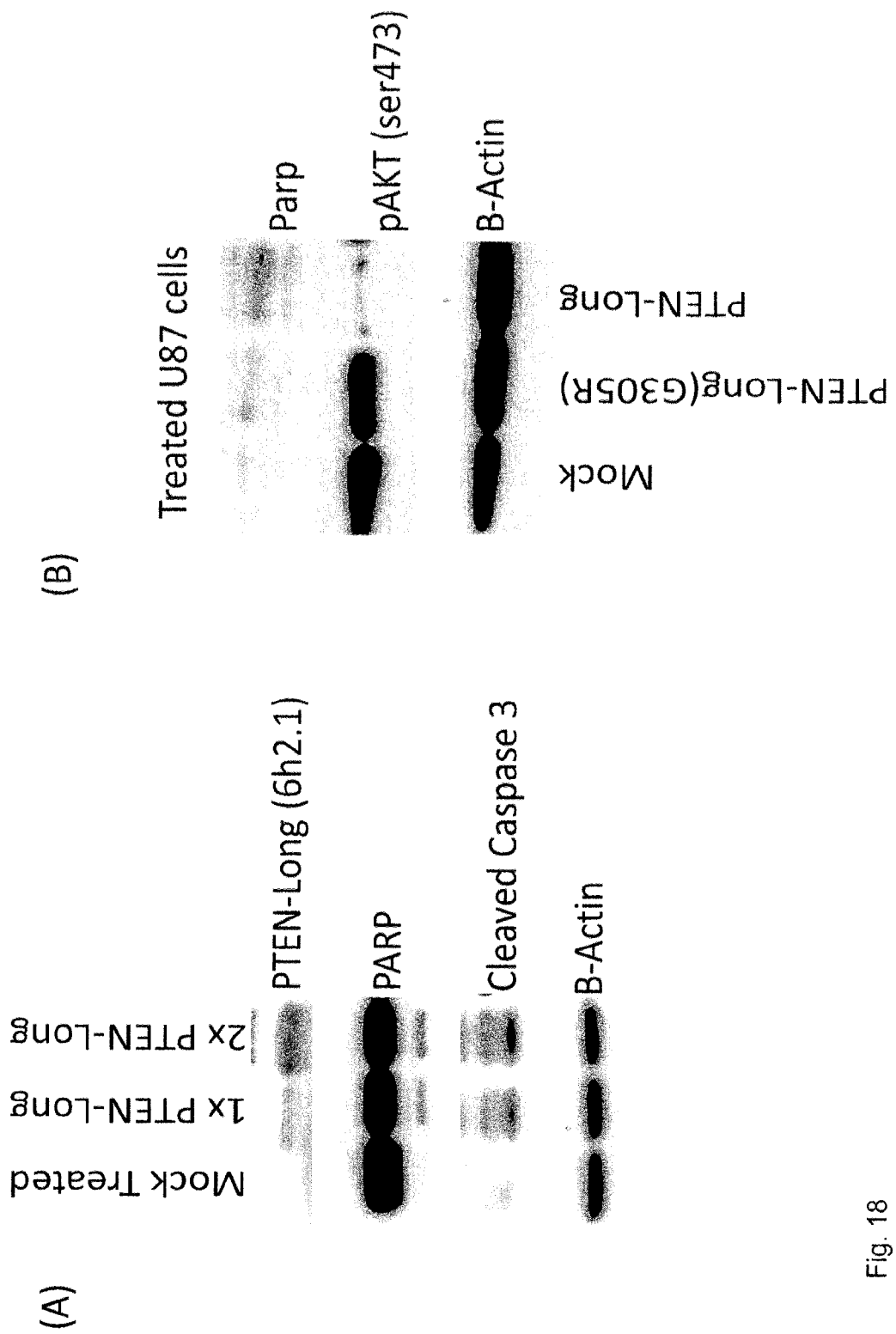
FIGS. 18A-18B. (A) Dose Response of LNCaP prostate cancer cells to PTEN-long purified protein using cell death as a readout (Protein was purified by ARVYS). 1× equals 0.33 microgram per ml. Cells were treated in media without growth factors. After 24 hr, cells were washed with serum free media and lysed in Laemmli sample buffer. Western blots for indicated proteins were performed. (B) U87 glioblastoma cells treated with PTEN-long, PTEN-long (G305R) or a Mock control show induction of apoptosis as indicated by cleavage of PARP and down regulation of pAKT signal at serine 473. These data further confirm that PTEN-long can induce apoptosis and reduce PI3K/AKT signaling.
Figure 19:
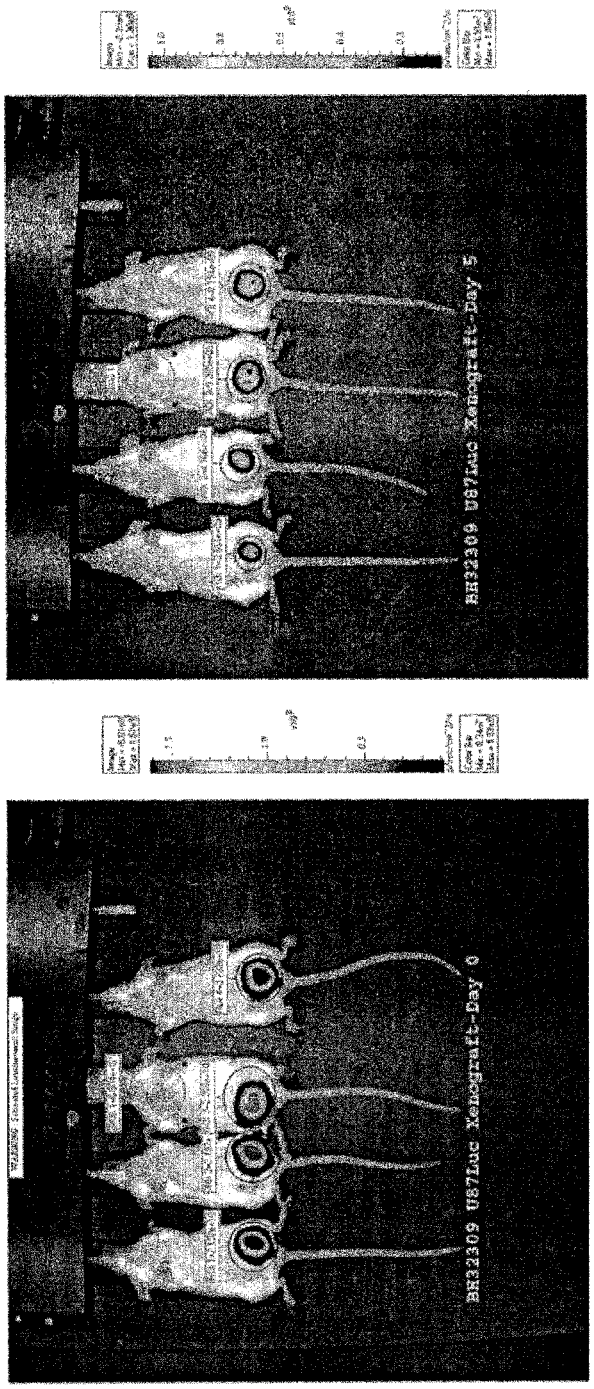
FIGS. 19A-19C. The AKTA purified PTEN-long protein was able to reduce tumor size over a five day period, as measured by both calipers and using a luciferase reporter in conjunction with a xenogen live animal imaging system. Mice were given ~0.05 mg PTEN-long per day for five days. Xenografts were established with 1 million U87 glioblastoma cells injected into the mammary fat pad that express luciferase due to infection with FUW-luciferase-neo. Mice were injected with luciferin intraperitoneally 10 minutes before imaging with the Xenogen Imaging System. (A) Luciferase measurements for 4 mice before (left panel) and on the fifth day of treatment (right panel). (B) Caliper measurements in $cm^2$ before and during the 5 days of treatment. (C) Photons detected by Xenogen system as imaged in panel. Standard error for four mice in cohort is shown. Student t-test for photons detected from day 0 to day 5.
Figure 19:
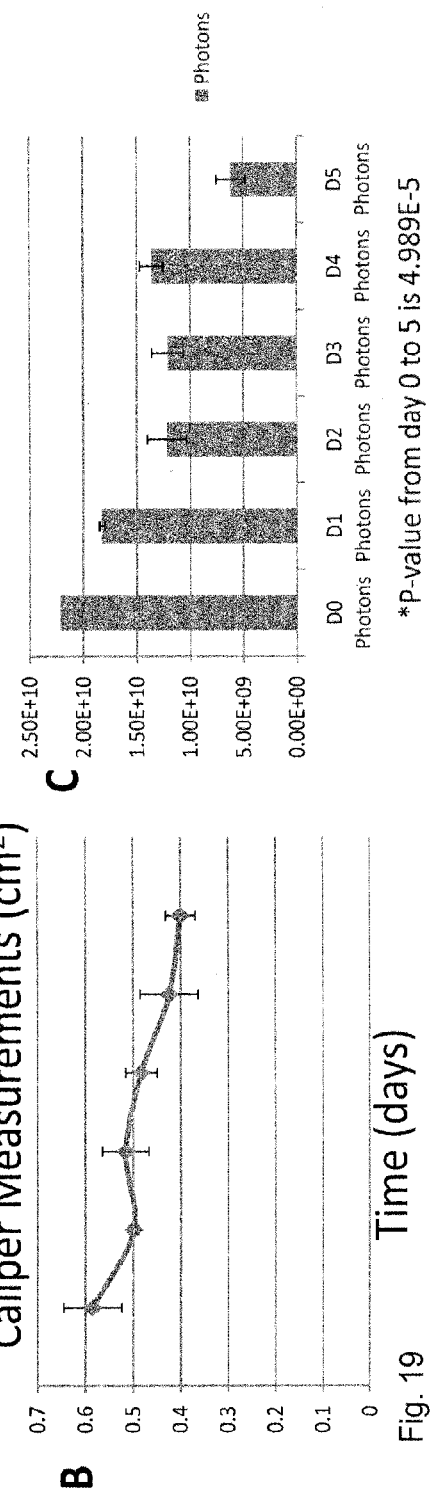
Figure 20:
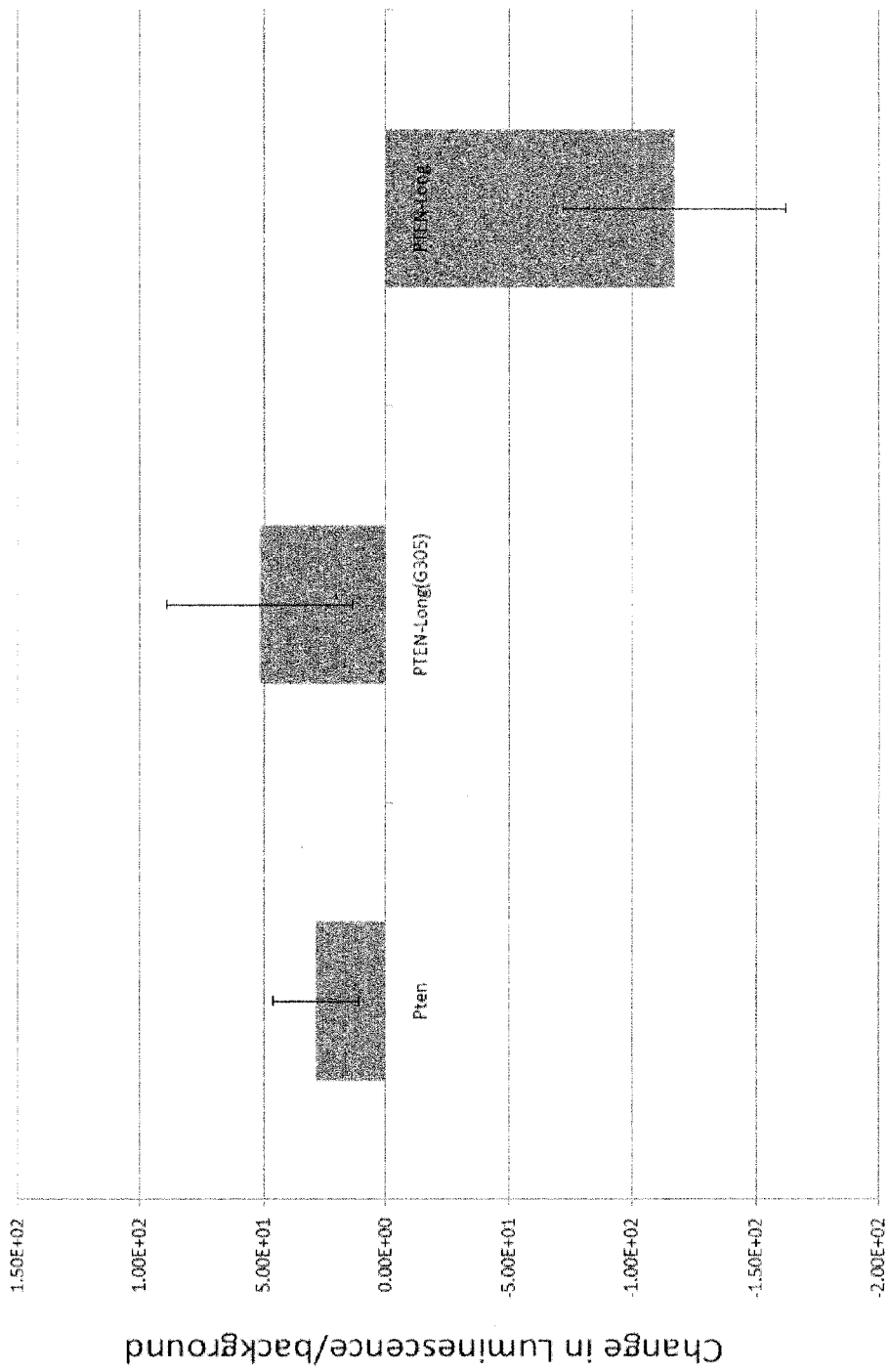
FIG. 20. In an independent experiment, U87 tumors were allowed to grow to 1.5 $cm^2$ before treatment with PTEN (orf-403 amino acids; n=5), PTEN-long (G305R; n=5) or wild type PTEN-long (n=4). After 5 days of treatment the average change luminescence shows a significant decrease for PTEN-long treated mice, but no decrease for the PTEN or PTEN-long (G305R) treated cohorts. Reduced luminescence correlated with reduced tumor size. These data demonstrate that PTEN-long requires the 5'ATR and phosphatase activity to function.
Figure 21:
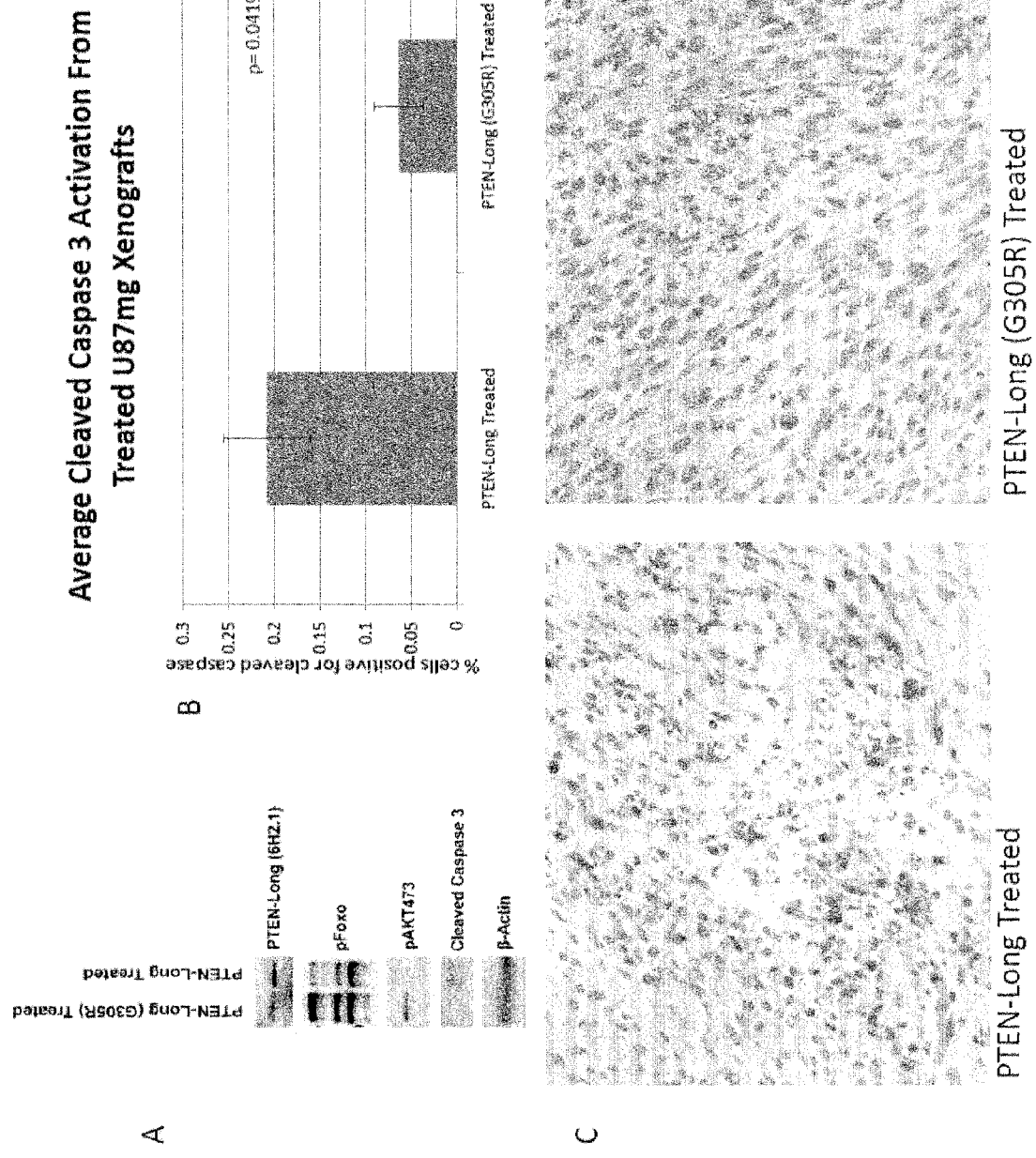
FIGS. 21A-21C. Analysis of PTEN-long-treated U87 xenografts demonstrates activation of apoptosis and inhibition of PI3K signaling. Tumors were treated for 5 days as above. (A) PTEN-long wild type and G305R treated tumors were harvested after 5 days of indicated treatment and lysed for western analysis. Wild type protein for PTEN-long was able to reduce FOXO and AKT phosphorylation and activate caspase-3 cleavage. (B) Representative tumors treated for 5 days as indicated were fixed in formalin and paraffin embedded. Sections were stained for an antibody that detects cleaved caspase-3, a marker of apoptosis. PTEN-long treated cells had a significant increase in percent of apoptotic cells P=0.0419, student's t-test. (C) Representative images of cleaved caspase-3 staining.
Figure 22:
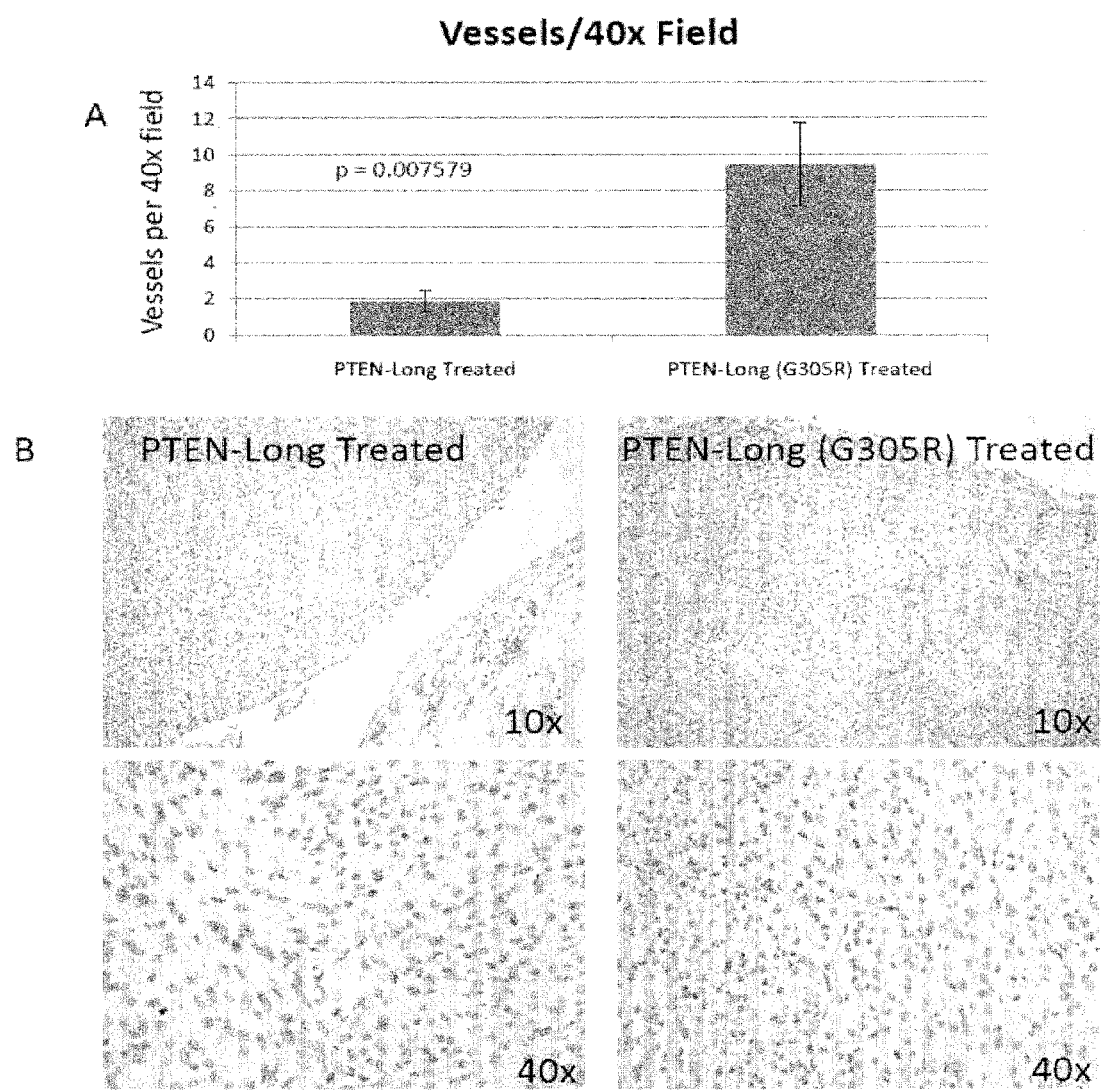
FIGS. 22A-22B. In the same tumor treated with PTEN-long for 5 days the number of blood vessels was greatly reduced. PTEN-long wild type and G305R treated tumors were harvested after 5 days of indicated treatment and were fixed in formalin and paraffin embedded. Sections were stained for an antibody that detects CD31, a marker of endothelial cells that line blood vessels. (A) PTEN-long treated cells had a significant reduction in the in the number of vessels per field of view (40× objective) P=0.007579, student's t-test. (B) Representative images of CD31 staining.
Figure 23:
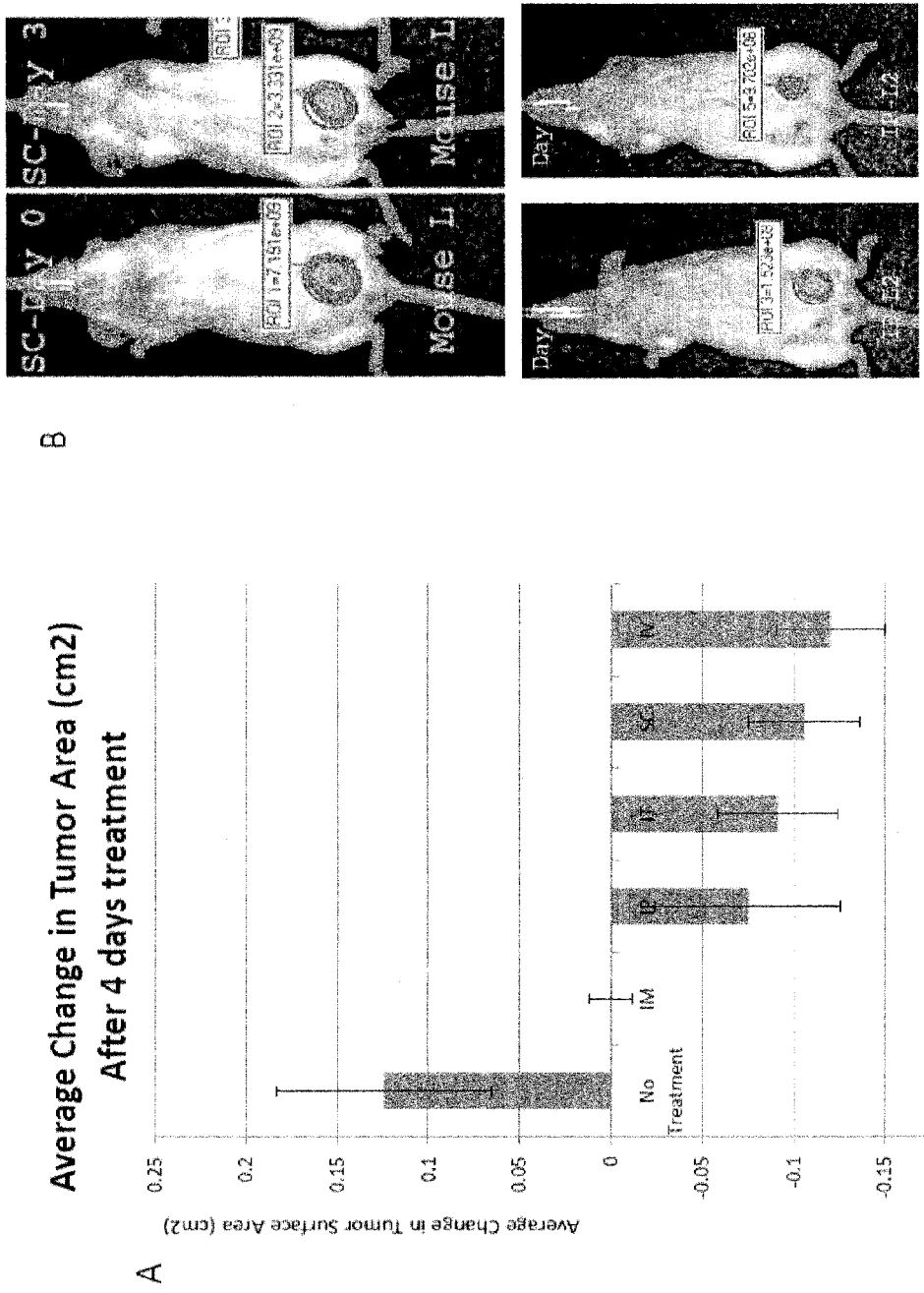
FIGS. 23A-23B. U87 xenografts were established in six groups (n=3/group) and were treated for four days with PTEN-long via Intra-Muscular (IM), Intra peritoneal (IP), Intra tumoral (IT), Subcutaneous (SC), Intravenous (IV) injections. (A) The average change in tumor size (CM2) from day 0 to day 4 as measured by caliper. (B) Representative images from xenogen imaging are shown on the right. From this data we can conclude that all of the methods of injection effected tumor growth as compared to the untreated mice, and that only the IM treated cohort showed a significantly decreased amount of regression.
Figure 24:
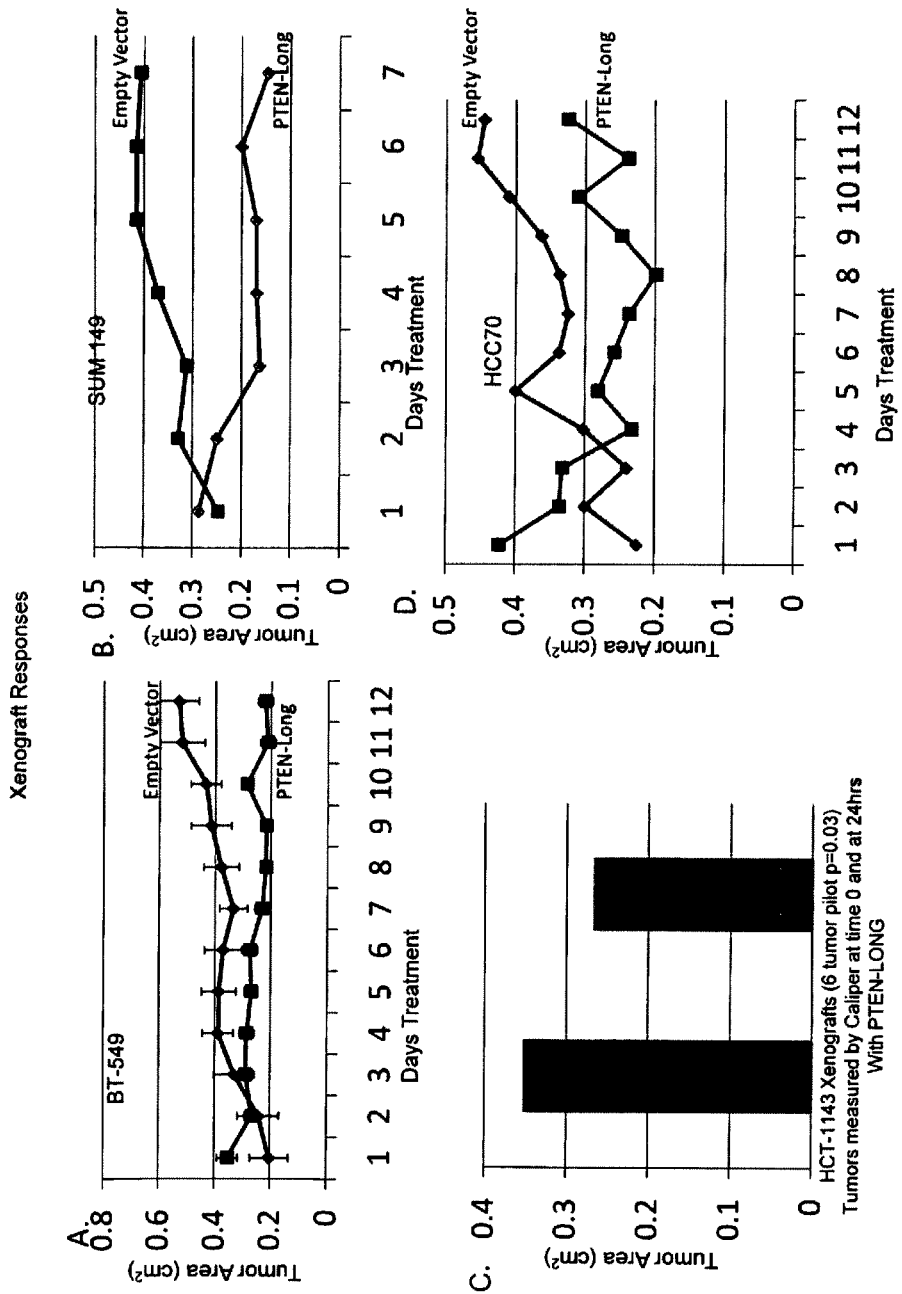
FIGS. 24A-24D. Xenograft experiments were run on 6 cell lines, from breast, brain, and prostate. Above are the changes charted in four breast cancer cell lines. (A, B, and D). Graphs of tumor surface area (cm$^2$) as measured by caliper over the indicated days of treatment. (C) The change in HCT-1143 cells is seen after only 24 hours of treatment. In all four cell lines there is a clear reduction in tumor size after treatment.
Figure 25:
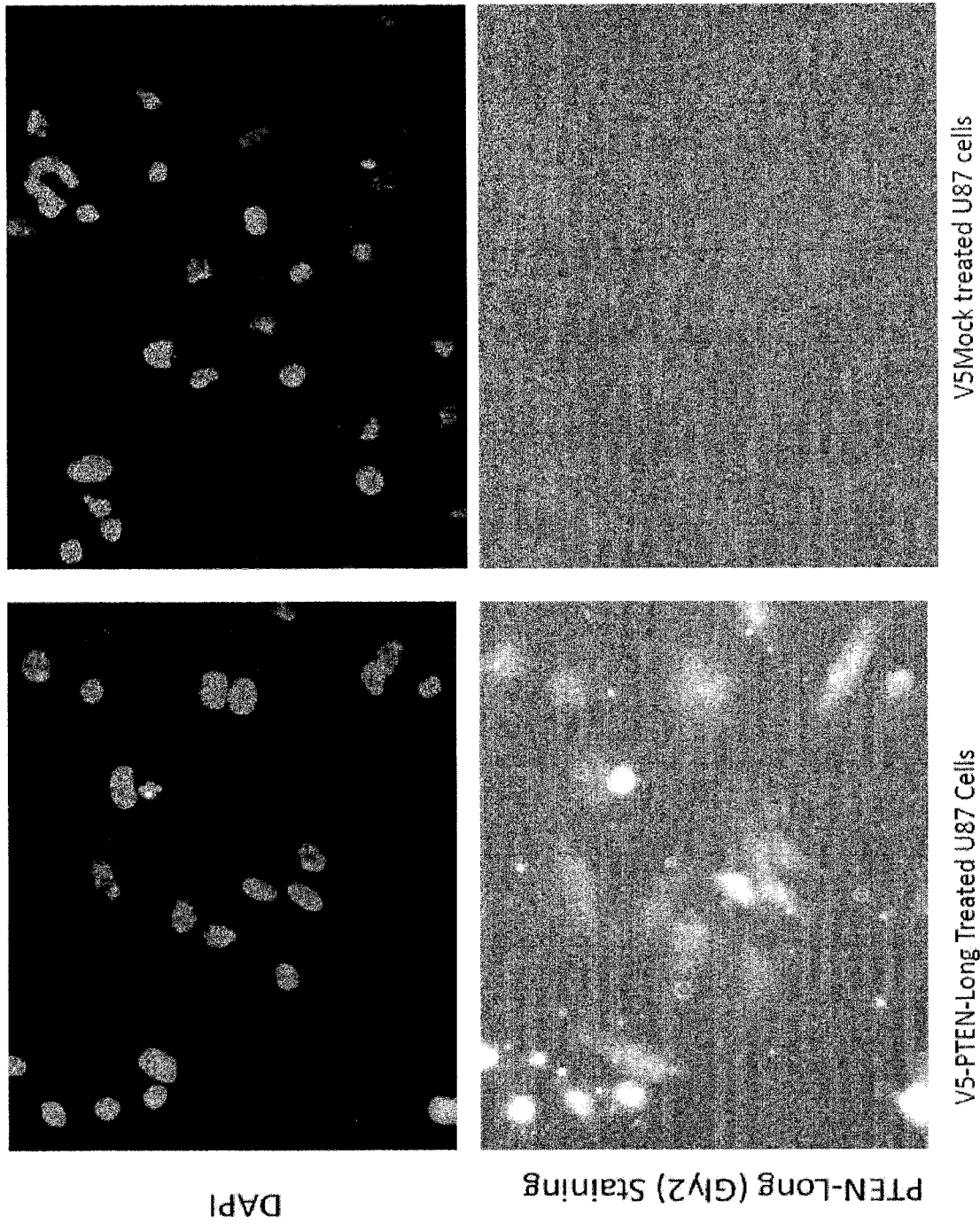
FIG. 25. PTEN-long binds to cells. PTEN-long protein was added to U87 cell media on ice for 10 minutes, fixed and then stained for PTEN-long with the antibody that recognizes it.
Figure 26:
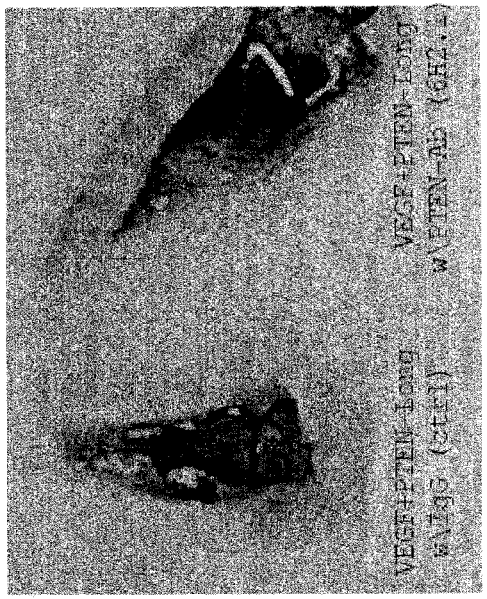
FIG. 26. Miles Assay: Induction of vascular permeability is inhibited by PTEN-long. This inhibition can be reversed by pre incubating the purified protein with PTEN antibody (6H2.1). PTEN-long is able to inhibit induction of Vascular permeability by VEGF. This induction could be restored by pre-incubating PTEN-long with antibody raised against PTEN, but not by control IgG.
Figure 26:
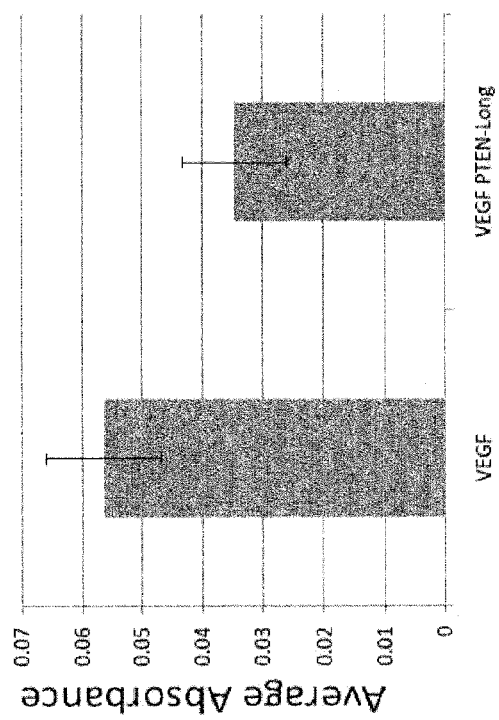
Figure 26:
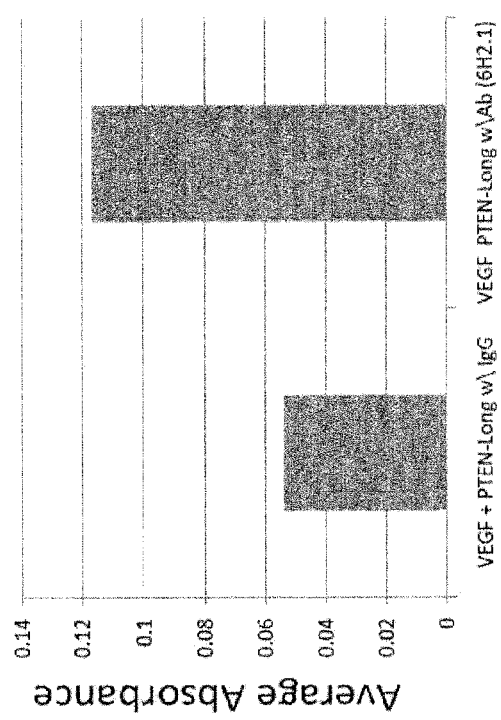

FIG. 13 shows treatment of Mice with PTEN-long (A) Mice (n=5) were injected with the glioblastoma cell line U87 to form xenografts at 2 sites (left and right) in mammary fat pads. After tumor engraftment one tumor was directly injected with PTEN-long and the contralateral tumor was not injected (w/PTEN-long). A control set of 5 mice also injected (Empty Vector) with a preparation of mock purified protein derived from cells transfected with empty vector. Again, the contralateral tumor was not injected (w/Empty Vector). Mice were treated on days 1- and days 13-14. Largest diameter (cm) was measured with calipers on indicated days. Mice were sacrificed when tumor volume reached ≥1 cm. (B) Protein was prepared by transfection of PTEN-long expression vector into 293 cells and partially purified using V5 affinity resin followed by elution with V5 peptide. FIG. 14 Shows the surviving fraction of mice (in days) treated with control injections of PTEN-long for 14 days.

Retinal Staining

Staining for PTEN-long and Blood vessels in the p7 murine retina revealed that PTEN-long selectively stained hyaloid vessels which are beginning to regress at this point in murine retinal vascular development. The antibody to PTEN-long was directed against the epitope: N-PRHQQLLPSLSSFFF-SHRLPD-C (SEQ ID NO:3). Vessel staining was with BS1-lectin.

Purification

In one method for purification of PTEN-long 293 cells were transfected with ATG/ATG PTEN-long and cell lysate was passed over a Ni+ affinity column. PTEN-long was consistently purified using a Ni+ column on the AKTA Purifier using imidazole elution buffer.

Tumor Regression

Xenografts of U87 cells transfected prior to injection with either PTEN (orf 403 amino acid) or PTEN-long. At 7 days post injection there is a reduction in the mammary blood vessels in the PTEN-long over-expressing cohort as compared to the PTEN over-expressing cohort (n=4 of 4). This suggests that PTEN-long can affect the tumor environment.

Discussion

A second larger protein band in PTEN immunoblots from cell lysates and tissue was regularly observed. Evidence confirming that the larger band is PTEN includes: the larger protein bands were detected by different PTEN monoclonal antibodies; the larger protein is absent when cells are treated with siRNA against PTEN or the PTEN locus is knocked out in mice. The 5'UTR of PTEN was observed to be in frame for more than 700 base pairs with the classic start codon of PTEN. Furthermore, there is a CUG codon 522 base pairs upstream of PTEN, which, if translated, could account for the size of the larger protein band in PTEN immunoblots. Though it is not associated with a strong Kozak sequence, it does retain the −1 cytosine and +1 guanosine sequence. When translated and added to the PTEN ORF, a protein of approximately 70 kDa should be created, which is the molecular mass of the larger PTEN band that has been observed.

The translation of this sequence already existed in a number of PTEN orthologs within their actual coding sequence. The mouse 5'UTR was also inspected because a similar band in mouse tissue lysates had been observed. The mouse 5'UTR nucleotide sequence was highly homologous to the *Homo sapiens* 5'UTR and similarly in frame with the start codon. Two potential alternate start codons exist at −522 and −516 and translation of this sequence from those sites reveals amino acid sequence 90%+ homologous to the *Homo sapiens* sequence. The conservation of this putative protein is remarkable and demonstrated an evolutionary importance to this sequence. In order to better describe this sequence, it was renamed the 5'ATR or alternately translated region of PTEN to describe its potential for translation.

A plasmid was constructed in which the open reading frame of PTEN was cloned together with the 5'ATR and the expression of this recombinant PTEN was compared to the canonical 403 amino acid-producing open reading frame alone. The inclusion of the 5'ATR generated a second, higher PTEN protein band which migrated at approximately 70 kDa as compared to expression plasmids containing just the canonical ORF of PTEN, which created a single band migrating at 55 kDa. The larger protein accounted for only a minor portion of the total protein translated; however, mutation of the putative start site to ATG shifted the protein ratio to predominantly the larger form.

The conservation of protein sequence from the 5'ATR indicated that it was more than an artifact of evolution. The N-terminus contained a stretch of aliphatic amino acids which were predicted to be a transmembrane sequence. Use of Prosite and Signal 3.0IP predicted that the N-terminus of PTEN-long was a signal peptide with a protease cleavage site directly following it.

An in vivo protease protection assay was used to test if PTEN-long was located on the extracellular surface of the cells. PTEN-long showed progressive degradation with increasing amounts of extracellular protease, while PTEN did not, indicating that at least some of PTEN-long is extracelluar and at least in part attached to outer leaflet of the cell membrane. This is a most intriguing result given the implication of an active lipid phosphatase on the outer leaflet of the cell membrane. Two families of outer membrane bound proteoglycans, glypicans and syndecans, were previously identified in a PTEN protein complex.

The presence of PTEN on the cell surface does not exclude the possibility of a soluble secreted PTEN. Syndecans and glypicans are two of the most heavily heparanated proteoglycans. Heparan is a highly negatively charged glycosaminoglycan and PTEN has been shown to have an affinity for anions, in part explaining the choice of the highly negatively charged PIP3 as its substrate. Optimization experiments of PTEN purification from mouse liver revealed that both PTEN and PTEN-long could be purified using a heparin sepharose column. Furthermore, a protein of approximately 50 kDa was purified, from serum free media conditioned on HEK293 cells, using a heparin sepharose column. The purified protein was recognized by a monoclonal antibody specific against PTEN and a polyclonal antibody against unique amino acid residues present in PTEN-long. Previously the PTEN-long antibody only recognized a protein band around 70 kDa. The observation that both antibodies could recognize the one band indicates that proteolytic processing is probably occurring and that the protein observed by immunoblot is a fragment of PTEN which retained the epitopes of both antibodies. Both PTEN and PTEN-long could also be purified from human serum using heparin affinity purification.

A body of literature over the past 10 years has accumulated assuming the sequence of PTEN. Here proof for the existence of a novel form of PTEN which is translated from an alternate site and is secreted to both the outer leaflet as well as extracellular spaces.

The in vivo results show that PTEN-long is a novel antitumor compound that is normally present in human serum and which has anti-angiogenic and pro-apoptotic properties.

REFERENCES

Acland, P., M. Dixon, et al. (1990). "Subcellular fate of the int-2 oncoprotein is determined by choice of initiation codon." Nature 343(6259): 662-5.

Alberts, B. (2002). Molecular biology of the cell. New York, Garland Science.

Baker, S. J. (2007). "PTEN enters the nuclear age." Cell 128(1): 25-8.

Blero, D., J. Zhang, et al. (2005). "Phosphatidylinositol 3,4,5-trisphosphate modulation in SHIP2-deficient mouse embryonic fibroblasts." Febs J 272(10): 2512-22.

Blobel, G., P. Walter, et al. (1979). "Translocation of proteins across membranes: the signal hypothesis and beyond." Symp Soc Exp Biol 33: 9-36.

Bonneau, D. and M. Longy (2000). "Mutations of the human PTEN gene." Hum Mutat 16(2): 109-22.

Di Cristofano, A., B. Pesce, et al. (1998). "Pten is essential for embryonic development and tumour suppression." Nat Genet 19(4): 348-55.

Eng, C. (2003). "PTEN: one gene, many syndromes." Hum Mutat 22(3): 183-98.

Florkiewicz, R. Z. and A. Sommer (1989). "Human basic fibroblast growth factor gene encodes four polypeptides: three initiate translation from non-AUG codons." Proc Natl Acad Sci USA 86(11): 3978-81.

Fraser, M. M., X. Zhu, et al. (2004). "Pten loss causes hypertrophy and increased proliferation of astrocytes in vivo." Cancer Res 64(21): 7773-9.

Gupta, R. and S. Brunak (2002). "Prediction of glycosylation across the human proteome and the correlation to protein function." Pac Symp Biocomput: 310-22. Hann, S. R. (1994). "Regulation and function of non-AUG-initiated proto-oncogenes." Biochimie 76(9): 880-6.

Hann, S. R., M. Dixit, et al. (1994). "The alternatively initiated c-Myc proteins differentially regulate transcription through a noncanonical DNA-binding site." Genes Dev 8(20): 2441-52.

Hann, S. R. and R. N. Eisenman (1984). "Proteins encoded by the human c-myc oncogene: differential expression in neoplastic cells." Mol Cell Biol 4(11): 2486-97.

Hann, S. R., M. W. King, et al. (1988). "A non-AUG translational initiation in c-myc exon 1 generates an N-terminally distinct protein whose synthesis is disrupted in Burkitt's lymphomas." Cell 52(2): 185-95.

Hann, S. R., K. Sloan-Brown, et al. (1992). "Translational activation of the non-AUG-initiated c-myc 1 protein at high cell densities due to methionine deprivation." Genes Dev 6(7): 1229-40.

Hershey, J. W. (1991). "Translational control in mammalian cells." Annu Rev Biochem 60: 717-55.

Julenius, K., A. Molgaard, et al. (2005). "Prediction, conservation analysis, and structural characterization of mammalian mucin-type O-glycosylation sites." Glycobiology 15(2): 153-64.

Kiefer, P., P. Acland, et al. (1994). "Competition between nuclear localization and secretory signals determines the subcellular fate of a single CUG-initiated form of FGF3." Embo J 13(17): 4126-36.

Kozak, M. (1989). "Context effects and inefficient initiation at non-AUG codons in eucaryotic cell-free translation systems." Mol Cell Biol 9(11): 5073-80.

Kozak, M. (1990). "Downstream secondary structure facilitates recognition of initiator codons by eukaryotic ribosomes." Proc Natl Acad Sci USA 87(21): 8301-5.

Kozak, M. (1991). "An analysis of vertebrate mRNA sequences: intimations of translational control." J Cell Biol 115(4): 887-903.

Kwabi-Addo, B., D. Giri, et al. (2001). "Haploinsufficiency of the Pten tumor suppressor gene promotes prostate cancer progression." Proc Natl Acad Sci USA 98(20): 11563-8.

Lee, J. O., H. Yang, et al. (1999). "Crystal structure of the PTEN tumor suppressor: implications for its phosphoinositide phosphatase activity and membrane association." Cell 99(3): 323-34.

Li, J., L. Simpson, et al. (1998). "The PTEN/MMAC1 tumor suppressor induces cell death that is rescued by the AKT/protein kinase B oncogene." Cancer Res 58(24): 5667-72.

Maehama, T. and J. E. Dixon (1998). "The tumor suppressor, PTEN/MMAC1, dephosphorylates the lipid second messenger, phosphatidylinositol 3,4,5-trisphosphate." J Biol Chem 273(22): 13375-8.

Petrocelli, T. and J. M. Slingerland (2001). "PTEN deficiency: a role in mammary carcinogenesis." Breast Cancer Res 3(6): 356-60.

Prats, H., M. Kaghad, et al. (1989). "High molecular mass forms of basic fibroblast growth factor are initiated by alternative CUG codons." Proc Natl Acad Sci USA 86(6): 1836-40.

Sulis, M. L. and R. Parsons (2003). "PTEN: from pathology to biology." Trends Cell Biol 13(9): 478-83.

Taira, M., T. Iizasa, et al. (1990). "A human testis-specific mRNA for phosphoribosylpyrophosphate synthetase that initiates from a non-AUG codon." J Biol Chem 265(27): 16491-7.

Torres, J. and R. Pulido (2001). "The tumor suppressor PTEN is phosphorylated by the protein kinase CK2 at its C terminus. Implications for PTEN stability to proteasome-mediated degradation." J Biol Chem 276(2): 993-8.

Vazquez, F., S. R. Grossman, et al. (2001). "Phosphorylation of the PTEN tail acts as an inhibitory switch by preventing its recruitment into a protein complex." J Biol Chem 276 (52): 48627-30.

Vazquez, F., S. Ramaswamy, et al. (2000). "Phosphorylation of the PTEN tail regulates protein stability and function." Mol Cell Biol 20(14): 5010-8.

Wang, X., L. C. Trotman, et al. (2007). "NEDD4-1 is a proto-oncogenic ubiquitin ligase for PTEN." Cell 128(1): 129-39.

Xiao, J. H., I. Davidson, et al. (1991). "Cloning, expression, and transcriptional properties of the human enhancer factor TEF-1." Cell 65(4): 551-68.

You, M. J., D. H. Castrillon, et al. (2002). "Genetic analysis of Pten and Ink4a/Arf interactions in the suppression of tumorigenesis in mice." Proc Natl Acad Sci USA 99(3): 1455-60

What is claimed is:

1. A method for treating a solid tumor in a subject comprising administering to the subject an amount of an isolated polypeptide effective to treat the solid tumor in the subject, wherein the sequence of the polypeptide is identical to the sequence set forth in in SEQ ID NO: 1.

* * * * *